(12) United States Patent
Pereira et al.

(10) Patent No.: US 11,884,710 B2
(45) Date of Patent: *Jan. 30, 2024

(54) PEPTIDE COMPOUNDS AND METHODS OF USE IN WOUND HEALING

(71) Applicant: The Board of Regents of the University of Oklahoma, Norman, OK (US)

(72) Inventors: Heloise Anne Pereira, Edmond, OK (US); Anne Kasus-Jacobi, Midwest City, OK (US); Gina L. Griffith, McAlester, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/532,307

(22) Filed: Nov. 22, 2021

(65) Prior Publication Data
US 2022/0089665 A1    Mar. 24, 2022

Related U.S. Application Data

(60) Continuation of application No. 16/775,877, filed on Jan. 29, 2020, now abandoned, which is a continuation-in-part of application No. 15/922,246, filed on Mar. 15, 2018, now abandoned, which is a division of application No. 15/363,670, filed on Nov. 29, 2016, now abandoned, which is a continuation of application No. 14/781,801, filed as application No. PCT/US2014/034392 on Apr. 16, 2014, now Pat. No. 9,624,283.

(60) Provisional application No. 61/813,527, filed on Apr. 18, 2013, provisional application No. 61/812,584, filed on Apr. 16, 2013.

(51) Int. Cl.
| | | |
|---|---|---|
| *A61K 38/17* | (2006.01) | |
| *C07K 14/47* | (2006.01) | |
| *A61K 45/06* | (2006.01) | |
| *A61K 38/00* | (2006.01) | |

(52) U.S. Cl.
CPC .......... *C07K 14/4723* (2013.01); *A61K 38/17* (2013.01); *A61K 38/1729* (2013.01); *A61K 45/06* (2013.01); *A61K 38/00* (2013.01); *Y02A 50/30* (2018.01)

(58) Field of Classification Search
None
See application file for complete search history.

(56) References Cited

U.S. PATENT DOCUMENTS

| | | |
|---|---|---|
| 5,484,885 A | 1/1996 | Pereira et al. |
| 5,627,262 A | 5/1997 | Pereira |
| 5,877,151 A | 3/1999 | Pereira |
| 6,071,879 A | 6/2000 | Pereira |
| 6,107,460 A | 8/2000 | Pereira |
| 7,176,185 B2 | 2/2007 | Hilfinger et al. |
| 7,354,900 B2 | 4/2008 | Pereira et al. |
| 7,579,435 B2 | 8/2009 | Culler et al. |
| 7,605,123 B2 | 10/2009 | Radhakrishnan et al. |
| 7,655,480 B2 | 2/2010 | Pereira |
| 7,893,027 B2 | 2/2011 | Pereira et al. |
| 8,450,071 B2 | 5/2013 | Pereira |
| 9,096,679 B2 | 8/2015 | Pereira |
| 2003/0134989 A1 | 7/2003 | Aldrich et al. |
| 2003/0170745 A1 | 9/2003 | Pereira |
| 2003/0206938 A1 | 11/2003 | Pereira et al. |
| 2004/0048792 A1 | 3/2004 | Pereira |
| 2005/0239688 A1 | 10/2005 | Fernandez et al. |
| 2007/0135341 A1 | 6/2007 | Pereira et al. |
| 2009/0233867 A1 | 9/2009 | Pereira |
| 2010/0120689 A1 | 5/2010 | Bossard et al. |
| 2010/0136574 A1 | 6/2010 | Pereira |
| 2011/0150780 A1 | 6/2011 | Krieger et al. |
| 2011/0250623 A1 | 10/2011 | Pereira et al. |
| 2011/0281788 A1 | 11/2011 | Coote et al. |
| 2013/0195761 A1 | 8/2013 | Pereira et al. |
| 2015/0315245 A1 | 11/2015 | Pereira |

(Continued)

FOREIGN PATENT DOCUMENTS

| | | |
|---|---|---|
| WO | 2003076459 | 9/2003 |
| WO | 2003092718 | 11/2003 |
| WO | 2011103567 A2 | 8/2011 |

(Continued)

OTHER PUBLICATIONS

Bach, et al.; "A high-affinity, dimeric inhibitor of PSD-95 bivalently interacts with PDZ1-2 and protects against ischemic brain damange," PNAS, (Feb. 28, 2012); 109(9):3317-3322.
AAPPTec. Fmoc-NH-(PEG)2-Propionic Acid; Fmoc-NH-PEG2-CH2CH2COOH [872679-70-4]. AAPTec, LLC. Catalog #: LSP312, Published Oct. 18, 2010.
International Search Report dated Dec. 9, 2014, in PCT/US2014/34392, filed Apr. 16, 2014.
Written Opinion of the International Searching Authority, dated Dec. 9, 2014, in PCT/US2014/34392, filed Apr. 16, 2014.
International Search Report dated May 13, 2014, in PCT/US2013/072884, filed Dec. 3, 2013.

(Continued)

*Primary Examiner* — Fred H Reynolds
(74) *Attorney, Agent, or Firm* — Dunlap Codding, P.C.

(57) ABSTRACT

Peptide compounds and compositions containing the peptide compounds and methods for treating various infections, wounds, and skin conditions such as atopic dermatitis. Examples of wounds that may be treated include surface wounds such as lacerations, abrasions, avulsions, incisions, and amputations, pressure sores, bed sores, wounds due to peripheral vascular disease, post-surgical wounds, diabetic ulcers and wounds, burns, ocular wounds and abrasions, ocular ulcers, and treatment of inflammatory conditions such as dry eye. The peptide compounds and compositions may be used as treatments to enhance acceptance of grafts such as skin grafts and organ grafts.

2 Claims, 24 Drawing Sheets
(9 of 24 Drawing Sheet(s) Filed in Color)
Specification includes a Sequence Listing.

(56) References Cited

U.S. PATENT DOCUMENTS

2015/0374785 A1   12/2015   Pereira et al.
2016/0317617 A1   11/2016   Pereira et al.

FOREIGN PATENT DOCUMENTS

| WO | 2011133948 | | 10/2011 |
| WO | 2012051516 | | 4/2012 |
| WO | 2014089088 | A1 | 6/2014 |

OTHER PUBLICATIONS

Written Opinion of the International Searching Authority, dated May 13, 2014, in PCT/US2013/072884, filed Dec. 3, 2013.
Trauger, et al.; "Cyclization of Backbone-Substituted Peptides Catalyzed by the Thioesterase Domain from the Tyrocidine Nonribosomal Peptide Synthetase," Biochemistry (2001); vol. 40, pp. 7098-7098.
Pereira, et al.; "CAP37, a neutrophil granule-derived protein stimulates protein kinase C activity in endothelial cells" Journal of Leukocyte Biology, (Sep. 1996), vol. 60, pp. 415-422.
Hölig, et al.; "Novel RGD lipopeptides for the targeting of liposomes to integrin-expressing endothelial and melanoma cells," Protein Engineering, Design & Selection, (2004); vol. 17, No. 5, pp. 433-441.
Green, et al.; "Conotoxins Containing Nonnatural Backbone Spacers: Cladistic-Based Design, Chemical Synthesis, and Improved Analgesic Activity," Chemistry & Biology, (2007); vol. 14, pp. 399-407.
Olczak et al.; "Structural analysis of N-glycans from human neutrophil azurocidin," Biochemical and Biophysical Research Communications; (Apr. 2002), vol. 293, pp. 213-219.
Definition of moiety, from http://dictionary.reference.com/browse/moiety, pp. 1-3, accessed Aug. 26, 2010.
Terrone, et al.; "Penetratin and Related Cell-Penetrating Cationic Peptides Can Translocate Across Lipid Bilayers in the Presence of a Transbilayer Potential," Biochemistry, (2003), vol. 42, No. 47, pp. 13787-13799.
Kong, et al; "Suppression of neovascularization and experimental arthritis by D-form of anti-flt-1 peptide conjugated with mini-PEG," Angiogenesis, (2011), vol. 14, pp. 431-442.
Bechara, et al.; "Cell-penetrating peptides: 20 years later, where do we stand?" FEBS Letters, (2013), vol. 587, pp. 1693-1702.
U.S. Appl. No. 14/095,826; Heloise Anne Pereira; Notice of Allowance dated May 18, 2015.
Lee, et al.; "CAP37, a neutrophil-derived inflammatory mediator, augments leukocyte adhesion to endothelial monolayers," Academic Press; Science Direct, Microvascular Research, (2003), vol. 66, pp. 38-48.
Pereira, et al.; "Modulation of Corneal Epithelial Cell Functions by the Neutrophil-Derived Inflammatory Mediator CAP37," Investigative Ophthamoiogy & Visual Science, (Dec. 2004); vol. 45, No. 12, pp. 4284-4292.
Pereira, et al.; "Inducible Expression of the Inflammatory Protein CAP37 in the Epidermis During Wound Healing," In: "Focus on Protein Research"; ISBN:1-59033-968-1 (2004) Nova Biomedical Publications, pp. 133-148.
Ruan, et al.; "Corneal Expression of the Inflammatory Mediator CAP37," Investigative Ophthalmology & Visual Science (May 2002); vol. 43, No. 5; pp. 1414-1421.
U.S. Appl. No. 14/095,826; Pereira, H. Anne; Office Action dated Jun. 6, 2014.
U.S. Appl. No. 14/095,826; Pereira, H. Anne; Response to Office Action filed Aug. 5. 2014.
U.S. Appl. No. 14/095,826; Pereira, H. Anne; Office Action dated Oct. 27, 2014.
U.S. Appl. No. 14/095,826; Pereira, H. Anne; Response to Office Action filed Apr. 27, 2015.
U.S. Appl. No. 14/095,826; Pereira, H. Anne; Notice of Allowance dated May 18, 2015.
U.S. Appl. No. 14/649,485; Pereira, et al.; Office Action dated Nov. 24, 2015.
U.S. Appl. No. 14/649,485; Pereira, et al.; Response to Office Action filed Jan. 13, 2016.
U.S. Appl. No. 14/649,485; Pereira, et al.; Office Action dated Mar. 11, 2016.
U.S. Appl. No. 14/649,485; Pereira, et al.; Response to Office Action filed Jun. 2, 2016.
U.S. Appl. No. 14/649,485; Pereira, et al.; Final Office Action dated Jul. 6, 2016.
U.S. Appl. No. 14/649,485; Pereira, et al.; Response to Final Office Action filed Jul. 22, 2016.
U.S. Appl. No. 14/649,485; Pereira, et al.; Notice of Allowance dated Aug. 22, 2016.
Kato, et al.; "Mutational Analysis of Protein Solubility Enhancement Using Short Peptide Tags,"; Biopolymers (2006), vol. 85, No. 1, pp. 12-18.
Gault, et al.; "C-terminal mini-PEGyiation of glucose-dependent insulinotropic polypeptide exhibits metabolic stability and improved glucose homeostasis in dietary-induced diabetes," Biochem. Pharmacol. (2008); vol. 75, pp. 2325-2333.
Thomason, et al.; "Direct evidence that pkcα positively regulates wound re-epithelialization: correlation with changes in desmosomal adhesiveness," J. Pathol. (2012), vol. 227, pp. 346-356.
Diehr, et al.; "Do topical antibiotics improve wound healing?," Journal of Family Practice (2007) vol. 56, No. 2, pp. 140-144.
Popkin, et al.; "Water, Hydration, and Health," Nutr. Rev. (2010), vol. 68, No. 8, pp. 439-458.
EP14784977.2; Pereira, et al.; filed Apr. 16, 2014; Supplementary European Search Report dated Jan. 19, 2017.
U.S. Appl. No. 15/363,670; Pereira, et al.; filed Nov. 29, 2016; Office Action dated Aug. 28, 2017.
U.S. Appl. No. 15/363,670; Pereira, et al.; filed Nov. 29, 2016; Response to Office Action filed Sep. 22, 2017.
U.S. Appl. No. 15/363,670; Pereira, et al.; filed Nov. 29, 2016; Office Action dated Nov. 17, 2017.
P2016-509072; Pereira, et al.; Office Action dated Feb. 6, 2018, filed Apr. 16, 2014; English translation.
McClean, et al.; "Research Paper; (Pro3)GIP[mPEG]: novel, long-acting, mPEGylated antagonist of gastric inhibitory polypeptide for obesity-diabetes (diabesity) therapy," British Journal of Pharmacology (2008), vol. 155, No. 5, pp. 690-701.
U.S. Appl. No. 15/172,695; Pereira, et al.; Office Action dated May 24, 2018; filed Jun. 3, 2016.
Pereira, et al.; "Modulation of Corneal Epithelial Cell Functions by the Neutrophil-derived Inflammatory Mediator Cap 37," Investigative Opthamology & Visual Science (2004), vol. 45, No. 12, pp. 4284-4292.
Eckert, et al.; "Molecular Biology of Keratinocyte Differentiation," Environmental Health Perspectives (1989), vol. 80, pp. 109-116.
Griffiths, et al.; "Modulation of Leucocyte Adhesion Molecules, a T-cell Chemotaxin (IL-8) and a Regulatory Cytokine (TNF-α) in Allergic Contact Dermatitis (rhus dermatitis)," British Journal of Dermatology (1991) vol. 124, pp. 519-526.
Nagaoka, et al.; "Delayed Wound Healing in the Absence of Intercellular Adhesion Molecule-1 or L-Selectin Expression," American Journal of Pathology (2000), vol. 157, No. 1, pp. 237-247.
U.S. Appl. No. 15/172,695; Pereira, et al.; filed Jun. 3, 2016; Final Office Action dated Nov. 30, 2018.
U.S. Appl. No. 15/922,246; Pereira, et al.; filed Mar. 15, 2018; Office Action dated Dec. 4, 2018.
U.S. Appl. No. 15/922,246; Pereira, et al.; filed Mar. 15, 2018; Amendment and Response to Office Action filed Jan. 10, 2019.
U.S. Appl. No. 15/922,246; Pereira, et al.; filed Mar. 15, 2018; Office Action dated Mar. 22, 2019.
U.S. Appl. No. 15/922,246; Pereira, et al.; filed Mar. 15, 2018; Amendment and Response to Office Action filed Sep. 30, 2019.
U.S. Appl. No. 15/922,246; Pereira, et al.; filed Mar. 15, 2018; Final Office Action dated Oct. 7, 2019.
Pereira, et al.; "Synthetic Bactericidal Peptide Based on CAP37: A 37-kDa Human Neutrophil Granule-Associated Cationic Antimi-

(56) References Cited

OTHER PUBLICATIONS crobial Protein Chemotactic for Monocytes," Proc. Natl. Acad. Sci USA (1993), vol. 90, pp. 4733-4737.
Bosshart, et al.; "Arginine-Rich Cationic Polypeptides Amplify Lipopolysaccharide-Induced Monocyte Activation," Infection and Immunity (2002), vol. 70, No. 12, pp. 6904-6910.
McCabe, et al.; "Basic Residues in Azurocidin/HBP Contribute to Both Heparin Binding and Antimicrobial Activity," The Journal of Biological Chemistry (2002), vol. 277, No. 30, p. 27477-27488.
The iris Biotech catalog page for Fmoc-AEEA, http://www.iris.biotech.de/faa 1435 downloaded Jan. 31, 2017.
Sumagin, et al.; "Activation of PKCβII by PMA Facilitates Enhanced Epithelial Wound Repair Through Increased Cell Spreading and Migration," PLoS One (2013), vol. 8, No. 2, e55775.
Mustafa, et al; "Endothelium Disfunction Distracts Wound Healing of Diabetics," International Journal of Science and Technology (2012), vol. 1, No. 3, pp. 15-24.
Khamaisi, et al.; "PKC Inhibition Normalizes the Wound-Healing Capacity of Diabetic Human Fibroblasts," Journal of Clinical Investigation (2016) vol. 126, No. 3, pp. 837-853.
Ofuji, et al.; "Essential Role of a Protein Kinase C (PKC) Signal Transduction System in Corneal Epithelial Migration," Advances in Corneal Research (1997) ISBN 978-1-4613-7460-2, pp. 391-397.
Wilson, et al.; "Management of Corneal Abrasions," American Family Physician (2004) vol. 70, No. 1, pp. 123-128.
Le Tourneau, et al.; "Dose Escalation Methods in Phase I Cancer Clinical Trials," J National Cancer Inst (2009), vol. 101, pp. 708-720.
U.S. Appl. No. 15/172,695; Pereira, et al.; filed Jun. 3, 2016; Office Action dated Mar. 1, 2017.
EP 13859680.4, filed Dec. 3, 2013; Supplementary European Search Report dated Sep. 5, 2016.
U.S. Appl. No. 15/922,246, filed Mar. 15, 2018; Final Office Action dated Oct. 7, 2019.
U.S. Appl. No. 16/775,877, filed Jan. 29, 2020; Office Action dated Aug. 24, 2020.
U.S. Appl. No. 16/775,877, filed Jan. 29, 2020; Response to Office Action filed Oct. 19, 2020.
U.S. Appl. No. 16/775,877, filed Jan. 29, 2020; Office Action dated Nov. 13, 2020.
U.S. Appl. No. 16/775,877, filed Jan. 29, 2020; Response to Office Action filed May 12, 2021.
U.S. Appl. No. 16/775,877, filed Jan. 29, 2020; Final Office Action dated May 27, 2021.

PEPTIDE COMPOUNDS AND METHODS OF USE IN WOUND HEALING

CROSS REFERENCE TO RELATED APPLICATIONS/INCORPORATION BY REFERENCE STATEMENT

This application is a continuation-in-part of U.S. Ser. No. 16/775,877, filed Jan. 29, 2020, now abandoned, which is a continuation-in-part of U.S. Ser. No. 15/922,246, filed Mar. 15, 2018, now abandoned, which is a divisional of U.S. Ser. No. 15/363,670, filed Nov. 29, 2016, now abandoned, which is a continuation of U.S. Ser. No. 14/781,801, filed Oct. 1, 2015, now U.S. Pat. No. 9,624,283, issued Apr. 18, 2017; which is national stage application filed under 35 USC § 371 of International Application No. PCT/US2014/034392, filed Apr. 16, 2014; which claims benefit of US provisional application U.S. Ser. No. 61/812,584, filed Apr. 16, 2013, and US provisional application U.S. Ser. No. 61/813,527, filed Apr. 18, 2013. The '392 application also claims benefit of International Application No. PCT/US2013/072884, filed Dec. 3, 2013. The entire contents of each of the above-referenced patents and patent applications are hereby expressly incorporated herein by reference.

STATEMENT REGARDING FEDERALLY SPONSORED RESEARCH OR DEVELOPMENT

This invention was made with government support under Public Health Service Grant Number EY015534 awarded by the National Eye Institute (NEI) of the National Institutes of Health (NIH) and under Grant Number 5U01AI075391 awarded by the National Institute of Allergy and Infectious Diseases (NIAID) of the NIH. The government has certain rights in the invention.

BACKGROUND

Effective treatment of Gram negative bacterial infections has suffered due to a dearth of new antibiotics in the pharmaceutical pipeline. Only one novel antibacterial has been approved since 2006. Thus there is a clear unmet need for such therapies. Antibiotic resistance is one of the greatest threats to global human health. Thus, therapies with novel mechanisms of action that could circumvent resistance are highly desired. For example, sepsis or septic shock kills more than 200,000 people per year in the U.S. alone. Optimally, a sepsis therapeutic would serve as an antibiotic, as well as bind and neutralize the toxic effects of endotoxin (a.k.a., lipopolysaccharide, or LPS). The morbidity and mortality that results from severe infection in the U.S. alone is estimated at an annual cost of many billions of dollars. In the European Union the lost productivity and health care costs due to multi-drug resistant infections is estimated at 1.5 billion euros per year. New bioactive peptides that are effective against Gram negative infections and exhibit no or low toxicity would be a significant contribution to this global health crisis.

CAP37 (cationic antimicrobial protein of $M_r$ 37 kDa) was originally identified as a component of the oxygen-independent killing mechanism of the human neutrophil (PMN) and was demonstrated to have strong bactericidal activity against Gram negative bacteria including *Salmonella typhimurium*, *Escherichia coli*, and *Pseudomonas aeruginosa*. Distinct from its effect on bacteria, the native CAP37 protein has potent regulatory effects on host cells. It is an effective regulator of cells of the mononuclear phagocytic system such as monocytes, microglia, and macrophages. It also regulates certain corneal epithelial, endothelial, and smooth muscle cell functions.

Structure-function analysis of CAP37 previously enabled the delineation of an antibacterial domain of the CAP37 protein, which was identified as residing in residues 20 through 44 of the native molecule. A peptide comprising this 25 amino acid sequence (i.e., CAP37 (20-44) SEQ ID NO: 7) mimicked the antimicrobial activity of the native molecule and extended its range of activity to encompass *Staphylococcus aureus* and *Enterococcus faecalis*, two Gram positive bacteria. The bactericidal activity of the peptide was pH dependent, with maximum activity obtained between pH 5.0 and 5.5. Derivatives of the natural peptide sequence of 20-44, wherein either of the cysteine residues at position 26 or 42 were replaced with serine residues (CAP37 (20-44)$_{ser26}$ and CAP37 (20-44)$_{ser42}$-SEQ ID NO:1 and 4, respectively), were also produced. However, commercialization of a peptide as a first-in-class anti-infective requires the ability to, for example, (1) scale-up the synthesis of the peptide, (2) achieve purity of preferably >90%, and (3) retain activity. The 20-44 peptide and previously-known substituted versions thereof could not be produced with these features. It is to novel peptide compounds that possess such properties and which comprise various portions of CAP37 proteins and derivatives thereof, as well as to methods of use of these compounds, that the presently disclosed inventive concepts is directed.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

Several embodiments of the present disclosure are hereby illustrated in the appended drawings. It is to be noted however, that the appended drawings only illustrate several typical embodiments and are therefore not intended to be considered limiting of the scope of the present disclosure. Further, in the appended drawings, like or identical reference numerals may be used to identify common or similar elements, and not all such elements may be so numbered. The figures are not necessarily to scale, and certain features and certain views of the figures may be shown exaggerated in scale or in schematic in the interest of clarity and conciseness.

FIG. 28A shows growth curve of Pseudomonas in the absence of Cefotaxime and antibiotic, Pseudomonas in the presence of antibiotic (2.81 μg/ml), peptide (3.15 μg/ml), and antibiotic plus peptide combinations. FIG. 28B is a histogram showing Fractional area (FA), which is an indication of the MIC. Combination of Cefotaxime with 3.04 μg/ml of peptide shows significance. P=0.0143.

FIG. 29A shows growth curve of Pseudomonas in the absence of Ciprofloxacin and antibiotic, Pseudomonas in the presence of antibiotic (2.1 μg/ml), peptide (4.05 μg/ml), and antibiotic plus peptide combinations. FIG. 29B is a histogram showing Fractional area (FA), which is an indication of the MIC. Combination of Ciprofloxacin with 4.05 μg/ml of peptide shows significance. P=0.0003.

FIG. 30A shows growth curve of Pseudomonas in the absence of Levofloxacin and antibiotic, Pseudomonas in the presence of antibiotic (3.6 μg/ml), peptide (3.04 μg/ml), and antibiotic plus peptide combinations. FIG. 30B is a histogram showing Fractional area (FA), which is an indication of the MIC. Combination of Levofloxacin with 3.04 μg/ml of peptide shows significance.

DETAILED DESCRIPTION

Figure 1:
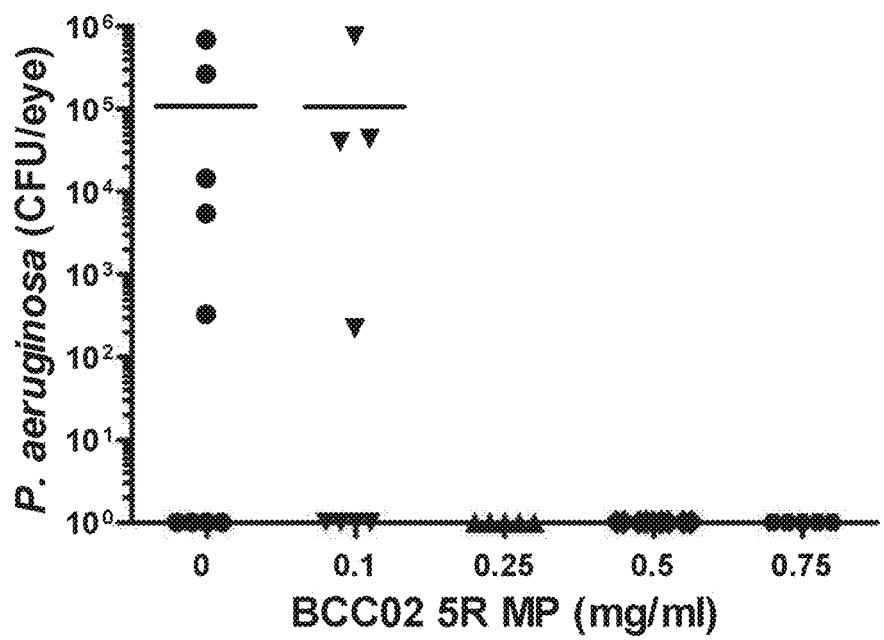
FIG. 1 shows that BCC002-5RMP (SEQ ID NO:21) has antimicrobial activity in mouse bacterial keratitis. A circular wound was created on the mouse cornea by removing the epithelium and infected with $10^5$ colony forming units (CFU) of *P. aeruginosa* (ATCC® 27853™ (American Type Culture Collection, Manassas, Va.)). Infected wounds were treated with saline (0.9% sodium chloride, vehicle control) or saline containing indicated concentrations of peptide every 15 minutes for 2 hours, then every 30 minutes for 3 hours on the first day. Infected wounds were treated twice on the second day and once on the third day. Mice were killed at 48 hours post-infection, and CFU/eye were quantified. The means were plotted and are representative of 5 to 9 mice per group. Mann Whitney test was performed for each group as compared to the saline control group. *P=0.014. In compound names such as BCC02-5RMP used herein, "R" represents arginine, and "MP" represents a small PEG molecule as defined elsewhere herein (such as, for example but not by way of limitation, "AEEP").

Before describing various embodiments of the presently disclosed inventive concepts in more detail by way of exemplary description, examples, and results, it is to be understood that the presently disclosed inventive concepts are not limited in application to the details of methods and compositions as set forth in the following description. The presently disclosed inventive concepts are capable of other embodiments or of being practiced or carried out in various ways. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the presently disclosed inventive concepts may be practiced without these specific details. In other instances, features which are well known to persons of ordinary skill in the art have not been described in detail to avoid unnecessary complication of the description.

Unless otherwise defined herein, scientific and technical terms used in connection with the presently disclosed inventive concepts shall have the meanings that are commonly understood by those having ordinary skill in the art. Further, unless otherwise required by context, singular terms shall include pluralities and plural terms shall include the singular.

All patents, published patent applications, and non-patent publications mentioned in the specification are indicative of the level of skill of those skilled in the art to which the presently disclosed inventive concepts pertain. All patents, published patent applications, and non-patent publications referenced in any portion of this application are herein expressly incorporated by reference in their entirety to the same extent as if each individual patent or publication was specifically and individually indicated to be incorporated by reference.

All of the compositions and methods of production and application thereof disclosed herein can be made and executed without undue experimentation in light of the present disclosure. While the compositions and methods of the presently disclosed inventive concepts have been described in terms of particular embodiments, it will be apparent to those of skill in the art that variations may be applied to the compositions and/or methods and in the steps or in the sequence of steps of the method described herein without departing from the concept, spirit, and scope of the inventive concepts. All such similar substitutes and modifications apparent to those having ordinary skill in the art are deemed to be within the spirit, scope, and concept of the inventive concepts as defined herein.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the composition, or the variation that exists among the study subjects.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

The term "naturally-occurring" as used herein as applied to an object refers to the fact that an object can be found in nature. For example, a protein that is present in a source that can be isolated from a source in nature and which has not been intentionally modified by man in the laboratory or otherwise, other than to be purified, is naturally-occurring.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability to modify the physiological system of an organism without reference to how the active agent has its physiological effects.

As used herein, "pure," or "substantially pure" means an object species (e.g., a particular peptide compound) is the predominant species present (i.e., on a molar basis it is more abundant than any other active agent in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. Most particularly, the object species may be purified to essential homogeneity (contaminant species cannot be detected in the composition by conventional detection methods) wherein the composition consists essentially of a single macromolecular species. The term "pure" or "substantially pure" also refers to preparations where the object species (e.g., the peptide compound) is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

In certain compound names used herein, such as BCC01-5RMP, BCC002-5RMP, and BCC002-5RMP, "R" represents arginine, and "MP" represents a solubilizing moiety, such as a small PEG molecule (e.g., "AEEP") as defined elsewhere herein.

The terms "subject" and "patient" are used interchangeably herein and will be understood to refer to a warm blooded animal, particularly a mammal. Non-limiting examples of animals within the scope and meaning of this term include guinea pigs, dogs, cats, rats, mice, horses, goats, cattle, sheep, zoo animals, non-human primates, and humans.

"Treatment" refers to therapeutic treatments. "Prevention" refers to prophylactic or preventative treatment measures. The term "treating" refers to administering the composition to a patient for therapeutic purposes.

The terms "therapeutic composition" and "pharmaceutical composition" refer to a peptide compound-containing composition that may be administered to a subject by any method known in the art or otherwise contemplated herein, wherein administration of the composition brings about a therapeutic effect as described elsewhere herein. Non-limiting examples of modes of administration include oral, topical, retrobulbar, subconjunctival, transdermal, parenteral, subcutaneous, intranasal, intramuscular, intraperitoneal, intravitreal, and intravenous routes, including both local and systemic applications. In addition, the compositions of the presently disclosed inventive concepts may be designed to provide delayed, controlled, extended, and/or sustained release using formulation techniques which are well known in the art.

The term "topical" as used herein to define a mode of administration, means that a material is administered by being applied to the skin or internally to an epithelial tissue.

The term "effective amount" refers to an amount of a peptide compound which is sufficient to exhibit a detectable therapeutic effect without excessive adverse side effects (such as toxicity, irritation and allergic response) commensurate with a reasonable benefit/risk ratio when used in the manner of the inventive concepts. The therapeutic effect may include, for example but not by way of limitation, a partial or complete elimination of an infection or wound. The effective amount for a patient will depend upon the type of patient, the patient's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

The term "ameliorate" means a detectable or measurable improvement in a subject's condition, disease, or symptom thereof. A detectable or measurable improvement includes a subjective or objective decrease, reduction, inhibition, closure, suppression, limit, or control in the occurrence, frequency, severity, progression, or duration of the condition or disease, or an improvement in a symptom or an underlying cause or a consequence of the disease, or a reversal of the disease. A successful treatment outcome can lead to a "therapeutic effect" or "benefit" of completely or partially decreasing, reducing, inhibiting, suppressing, limiting, controlling, or preventing the occurrence, frequency, severity, progression, or duration of a disease or condition, or consequences of the disease or condition, such as (but not limited to) a wound or infection, in a subject.

A decrease or reduction in worsening, such as stabilizing the condition or disease, such as a wound or infection, is also a successful treatment outcome. A therapeutic benefit therefore need not be complete ablation or reversal of the disease or condition, or of any one of, or most, or all adverse symptoms, complications, consequences or underlying causes associated with the disease or condition. Thus, a satisfactory endpoint may be achieved when there is an incremental improvement such as a partial decrease, reduction, inhibition, suppression, limit, control, or prevention in the occurrence, frequency, severity, progression, or duration, or inhibition or reversal of the condition or disease (e.g., stabilizing), over a short or long duration of time (hours, days, weeks, months, etc.), such as partial closure of a wound. Effectiveness of a method or use, such as a treatment that provides a potential therapeutic benefit or improvement of a condition or disease, can be ascertained by various methods, measurements, and testing assays.

As used herein, the term "concurrent therapy" is used interchangeably with the terms "combination therapy" and "adjunct therapy," and will be understood to mean that the subject in need of treatment is treated or given another drug for the condition (e.g., ibuprofen or a muscle relaxant) in conjunction with the pharmaceutical compositions of the presently disclosed inventive concepts. This concurrent therapy can be sequential therapy, where the patient is treated first with one composition and then the other composition, or the two compositions are given simultaneously. Non-limiting examples of combination therapies in accordance with the presently disclosed inventive concepts include a combination of two or more of the peptides described herein, one or more of said peptides in combination with one or more other antibiotics, or one or more of said peptides in combination with another drug given to treat a particular condition.

Abbreviations used herein, as well as the whole word/phrase represented thereby, are provided for reference hereinafter. AEEA ($-NHCH_2CH_2OCH_2CH_2OCH_2CO-$ or $NH_2CH_2CH_2OCH_2CH_2OCH_2CO-$) is an N terminal solubilizing group derived from [2-(2-amino-ethoxy)-ethoxy]-acetic acid (also known as 8-Amino-3,6-dioxaoctanoic acid). AEEEA ($-NHCH_2CH_2OCH_2CH_2OCH_2CH_2OCH_2CO-$ or $NH_2CH_2CH_2OCH_2CH_2OCH_2CH_2OCH_2CO-$) is an N terminal solubilizing group derived from {2-[2-(2-amino-ethoxy)-ethoxy]-ethoxy}-acetic acid (also known as 11-Amino-3,6,9-trioxaundecanoic acid). AEEP ($-NHCH_2CH_2OCH_2CH_2OCH_2CH_2CO-$ or $NH_2CH_2CH_2OCH_2CH_2OCH_2CH_2CO-$) is an N terminal solubilizing group derived from [3-(2-amino-ethoxy)-ethoxy]-propanoic acid (also known as 9-amino-4,7-dioxanonanoic acid). AEEEP ($-NHCH_2CH_2OCH_2CH_2OCH_2CH_2OCH_2CH_2CO-$ or $NH_2CH_2CH_2OCH_2CH_2OCH_2CH_2OCH_2CH_2CO-$) is an N terminal solubilizing group derived from [3-[2-(2-amino-ethoxy)-ethoxy]-ethoxy]-propanoic acid (also known as 12-amino-4,7,10-trioxadodecananoic acid). ANOVA: analysis of variance. CAP37: cationic antimicrobial protein of molecular weight 37 kDa. BCA: bicinchoninic acid. BSA: bovine serum albumin. DAB: diaminobenzidine tetrahydrochloride. BPI: bactericidal permeability-increasing. DAG: diacyl glycerol. EDTA: ethylenediaminetetraacetic acid. EGF: epidermal growth factor. EGFR: epidermal growth factor receptor. ERK: extracellular-signal-regulated kinase. FBS: fetal bovine serum. GCSF: granulocyte colony-stimulating factor. GM-CSF: granulocyte macrophage colony-stimulating factor. GPCR: G protein-coupled receptor. HB-EGF: heparin binding-epidermal growth factor. HBSS: Hank's balanced salt solution. HCEC(s): human corneal epithelial cell(s). H&E: hematoxylin and eosin. HGF: hepatocyte growth factor. HBD-1: human beta-defensin-1. IL-6: interleukin-6. IL-8: interleukin-8. IP-10: interferon-inducible protein-10. KC: keratinocyte-derived chemokine. KSFM: keratinocyte serum free media. LPS: lipopolysaccharide. MCP-1: monocyte chemotactic protein-1. NADP: nicotinamide adenine dinucleotide phosphate. PBS: phosphate buffered saline. PDGF-BB: platelet derived growth factor-BB. PKC: protein kinase C. PMA: phorbol 12-myristate 13-acetate. PMSF: phenylmethylsulfonyl fluoride. RIPA: radioimmunoprecipitation assay. ROS: reactive oxygen species. SDS-PAGE: sodium dodecyl sulfate polyacrylamide gel electrophoresis. SFM: serum free media. TBS: Tris-buffered saline. TBST: Tris-buffered saline TWEEN® 20 (Thermo Fisher Scientific, Pittsburgh, Pa.). TGF-β: transforming growth factor beta. TNF-α: tumor necrosis factor alpha.

Described herein in certain embodiments of the present disclosure is a new generation of peptide compounds that have enhanced antibacterial, antifungal, wound healing, and graft healing activities and that can be scaled-up (i.e., have high solubility), and that have high purity (in some embodiments at least 80%). In certain embodiments, modifications were made in the various peptides derived from native CAP37 protein, including peptides derived from the 20-44 (SEQ ID NO:7), 23-42 (SEQ ID NO:14), 95-122 (SEQ ID NO:26), 102-122 (SEQ ID NO:27), and 120-146 (SEQ ID NO:28) amino acid positions of CAP37 protein. Various embodiments of the peptide compounds have shown high purity, solubility, and potent activity against a number of bacterial species, including but not limited to, *Pseudomonas aeruginosa* (including antibiotic resistant clinical isolates), *Acinetobacter baumannii, Salmonella typhimurium*, and *Escherichia coli*. In some embodiments, the peptide compounds and compositions disclosed herein may be used to treat bacterial and/or fungal infections.

In certain embodiments, the peptide compounds and compositions disclosed herein may be used to treat atopic dermatitis (eczema) in a subject.

In certain embodiments, the peptide compounds and compositions disclosed herein may be used to treat and promote healing of wounds in subjects who are otherwise healthy, i.e., subjects who do not have chronic conditions which impair wound healing, such as (but not limited to) diabetes. Examples of such wounds in otherwise healthy subjects include, but are not limited to, surface wounds such as lacerations, abrasions, avulsions, incisions, and amputations, chronic "non-healing wounds" or "slow-healing" wounds such as pressure sores and bed sores, "non-healing" or "slow-healing" post-surgical wounds, and burns.

In certain embodiments, the peptide compounds and compositions are used to enhance and/or promote healing of acute wounds of a non-diabetic nature (e.g., lacerations, abrasions, avulsions, incisions, amputations, and burns) in diabetic subjects. In certain embodiments, the peptide compounds and compositions are used to enhance and/or promote healing of chronic wounds such as (but not limited to) diabetic wounds and ulcers (for example of the legs and feet) in subjects having diabetes, or wounds due to peripheral vascular disease or cardiovascular disease.

The peptide compounds and compositions in certain embodiments may be used as treatments to enhance acceptance of grafts such as skin grafts and organ grafts. The peptide compounds and compositions in certain embodiments may be used as treatments for ocular infections, ocular wounds and abrasions, and ocular ulcers and treatment of inflammatory conditions such as dry eye. The peptide compounds and compositions may be used in combination with each other, in combination with other antibiotics, or in combination with another drug given to treat a particular condition.

As noted elsewhere herein, a successful treatment does not require complete healing or closure of a wound but may comprise an amelioration of the wound, for example a partial closure of the wound or partial epithelialization of the wound.

Certain embodiments of the peptide compounds are represented by Formula (I) below:

$$S—X_R\text{-Pep-}Y_R \qquad (I)$$

wherein Pep is one of SEQ ID NOS:1-14, 25-31, and 47 or another appropriate amino acid sequence described herein; $X_R$ and $Y_R$ are each independently 0, 1, 2, 3, 4, 5, or 6 arginine residues, with the proviso that $(X_R+Y_R)$ is 4, 5, or 6 arginine residues; and S is a solubilizing moiety made up of 1, 2, 3, 4, 5, 6, 7, 8, 9, or 10 (i.e., 1-10) small PEG subunits having the formula $NH_nCH_2CH_2—(OCH_2CH_2)_p—O(CH_2)_qCO—$ wherein q=0, 1, 2, 3, or 4 and p=1, 2, 3, 4, 5, 6, 7, or 8, and n=1 or 2 wherein n=2 if the subunit is terminal.

In certain non-limiting embodiments, S may comprise one subunit AEEA ($NH_2CH_2CH_2OCH_2CH_2OCH_2CO—$), or two subunits AEEA ($NH_2CH_2CH_2OCH_2CH_2OCH_2CONHCH_2CH_2OCH_2CH_2OCH_2CO—$), or one subunit AEEEA ($NH_2CH_2CH_2OCH_2CH_2OCH_2CH_2OCH_2CO—$), or two subunits AEEEA ($NH_2CH_2CH_2OCH_2CH_2OCH_2CH_2OCH_2CONHCH_2CH_2OCH_2CH_2OCH_2CH_2OCH_2CO—$), or one AEEA and one AEEEA in any order.

In certain non-limiting embodiments, S may comprise one subunit AEEP ($NH_2CH_2CH_2OCH_2CH_2OCH_2CH_2CO—$), or two subunits AEEP ($NH_2CH_2CH_2OCH_2CH_2OCH_2CH_2CONHCH_2CH_2OCH_2CH_2OCH_2CH_2CO—$), or one subunit AEEEP ($NH_2CH_2CH_2OCH_2CH_2OCH_2CH_2OCH_2CH_2CO—$), or two subunits AEEEP ($NH_2CH_2CH_2OCH_2CH_2OCH_2CH_2OCH_2CH_2CONHCH_2CH_2OCH_2CH_2OCH_2CH_2OCH_2CH_2CO—$), or one AEEP and one AEEEP in any order.

In various non-limiting embodiments, the 1-10 small PEG subunits may be identical or may be a combination of different small PEG subunits (in any order) having the formula $—NHCH_2CH_2—(OCH_2CH_2)_p—O(CH_2)_qCO—$ as described above. In at least one embodiment, S may comprise at least one subunit which is not AEEA (q=1, p=1), or AEEEA (q=1, p=2). For example, in one embodiment S comprises one of (i) AEEA and AEEP, (ii) AEEA and AEEEP, (iii) AEEEA and AEEP, or (iv) AEEEA and AEEEP, but does not include (i) AEEA and AEEA, (ii) AEEA and AEEEA, or (iii) AEEEA and AEEEA.

The $—O(CH_2)_qCO—$ portion ("head group") of the PEG subunit (S) which is attached to the peptide $(X_R\text{-Pep-}Y_R)$ may be further modified to comprise a number of alternate embodiments of the $(CH_2)_q$ portion of the head group. These alternate embodiments, as well as those described above, can be characterized by Formula (II) below:

$$—O(CR_1R_2)_qCO— \qquad (II)$$

wherein $R_1$ and $R_2$ of Formula II are side groups on C (i.e., "$R_1—C—R_2$") wherein q=β-4, and $R_1$ and $R_2$ are selected from H, $CH_3$, and $CH_2CH_3$. When q=1, either or both of $R_1$ and $R_2$ can be selected from H, $CH_3$, and $CH_2CH_3$. When q=2, either of the two $R_1$ groups and either of the two $R_2$ groups can be selected from H, $CH_3$, and $CH_2CH_3$. When q=3, any of the three $R_1$ groups and any of the three $R_2$ groups can be selected from H, $CH_3$, and $CH_2CH_3$. When q=4, any of the four $R_1$ groups and any of the four $R_2$ groups can be selected from H, $CH_3$, and $CH_2CH_3$. Thus, in these non-limiting embodiments, the head group may comprise one or more substitutions for H on the carbons of the carbon backbone when C=1-4.

Examples of embodiments of head groups having Formula II include, but are not limited to:
1. —$OCH_2$ $CH_2CO$— (e.g., as in AEEP).
2. —$OCH_2CO$— (e.g., as in AEEA).
3. —$OCH_2$ $CH_2$ $CH_2CO$— (wherein q=3).
4. —$OCH_2$ $CH_2$ $CH_2$ $CH_2CO$— (wherein q=4 i.e., a pentanoic head group).
5. —$OC(CH_3)_2CO$— (wherein $R_1$ and $R_2$=$CH_3$ and q=1).
6. —$OCH_2C(CH_3)_2CO$— (wherein $R_1$ and $R_2$=H on the first carbon and $R_1$ and $R_2$=$CH_3$ on the second carbon and q=2).
7. —$OCH_2$ $CH_2$ $CH_2CH(CH_3)CO$— (wherein $R_1$=H and $R_2$=$CH_3$ on one carbon, and $R_1$ and $R_2$=H on every other carbon and q=4).
8. —$OCH_2$ $CH_2$ $CH_2C(CH_3)_2CO$— (wherein $R_1$ and $R_2$=$CH_3$ on one carbon, and $R_1$ and $R_2$=H on all other carbons).
9. —$OCH_2$ $CH_2$ $CH_2CH(CH_2CH_3)CO$— (wherein $R_1$=H and $R_2$=$CH_2CH_3$ on one carbon, and $R_1$ and $R_2$=H on all other carbons).
10. —$OCH(CH_3)$ $CH_2$ $CH_2CH(CH_2CH_3)CO$— (wherein $R_1$=H and $R_2$=$CH_3$ on one carbon, $R_1$=H and $R_2$=$CH_2CH_3$ on one carbon, and $R_1$ and $R_2$=H on all other carbons).

All stereoisomers of the peptide compounds formed based on the solubilizing units described for Formula II are intended to be included in the presently disclosed inventive concepts.

In one embodiment, $X_R$ includes four arginine residues, while $Y_R$ is one arginine residue. In addition, the S group may include, as indicated above, two AEEP moieties for example. Particular non-limiting examples of peptide compounds in accordance with the presently disclosed inventive concepts include one or more peptide compounds that have the sequence of one of SEQ ID NOS:21-23 and 32-46, as described in further detail herein below.

In one non-limiting embodiment, the "Pep" sequence of the Formula (I) peptide compound described herein may comprise the following sequence (SEQ ID NO:25):

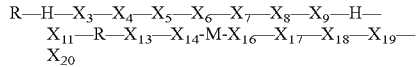

wherein $X_3$ and $X_{13}$ are phenylalanine, tyrosine, arginine, lysine or histidine; $X_4$ is selected from cysteine, serine, threonine, and methionine; $X_5$ and $X_6$ are selected from glycine and alanine; $X_7$, $X_{11}$, and $X_{14}$ are selected from alanine, leucine, isoleucine, and valine; $X_9$, $X_{17}$, and $X_{18}$ are selected from alanine, leucine, isoleucine, and valine; $X_{16}$ is selected from serine, threonine, and methionine; $X_{19}$ is selected from serine, threonine and methionine; $X_{20}$ is selected from cysteine, serine, and methionine; R is arginine; H is histidine; and M is methionine. This sequence is a derivative of SEQ ID NO:8 (i.e., amino acids 23-42 of CAP37 protein).

In another non-limiting embodiment, the "Pep" sequence of the Formula (I) peptide compound described herein may comprise the following sequence (SEQ ID NO:47):

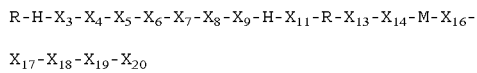

wherein $X_3$ and $X_{13}$ are phenylalanine, tyrosine, arginine, lysine, or histidine; $X_4$ is selected from cysteine, serine, threonine, and methionine; $X_5$ and $X_6$ are selected from glycine and alanine; $X_7$, $X_{11}$, and $X_{14}$ are selected from alanine, leucine, isoleucine, and valine; $X_9$, $X_{17}$, and $X_{18}$ are selected from alanine, leucine, isoleucine, and valine; $X_{16}$ is selected from serine, threonine, and methionine; $X_{19}$ is selected from serine, threonine, and methionine; $X_{20}$ is selected from cysteine, serine, threonine, and methionine; R is arginine; H is histidine; and M is methionine.

Certain embodiments of the presently disclosed inventive concepts include peptide compounds having the sequences of at least one of SEQ ID NOS:8-14 (i.e., sequences similar to SEQ ID NOS: 1-7, respectively, wherein the N-terminal three amino acids (NQG) and the C-terminal two amino acids (FQ) are truncated such that the Pep portion of the peptide compound contains 20 amino acids rather than 25 amino acids). In other embodiments of the presently disclosed inventive concepts, one or more of the following substitutions may be made in one or more of SEQ ID NOS:7 and 14: phenylalanine replaced by tyrosine; glycine replaced by alanine; valine replaced by alanine, leucine, or isoleucine; alanine replaced by leucine, isoleucine, or valine; leucine replaced by alanine, isoleucine, or valine; isoleucine replaced by valine, leucine, or alanine; serine replaced by threonine or methionine, and threonine replaced by serine or methionine; and the cysteine residues may be substituted with a serine, threonine, or methionine, as long as one cysteine of the two cysteine residues remains present. Similarly, one or more conservative substitutions may be made in one or more of SEQ ID NOS: 26-35 when these sequences are used in the peptide compounds described herein.

One non-limiting example of a composition constructed in accordance with the present disclosure includes a composition comprising the peptide compound of SEQ ID NO:21 [(AEEP)-(AEEP)-RRRRNQGRHFSGGALIHARF-VMTAASCFQR], and wherein the peptide compound is effective in enhancing the therapeutic efficacy of an antibiotic in a subject when administered to the subject in combination with the antibiotic. Another non-limiting example of a composition constructed in accordance with the presently disclosed inventive concepts includes a composition comprising the peptide of SEQ ID NO:32 [(AEEP)-(AEEP)-RRRRGTRCQVAGWGSQRSGGRLSRFPRFVNVR], and wherein the peptide compound has wound healing and antibacterial activity in a subject in need of such therapy.

The compositions of the presently disclosed inventive concepts may contain multiple peptide compounds, wherein each peptide compound is represented by Formula (I) as described herein above. For example, but not by way of limitation, the composition may include at least two peptide compounds, wherein each of the at least two peptide compounds is further defined as having the sequence of one of SEQ ID NOS:21-23 and 32-46. In another non-limiting example, the composition may include at least two peptide compounds as represented by Formula (I), wherein Pep of a first peptide compound is one of SEQ ID NOS:1-14 and 25, and Pep of a second peptide compound is one of SEQ ID NOS:26-31. In yet another non-limiting example, the composition may include at least two peptide compounds as represented by Formula (I), wherein Pep of a first peptide compound is one of SEQ ID NOS:26-27, and Pep of a second peptide compound is one of SEQ ID NOS:28-31.

Further, when multiple peptide compounds are present in the compositions of the presently disclosed inventive concepts, the multiple peptide compounds may be multimerized to form homomultimers or heteromultimers by linkage across the cysteine residues. One non-limiting example of multimerization that may be utilized in accordance with the presently disclosed inventive concepts is dimerization to form homodimers and/or heterodimers. One non-limiting method of multimerization includes linkage via "intermolecular oxidation," in which the thiol group attached to the cysteine at position 26 could be linked to an SH group from another Cys 26 peptide, thus giving a homodimer. In another non-limiting dimerization method, the SH group at Cys 42 could be cyclized with the SH group on Cys 42 from another peptide, giving a Cys 42 homodimer. A third non-limiting alternative includes the linkage of the thiol groups between Cys 42 and Cys 26 of separate peptides to give a heterodimer.

The compositions of the presently disclosed inventive concepts may also contain at least one additional therapeutically active agent. Any therapeutically active agent known in the art or otherwise contemplated herein may be combined with the peptide compound in the compositions of the presently disclosed inventive concepts. Non-limiting examples of therapeutically active agents that may be utilized in accordance with the presently disclosed inventive concepts include antibiotics, other therapeutically active peptides, antibacterial agents, antifungal agents, wound healing agents, and/or graft acceptance agents.

Any therapeutically active peptide known in the art or otherwise contemplated herein may be combined with the peptide compounds in the composition of the presently disclosed inventive concepts. Non-limiting examples of therapeutically active peptides include CAP37 peptides, such as but not limited to, the peptides of SEQ ID NOS: 26-28. One particular non-limiting example of a composition contains (a) at least one peptide compound of one of SEQ ID NOS:21-23, and (b) at least one additional therapeutic peptide of one of SEQ ID NOS:26-28. Another particular non-limiting example of a composition contains (a) at least one peptide compound of one of SEQ ID NOS:32-35, and (b) at least one additional therapeutic peptide of one of SEQ ID NOS:26-27.

Any antibiotic known in the art or otherwise contemplated herein may be utilized in accordance with the presently disclosed inventive concepts. Examples of antibiotics (e.g., antibacterial agents) which may be used in combination with the peptide compounds of the present disclosure include, but are not limited to, gentamicin, amikacin, kanamycin, tobramycin, neomycin, ertapenem, doripenem, imipenem/cilastatin, meropenem, ceftazidime, cefepime, ceftaroline, ceftobiprole, aztreonam, piperacillin, polymyxin B, Colistin, ciprofloxacin, levofloxacin, moxifloxacin, gatifloxacin, tigecycline, and combinations and derivatives thereof. In particular, the following non-limiting examples of antibiotics may be used in combination with peptide compounds that promote wound healing: gentamicin, amikacin, kanamycin, tobramycin, neomycin, ertapenem, doripenem, imipenem/cilastatin, meropenem, ceftazidime, cefepime, ceftaroline, ceftobiprole, aztreonam, piperacillin, polymyxin B, Colistin, ciprofloxacin, levofloxacin, moxifloxacin, gatifloxacin, tigecycline, clindamycin, clarithromycin, vancomycin, azithromycin, cefixime, ceftriaxone, cefamandole, cefotaxime, cefdinir, bacitracin, sulfacetamide, doxycycline, and combinations and derivatives thereof.

The peptide compounds of the compositions of the presently disclosed inventive concepts may be produced by any methods known in the art. For example, the peptide compounds may be produced synthetically or may be produced by recombinant methods. Thus, other embodiments of the presently disclosed inventive concepts include a DNA molecule having a nucleotide sequence that encodes a portion or all of the compositions described herein above. For example, the DNA molecule may have a nucleotide sequence encoding a peptide compound having an amino acid sequence as defined in any of the amino acid sequences listed, described, or otherwise contemplated herein, including for example but not by way of limitation, those having substituted cysteine residues at positions 26 or 42.

Other embodiments of the presently disclosed inventive concepts include pharmaceutical compositions that contain a therapeutically-effective or pharmaceutically-effective amount of at least one active ingredient (i.e., one or more of the compositions described herein above) in combination with a pharmaceutically-acceptable carrier. As used herein, a "pharmaceutically acceptable carrier" is a pharmaceutically acceptable solvent, suspending agent, or vehicle for delivering the compositions of the presently disclosed inventive concepts to the subject. The carrier may be, for example but not by way of limitation, liquid or solid, and the carrier may be selected with the planned manner of administration in mind. Examples of pharmaceutically acceptable carriers that may be utilized in accordance with the present disclosure include, but are not limited to, polyethylene glycol (PEG), polymers, liposomes, ethanol, DMSO, aqueous buffers, solvents, oils, DPPC, lipids, and combinations thereof.

Particular non-limiting examples of pharmaceutical compositions constructed in accordance with the present disclosure include: (a) a pharmaceutical composition comprising a composition that includes a peptide compound as represented by Formula (I) in combination with a pharmaceutically-acceptable carrier; (b) a pharmaceutical composition comprising at least two peptide compounds as represented by Formula (I) in combination with a pharmaceutically-active carrier; and (c) a pharmaceutical composition comprising at least one composition that includes a peptide compound as represented by Formula (I) in combination with at least one therapeutically active agent (such as but not limited to, a peptide compound or an antibiotic) and a pharmaceutically-acceptable carrier.

The pharmaceutical compositions may contain, in addition to the peptide compound and pharmaceutically-acceptable carrier, one or more additional components, including but not limited to, diluents, fillers, salts, buffers, stabilizers, solubilizers, and other materials well known in the art. Suitable carriers, vehicles, and other components that may be included in the formulation are described, for example, in *Remington: The Science and Practice of Pharmacy,* 21$^{st}$ ed. The term "pharmaceutically acceptable" means a non-toxic material that does not interfere with the effectiveness of the biological activity of the active ingredient(s). The characteristics of the carrier will depend on the route of administration.

The pharmaceutical composition of the presently disclosed inventive concepts may be in the form of a liposome in which the peptide compound is disposed, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

As is evident from the above, in various embodiments, the peptide compounds of the presently disclosed inventive concepts (e.g., as characterized by Formula (I)) find uses as antibacterial and/or antifungal therapeutics, as treatments for ocular infections, surface wounds, ocular wounds or abrasions and/or ocular ulcer treatments, ocular dry eye treatments, as surface wound treatments to promote healing, and/or as treatments to promote healing and acceptance of skin and/or organ grafts.

Thus, certain embodiments of the presently disclosed inventive concepts include a method of treating and/or inhibiting a bacterial and/or fungal infection in a patient, subject, and/or mammal, and/or a method of prophylactically preventing (and/or reducing the occurrence of) a bacterial and/or fungal infection in a patient, subject, and/or mammal; in this method, any of the compositions described herein above or otherwise contemplated herein is administered to the patient, subject, and/or mammal. In particular non-limiting embodiments, the bacterial infection is caused by a Gram negative bacterium, such as but not limited to, *Pseudomonas aeruginosa, Escherichia* coli, *Salmonella typhimurium*, and *Acinetobacter baumannii*. In other non-limiting embodiments, the fungal infection is caused by a fungal organism selected from the group consisting of *Candida* spp., *Saccharomyces cerevisiae, Histoplasma* spp., *Histoplasma capsulatum, Aspergillus* spp., *Aspergillus fumigatus*, and *Cryptococcus neoformans*.

In certain embodiments, the presently disclosed inventive concepts also include methods (including but not limited to, topical and/or systemic methods) of treating ocular wounds, ocular infections, ulcers, and/or infections in a patient, subject, and/or mammal. In additional embodiments, the presently disclosed inventive concepts also include methods of treating surface wounds in a patient to promote healing of the wound; in this method, any of the compositions described herein above or otherwise contemplated herein is administered (such as but not limited to, topically and/or systemically) to the patient, subject, and/or mammal. Non-limiting examples of such wounds which can be treated with the peptide compounds described herein include lacerations, abrasions, avulsions, incisions, and amputations, and "non-healing wounds" such as diabetic ulcers (for example of the legs and feet), pressure sores, wounds due to peripheral vascular disease, burns, infected wounds, surgical wounds, and other wounds and conditions described elsewhere herein.

In other embodiments, the presently disclosed inventive concepts also include methods of treating organ graft(s) and/or skin graft(s) for promoting the healing and acceptance thereof in a patient, subject, and/or mammal; in this method, any of the compositions described herein above or otherwise contemplated herein is administered (such as but not limited to, topically and/or systemically) to the patient, subject, and/or mammal.

The peptide compounds described or otherwise contemplated herein can be administered (a) in combination with one another, and/or (b) in combination with at least one additional therapeutic agent (such as but not limited to, an antibacterial agent (antibiotic), an antifungal agent, or other therapeutically active peptides, including but not limited to, other CAP37 peptides). Examples of such antibacterial agents are described above. Examples of antifungal agents which can be administered in combination with the presently described peptide compounds include, but are not limited to, those in the following classes: polyenes (e.g., Nystatin, Amphotericin B, and Pimaricin), azoles (e.g., Ketoconazole, Fluconazole, Itraconazole, Voriconazole, and Posaconazole), allylamine and morpholines (e.g., Naftifine, Terbinafine, and amorolfine), echinocandins (e.g. Micafungin, Caspofungin, and Pneumocandin), and anti-metabolites (e.g., 5-Flurocytosine).

The phrase "in combination" as used in this context means that the peptide compound(s) and/or the therapeutic agent(s) are given substantially contemporaneously, simultaneously, and/or wholly or partially sequentially; when delivered wholly or partially sequentially, the agent may be administered before and/or after the peptide compound, and vice versa. In a non-limiting example, the compound is used in a combination therapy with conventional antibiotic chemotherapeutics and/or treatments, for example antibiotics to which bacterial organisms have generally developed a resistance.

Certain other embodiments of the presently disclosed inventive concepts include methods of enhancing the efficacy of an antibiotic in the treatment of a bacterial infection. In one embodiment of the method, a therapeutically-effective amount of any of the compositions described or otherwise contemplated herein that comprises an antibiotic and a peptide compound is administered to the subject. The therapeutically-effective amount of the composition includes an amount of the antibiotic that: (i) has suboptimal activity or is ineffective against the bacteria when administered alone, and (ii) is effective against the bacteria when administered in combination with the peptide compound.

Another embodiment of the method involves administration to the subject of two separate components: (a) a composition as described or otherwise contemplated herein and that comprises a peptide compound, and (b) an antibiotic. The antibiotic is administered in an amount that: (i) has suboptimal activity or is ineffective against the bacteria when administered alone, and (ii) is effective against the bacteria when administered in combination with the peptide compound. The antibiotic and composition may be administered simultaneously or wholly or partially sequentially; when administered wholly or partially sequentially, either component may be administered first.

Certain embodiments of the presently disclosed inventive concepts include methods of enhancing the efficacy of an antibiotic in the treatment of at least one of a wound and a graft to promote healing of the wound and/or acceptance of the graft in a subject in need of such treatment. In one embodiment of the method, a therapeutically-effective amount of any of the compositions described or otherwise contemplated herein that comprises an antibiotic and a peptide compound is administered to the subject. The therapeutically-effective amount of the composition includes an amount of the antibiotic that: (i) has suboptimal activity or is ineffective in promoting healing of the wound and/or acceptance of the graft when administered alone, and (ii) is effective in promoting healing of the wound and/or acceptance of the graft when administered in combination with the peptide compound.

Another embodiment of the method involves administration to the subject of two separate components: (a) a composition as described or otherwise contemplated herein and that comprises a peptide compound, and (b) an antibiotic. The antibiotic is administered in an amount that: (i) has suboptimal activity or is ineffective in promoting healing of the wound and/or acceptance of the graft when administered alone, and (ii) is effective in promoting healing of the wound and/or acceptance of the graft when administered in combination with the peptide compound. The antibiotic and composition may be administered simultaneously or wholly or partially sequentially; when administered wholly or partially sequentially, either component may be administered first.

A therapeutically effective amount of a peptide compound of the presently disclosed inventive concepts refers to an amount which is effective in controlling, reducing, and/or inhibiting a bacterial and/or fungal infection. The term "controlling" is intended to refer to all processes wherein there may be a slowing, interrupting, arresting, and/or stopping of the progression of the infection and does not necessarily indicate a total elimination of the infection symptoms.

The term "therapeutically effective amount" is further meant to define an amount resulting in the improvement of any parameters or clinical symptoms characteristic of a bacterial and/or fungal infection. The actual dose will vary with the patient's overall condition, the seriousness of the symptoms, and counter indications. As used herein, the term "therapeutically effective amount" also means the total amount of each active component of the pharmaceutical composition or method that is sufficient to show a meaningful patient benefit, e.g., a reduction of bacterial and/or fungal infection and/or an improvement in wound and/or graft healing. When applied to an individual active ingredient that is administered alone, the term refers to that ingredient alone. When applied to a combination, the term refers to combined amounts of the active ingredients that result in the therapeutic effect, whether administered in combination, serially, and/or simultaneously.

A therapeutically effective amount of the peptide compound used in the treatment described herein can be determined by the attending diagnostician, as one skilled in the art, by the use of conventional techniques and by observing results obtained under analogous circumstances. In determining the therapeutically effective dose, a number of factors may be considered by the attending diagnostician, including, but not limited to: the species of the subject; its size, age, and general health; the specific bacterial or fungal disease or other condition involved; the degree of or involvement or the severity of the bacterial or fungal disease or other condition; the response of the individual subject; the particular compound administered; the mode of administration; the bioavailability characteristic of the preparation administered; the dose regimen selected; the use of concomitant medication; and other relevant circumstances. A therapeutically effective amount of a peptide compound of the presently disclosed inventive concepts also refers to an amount of the peptide compound which is effective in controlling or reducing the bacterial or fungal infection, or improving wound or graft healing, for example.

A therapeutically effective amount of a composition of the presently disclosed inventive concepts will generally contain sufficient active ingredient (i.e., the peptide compound) to deliver from about 0.1 µg/kg to about 100 mg/kg (weight of active ingredient/body weight of patient). Particularly, the composition will deliver about 0.5 µg/kg to about 50 mg/kg, and more particularly about 1 µg/kg to about 10 mg/kg.

Practice of the method of the presently disclosed inventive concepts may comprise administering to a subject a therapeutically effective amount of the peptide compound in any suitable systemic and/or local formulation, in an amount effective to deliver the dosages listed above. An effective, particular dosage of the peptide compound for substantially inhibiting the bacterial and/or fungal infection is about 1 µg/kg to about 10 mg/kg of the peptide. The dosage can be administered, for example but not by way of limitation, on a one-time basis, or administered at multiple times (for example but not by way of limitation, from one to five times per day, or once or twice per week), or continuously via a venous drip, depending on the desired therapeutic effect. In one non-limiting example of a therapeutic method of the presently disclosed inventive concepts, the peptide compound is provided in an IV infusion in the range of from about 1 mg/kg to about 10 mg/kg of body weight once a day.

In practicing the method of treatment or use of the presently disclosed inventive concepts, a therapeutically effective amount of the peptide compound is administered to a mammal having a bacterial and/or fungal disease state, and/or other condition desired to be treated (such as but not limited to, a wound or a graft). The peptide compound may be administered in accordance with the method of the presently disclosed inventive concepts either alone or in combination with other therapies.

Administration of the peptide compound used in the pharmaceutical composition or to practice the method of the presently disclosed inventive concepts can be carried out in a variety of conventional ways, such as, but not limited to, orally, by inhalation (e.g., for sinus fungal infections), rectally, or by cutaneous, subcutaneous, intraperitoneal, vaginal, or intravenous injection. Oral formulations may be formulated such that the peptide compound passes through a portion of the digestive system before being released, for example it may not be released until reaching the small intestine, or the colon.

When a therapeutically effective amount of the peptide compound is administered orally, the compound may be in the form of a tablet, capsule, powder, solution, or elixir. The pharmaceutical composition may additionally contain a solid carrier, such as a gelatin or an adjuvant. The tablet, capsule, and powder particularly contains from about 0.05 to about 95% of the peptide compound by dry weight. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol, or polyethylene glycol. When administered in liquid form, the pharmaceutical composition particularly contains from about 0.005 to about 95% by weight of peptide. For example, a dose of about 10 mg to about 1000 mg once or twice a day could be administered orally.

For oral administration, the peptide compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants, and inert fillers such as lactose, sucrose, and cornstarch, or the dosage forms can be sustained release preparations.

In another embodiment, the peptide compounds of the presently disclosed inventive concepts can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the peptide compound in an aqueous or non-aqueous pharmaceutically acceptable solvent which may also contain suspending agents, sweetening agents, flavoring agents, and preservative agents as are known in the art.

For parenteral administration, for example, the peptide compounds may be dissolved in a physiologically acceptable pharmaceutical carrier and administered as either a solution or a suspension. Non-limiting examples of suitable pharmaceutical carriers are water, saline, dextrose solutions, fructose solutions, ethanol, or oils of animal, vegetative, or synthetic origin. The pharmaceutical carrier may also contain preservatives and buffers as are known in the art.

When a therapeutically effective amount of the peptide compound is administered by intravenous, cutaneous, or subcutaneous injection, the peptide compound is particularly in the form of a pyrogen-free, parenterally acceptable aqueous solution or suspension. The preparation of such parenterally acceptable peptide solutions, having due regard to pH, isotonicity, stability, and the like, is well within the skill in the art. A particular pharmaceutical composition for intravenous, cutaneous, or subcutaneous injection may contain, in addition to the peptide compound, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the presently disclosed inventive concepts may also contain stabilizers, preservatives, buffers, antioxidants, or other additive(s) known to those of skill in the art.

As noted above, the compositions can also include an appropriate carrier. For topical use, any of the conventional excipients may be added to formulate the peptide compound into a lotion, ointment, powder, cream, spray, or aerosol. For surgical implantation, the peptide compound may be combined with any of the well-known biodegradable and bio-erodible carriers, such as polylactic acid and collagen formulations. Such materials may be in the form of solid implants, sutures, sponges, wound dressings, and the like. In any event, for local use of the materials, the peptide compound is usually present in the carrier or excipient in a weight ratio of from about 1:1000 to about 1:20,000, but is not limited to ratios within this range. Preparation of compositions for local use is detailed in *Remington: The Science and Practice of Pharmacy*, 21$^{st}$ed.

As noted, particular amounts and modes of administration can be determined by one skilled in the art. One skilled in the art of preparing formulations can readily select the proper form and mode of administration, depending upon the particular characteristics of the peptide compound selected, the infection to be treated, the stage of the infection, and other relevant circumstances using formulation technology known in the art, described, for example, in *Remington: The Science and Practice of Pharmacy*, 21$^{st}$ ed.

The pharmaceutical compositions of the presently disclosed inventive concepts can be manufactured utilizing techniques known in the art. Typically, the therapeutically effective amount of the peptide compound will be admixed with a pharmaceutically acceptable carrier.

The presently disclosed inventive concepts further includes (but is not limited to) a method of treating a topical bacterial or fungal infection by topically applying an amount of the composition sufficient to treat the infection, e.g., about 0.5% to about 10% by weight of the composition. The topical medication may take any number of standard forms such as pastes, gels, creams, and ointments. In one embodiment, a solution of the composition to be administered may be prepared using a solvent known to promote transdermal absorption, such as but not limited to, ethanol or dimethyl sulfoxide (DMSO) with or without other excipients. Particularly, topical administration may be accomplished using a patch either of the reservoir and porous membrane type or of a solid matrix variety.

The amount of the peptide compound in the pharmaceutical composition of the presently disclosed inventive concepts will depend upon the nature and severity of the condition being treated and on the nature of prior treatments which the patient has undergone. Ultimately, the attending physician will decide the amount of peptide compound with which to treat each individual patient. Initially, the attending physician may administer low doses of the peptide compound and observe the patient's response. Larger doses may be administered until the optimal therapeutic effect is obtained for the patient, and at that point the dosage is not increased further. Without wishing to be held to a specific dosage, it is contemplated that the various pharmaceutical compositions used to practice the method of the presently disclosed inventive concepts may contain, but are not limited to, about 0.1 mg to about 100 mg of the peptide compound per kg body weight per dose.

The duration of intravenous therapy using the pharmaceutical composition of the presently disclosed inventive concepts will vary, depending on the severity of the disease being treated and the condition and potential idiosyncratic response of each individual patient. It is contemplated that the duration of each application of the peptide compound may be in the range of about 1 to about 2 hours and given once about every 12 or 24 hours by continuous intravenous administration. Other antibiotics, intravenous fluids, and cardiovascular and respiratory support could also be provided if requested by the attending physician in a manner known to one of ordinary skill in the art.

Bacteria which may be treated by the peptide compounds of the presently disclosed inventive concepts include, but are not limited to, Gram negative bacteria such as but not limited to *Pseudomonas aeruginosa, Escherichia coli, Salmonella typhimurium* and *Acinetobacter baumannii*. Fungal infections which may be treated by the peptide compounds described herein include but are not limited to those caused by *Candida* spp., *Saccharomyces cerevisiae, Histoplasma capsulatum* and other *Histoplasma* species which cause histoplasmosis, *Aspergillus fumigatus* and other species (occurring mostly in the lung) which causes Aspergillosis, and *Cryptococcus neoformans* (sometimes found in the lung but mostly in the CNS), which causes a disease known as cryptococcosis.

Additional pharmaceutical methods may be employed to control the duration of action of the peptide compound. Increased half-life and/or controlled release preparations may be achieved through the use of polymers to conjugate, complex with, and/or absorb the peptide described herein. The controlled delivery and/or increased half-life may be achieved by selecting appropriate macromolecules (for example but not by way of limitation, polysaccharides, polyesters, polyamino acids, homopolymers polyvinyl pyrrolidone, ethylenevinylacetate, methylcellulose, or carboxymethylcellulose, and acrylamides such as N-(2-hydroxypropyl) methacrylamide), and the appropriate concentration of macromolecules as well as the methods of incorporation, in order to control release.

Another possible method useful in controlling the duration of action by controlled release preparations and half-life is incorporation of the peptide compound or its functional derivatives into particles of a polymeric material such as polyesters, polyamides, polyamino acids, hydrogels, poly (lactic acid), ethylene vinylacetate copolymers, copolymer micelles of, for example, PEG and poly(1-aspartamide).

It is also possible to entrap the peptide compounds in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles, and nano-capsules), or in macroemulsions. Such techniques are well known to persons having ordinary skill in the art.

When the peptide composition is to be used as an injectable material, it can be formulated into a conventional injectable carrier. Suitable carriers include biocompatible and pharmaceutically acceptable phosphate buffered saline solutions, which are particularly isotonic.

For reconstitution of a lyophilized product in accordance with the presently disclosed inventive concepts, one may employ a sterile diluent, which may contain materials generally recognized for approximating physiological conditions and/or as required by governmental regulation. In this respect, the sterile diluent may contain a buffering agent to obtain a physiologically acceptable pH, such as sodium chloride, saline, phosphate-buffered saline, and/or other substances which are physiologically acceptable and/or safe for use. In general, the material for intravenous injection in humans should conform to regulations established by the Food and Drug Administration, which are available to those in the field. The pharmaceutical composition may also be in the form of an aqueous solution containing many of the same substances as described above for the reconstitution of a lyophilized product.

The peptide compounds of the presently disclosed inventive concepts can also be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines, and substituted ethanolamines.

As mentioned above, the peptide compounds of the presently disclosed inventive concepts may be incorporated into pharmaceutical preparations which may be used for therapeutic purposes. However, the term "pharmaceutical preparation" is intended in a broader sense herein to include preparations containing a peptide composition in accordance with presently disclosed inventive concepts, used not only for therapeutic purposes but also for reagent or diagnostic purposes as known in the art. The pharmaceutical preparation intended for therapeutic use should contain a "pharmaceutically acceptable" or "therapeutically effective amount" of the peptide compound, i.e., that amount necessary for preventative or curative health measures. If the pharmaceutical preparation is to be employed as a reagent or diagnostic, then it should contain reagent or diagnostic amounts of the peptide compound.

Certain embodiments of the presently disclosed inventive concepts are directed to any of the compositions described herein above or otherwise contemplated herein, for use in any of the methods described herein above or otherwise contemplated herein.

All of the diagnostic and assay methods listed herein are well within the ability of one of ordinary skill in the art given the teachings provided herein.

EXAMPLES

The presently disclosed inventive concepts, having now been generally described, will be more readily understood by reference to the following examples and embodiments, which are included merely for purposes of illustration of certain aspects and embodiments of the presently disclosed inventive concepts, and are not intended to be limiting. The following detailed examples and methods describe how to make and use the various peptide compounds of the presently disclosed inventive concepts and are to be construed, as noted above, only as illustrative, and not limitations of the disclosure in any way whatsoever. Those skilled in the art will promptly recognize appropriate variations from the compounds and procedures.

Example 1

Antibacterial Activity of Peptide Compounds Based on Peptide 20-44 (SEQ ID NO:7) and Method of Enhancing Activity as well as Scale-Up Production of Compounds Based on Peptides 20-44, 95-122, and 120-146 (SEQ ID NOS:7, 26, and 28, respectively).

In certain embodiments, the presently disclosed inventive concepts include peptide compounds, and to compositions thereof, comprising oligopeptide derivatives comprising an amino acid sequence, and a solubilizing moiety. The oligopeptide derivative may be based on a CAP37 protein subsequence selected from, for example, amino acids 20-44 (SEQ ID NO:7), 23-42 (SEQ ID NO:14), 95-122 (SEQ ID NO:26), 102-122 (SEQ ID NO:27), and 120-146 (SEQ ID NO:28) of CAP37 protein.

In certain embodiments, the presently disclosed inventive concepts include compositions that contain oligopeptide derivatives (i.e., peptide compounds) that comprise an oligopeptide and a solubilizing moiety. The oligopeptide derivative/peptide compound is represented by Formula (I) below:

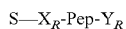

$$S-X_R\text{-Pep-}Y_R$$

wherein Pep is one of SEQ ID NOS:1-14, 25-31, and 47 (see, for example, Table 1) or another appropriate amino acid sequence described herein; $X_R$ and $Y_R$ are each independently 0, 1, 2, 3, 4, 5, or 6 arginine residues, with the proviso that $(X_R+Y_R)$ is 4, 5, or 6 arginine residues; and S is a solubilizing moiety comprising 1-10 subunits having the formula: $NH_nCH_2CH_2-(OCH_2CH_2)_p-O(CR_1R_2)_qCO-$, wherein q=0, 1, 2, 3, or 4 and p=1, 2, 3, 4, 5, 6, 7, or 8, $R_1$ and $R_2$ are selected from the group consisting of H, $CH_3$ and $CH_2CH_3$, and n=1 or 2; and with the proviso that S comprises at least one subunit which is not AEEA or AEEEA.

In one non-limiting embodiment, S is from 1-10 AEEP and/or AEEEP subunits or any other solubilizing subunit disclosed herein linked in any subcombination or order.

As stated herein above, $X_R$ and $Y_R$ are each independently 0, 1, 2, 3, 4, 5, or 6 arginine residues, with the proviso that $(X_R+Y_R)$ is 4, 5, or 6 arginine residues. By way of example, Table 2 below lists the various combinations of $X_R$ and $Y_R$ groups that may be utilized in accordance with Formula (I). The amino acid sequence RRRR disclosed in Table 2 has been assigned SEQ ID NO:15 herein, whereas the amino acid sequences RRRRR and RRRRRR have been assigned SEQ ID NOS:16 and 17, respectively. In one non-limiting example, $X_R$ includes four arginine residues, while $Y_R$ is one arginine residue.

When the peptide compound comprises two cysteines (e.g., SEQ ID NO:7 or 14), the oligopeptide may be cyclized via linkage between the two cysteine residues therein.

TABLE 1

| SEQ ID NO: | Sequence | Compound Name |
|---|---|---|
| | Pep Sequences in Accordance with Formula (I) (5-$X_R$-Pep-$Y_R$) | |
| 1 | NQGRHFSGGALIHARFVMTAASCFQ | BCC02 (20-44$_{ser26}$) |
| 2 | NQGRHFTGGALIHARFVMTAASCFQ | 20-44$_{thr26}$ |
| 3 | NQGRHFMGGALIHARFVMTAASCFQ | 20-44$_{met26}$ |
| 4 | NQGRHFCGGALIHARFVMTAASSFQ | BCC03 (20-44$_{ser42}$) |
| 5 | NQGRHFCGGALIHARFVMTAASTFQ | 20-44$_{thr42}$ |
| 6 | NQGRHFCGGALIHARFVMTAASMFQ | 20-44$_{met42}$ |
| 7 | NQGRHFCGGALIHARFVMTAASCFQ | BCC01 (20-44) |
| 8 | RHFSGGALIHARFVMTAASC | 23-42$_{ser26}$ |
| 9 | RHFTGGALIHARFVMTAASC | 23-42$_{thr26}$ |
| 10 | RHFMGGALIHARFVMTAASC | 23-42$_{met26}$ |
| 11 | RHFCGGALIHARFVMTAASS | 23-42$_{ser42}$ |
| 12 | RHFCGGALIHARFVMTAAST | 23-42$_{thr42}$ |
| 13 | RHFCGGALIHARFVMTAASM | 23-42$_{met42}$ |
| 14 | RHFCGGALIHARFVMTAASC | 23-42 |
| | Peptide Backbones ($X_R$-Pep-$Y_R$) in Accordance with Formula (I): | |
| 18 | RRRRNQGRHFSGGALIHARFVMTAASCFQR | BCC02-5R (20-44$_{ser26}$) |
| 19 | RRRRNQGRHFCGGALIHARFVMTAASSFQR | BCC03-5R (20-44$_{ser42}$) |
| 20 | RRRRNQGRHFCGGALIHARFVMTAASCFQR | BCC01-5R (20-44$_{cys}$) |
| | Peptide Compound (S-XR-Pep-$Y_R$) Sequences in Accordance with Formula (I): | |
| 21 | (AEEP)-(AEEP)-RRRRNQGRHFSGGALIHARFVMTAASCFQR | BCC02-5RMP |
| 22 | (AEEP)-(AEEP)-RRRRNQGRHFCGGALIHARFVMTAASSFQR | BCC03-5RMP |
| 23 | (AEEP)-(AEEP)-RRRRNQGRHFCGGALIHARFVMTAASCFQR | BCC01-5RMP |
| 24 | (AEEP)-(AEEP)-NQGRHFCGGALIHARFVMTAASSFQ | BCC03-MP |
| | Peptides Based on Listed AA's of CAP37 | |
| 26 | LDREANLTSSVTILPLPLQNATVEAGTR | 95-122 |
| 27 | TSSVTILPLPLQNATVEAGTR | 102-122 |
| 28 | GTRCQVAGWGSQRSGGRLSRFPRFVNV | 120-146QR |
| 29 | GTRCQVAGWGSQHSGGRLSRFPRFVNV | 120-146QH |
| 30 | GTRCQVAGWGSWRSGGRLSRFPRFVNV | 120-146WR |
| 31 | GTRCQVAGWGSWHSGGRLSRFPRFVNV | 120-146WH |
| | Peptide Compound (S-$X_R$-Pep-$Y_R$) Sequences in Accordance with Formula (I): | |
| 32 | (AEEP)-(AEEP)-RRRRGTRCQVAGWGSQRSGGRLSRFPRFVNVR | 120-146QR-5RMP$_{AEEP}$ |
| 33 | (AEEP)-(AEEP)-RRRRGTRCQVAGWGSQHSGGRLSRFPRFVNVR | 120-146QH-5RMP$_{AEEP}$ |
| 34 | (AEEP)-(AEEP)-RRRRGTRCQVAGWGSWRSGGRLSRFPRFVNVR | 120-146WR-5RMP$_{AEEP}$ |
| 35 | (AEEP)-(AEEP)-RRRRGTRCQVAGWGSWHSGGRLSRFPRFVNVR | 120-146WH-5RMP$_{AEEP}$ |
| 36 | (AEEP)-(AEEP)-RRRRNQGREIFTGGALIHARFVMTAASCFQR | 20-44$_{thr26}$-5RMP |
| 37 | (AEEP)-(AEEP)-RRRRNQGRHFMGGALIHARFVMTAASCFQR | 20-44$_{met26}$-5RMP |
| 38 | (AEEP)-(AEEP)-RRRRNQGRHFCGGALIHARFVMTAASTFQR | 20-44$_{thr42}$-5RMP |
| 39 | (AEEP)-(AEEP)-RRRRNQGRHFCGGALIHARFVMTAASMFQR | 20-44$_{met42}$-5RMP |
| 40 | (AEEP)-(AEEP)-RRRRRHFSGGALIHARFVMTAASCR | 23-42$_{ser26}$-5RMP |
| 41 | (AEEP)-(AEEP)-RRRRRHFTGGALIHARFVMTAASCR | 23-42$_{thr26}$-5RMP |
| 42 | (AEEP)-(AEEP)-RRRRRHFMGGALIHARFVMTAASCR | 23-42$_{met26}$-5RMP |
| 43 | (AEEP)-(AEEP)-RRRRRHFCGGALIHARFVMTAASSR | 23-42$_{ser42}$-5RMP |
| 44 | (AEEP)-(AEEP)-RRRRRHFCGGALIHARFVMTAASTR | 23-42$_{thr42}$-5RMP |
| 45 | (AEEP)-(AEEP)-RRRRRHFCGGALIHARFVMTAASMR | 23-42$_{met42}$-5RMP |
| 46 | (AEEP)-(AEEP)-RRRRLDREANLTSSVTILPLPLQNATVEAGTRR | 95-122-5RMP$_{AEEP}$ |
| 48 | (AEEA)-(AEEA)-RRRRLDREANLTSSVTILPLPLQNATVEAGTRR | 95-122-5RMP$_{AEEA}$ |
| 49 | (AEEP)-(AEEP)-RRRRTSSVTILPLPLQNATVEAGTRR | 102-122-5RMP$_{AEEP}$ |
| 50 | (AEEA)-(AEEA)-RRRRTSSVTILPLPLQNATVEAGTRR | 102-122-5RMP$_{AEEA}$ |
| 51 | (AEEA)-(AEEA)-RRRRGTRCQVAGWGSWHSGGRLSRFPRFVNVR | 120-146WH-5RMP$_{AEEA}$ |

TABLE 2

Examples of Possible $X_R$, $Y_R$ Combinations in Formula (I) (S-$X_R$-Pep-$Y_R$)

| $X_R$, $Y_R$ Combination Number | $X_R$ | $Y_R$ |
|---|---|---|
| 1 | | RRRR |
| 2 | R | RRR |
| 3 | RR | RR |
| 4 | RRR | R |
| 5 | RRRR | |
| 6 | | RRRRR |
| 7 | R | RRRR |
| 8 | RR | RRR |
| 9 | RRR | RR |
| 10 | RRRR | R |
| 11 | RRRRR | |
| 12 | | RRRRRR |
| 13 | R | RRRRR |
| 14 | RR | RRRR |
| 15 | RRR | RRR |
| 16 | RRRR | RR |
| 17 | RRRRR | R |
| 18 | RRRRRR | |

The amino acid sequences RRRR, RRRRR, and RRRRRR have been assigned SEQ ID NOS: 15, 16, and 17, respectively.

The peptide compounds of the presently disclosed inventive concepts can be used, in at least one embodiment, for the treatment of severe Gram negative infections which include, but are not limited to, *Pseudomonas aeruginosa*, *Salmonella typhimurium*, *Acinetobacter* sp., and *E. coli*. These organisms are capable of causing fatal hospital-acquired infections and are rapidly gaining resistance to current antibiotic therapies. Although the peptide comprising amino acids 20-44 of CAP37 (SEQ ID NO:7) has strong antibacterial activity, it is difficult to produce on a commercial scale, in part because of poor solubility. Using the previously established methodology to scale-up this peptide in sufficient quantity and purity was unsuccessful. Substantial research and experimentation, including numerous technical approaches, combinations of amino acids, synthesis procedures, and purifications, were necessary to eventually arrive at the novel active peptide compounds described herein that can be produced in a commercial scale-up procedure and thus can be used clinically. Among the novel features of the peptide compounds described herein are increased solubility, increased bactericidal efficacy, reduced aggregation, improved synthesis, scalability, and increased purity.

The novel peptide compounds, which are derivatized versions of the native 20-44 peptide, retain substantially all other activities of the native 20-44 peptide sequence, for example, strong antibacterial activity, the ability to bind and neutralize lipopolysaccharide (LPS), and negligible cytotoxicity against mammalian cells.

The production of cationic antibacterial peptides which are active against bacteria, exhibit low toxicity to mammalian cells, and that can be scaled up at a cost of goods that make them commercially viable has eluded most others working in the field. Further, purification can be challenging due to aggregation. However, the novel peptide compounds described herein have increased solubility, which will greatly facilitate their purification and antibacterial activity.

Other advantages of certain of the novel peptide compounds described herein include, but are not limited to: (1) their ability to kill clinical isolates that have numerous antibiotic resistant patterns; and (2) their bacterial kill rate (for example within minutes) is much quicker than traditional antibiotics.

The path to scale-up was challenging and not straightforward. Although synthesis of the CAP37 antibiotic peptides in an academic small-scale setting was successful, this approach was not easily transferable to scale-up production. The major issue appeared to be aggregation.

In the initial stages of the work leading to the presently disclosed inventive concepts, sequential addition of amino acids was used to make the peptides. Three candidate peptides (CAP37$_{20-44}$ (SEQ ID NO:7), CAP37$_{20-44ser26}$ (SEQ ID NO:1), and CAP37$_{20-44ser42}$ (SEQ ID NO:4)) were synthesized. All three peptides made by this mode of synthesis were relatively insoluble. Based on these results, work was focused on production of one peptide at a time, and CAP37$_{20-44ser42}$ was selected. In one embodiment, a fragment Fmoc condensation strategy was used rather than sequential addition of amino acids. In the fragment condensation method, three small fragments were made and condensed together to form a CAP37$_{20-44ser42}$ amino acid sequence (SEQ ID NO:4). The rationale behind this reasoning was that three small fragments could be synthesized in a highly purified form and linked together, thereby overcoming some of the aggregation problems. The product from this synthesis was dialyzed against 1% acetic acid and lyophilized and determined to be approximately 50% pure. Antimicrobial activity of this peptide was approximately half of what was normally obtained. In one embodiment, the dialysis procedure was changed to employ a dilute tri-fluoro acetic acid (TFA) solution (e.g., 0.1%), which obtained a product with stronger antimicrobial activity and greater purity (about 80%). In the next production, a cysteine residue was used that was protected during synthesis and then de-protected in the final stages of purification, in an attempt to improve stability.

Eventually, 20 grams of each compound was produced; however, the major technical issues of aggregation and solubility, although overcome to a large degree, still remained, thus indicating that large scale production for clinical trials may not be feasible. After many trials and experiments, the idea of adding a plurality of arginine (R) residues at the COOH-terminus and/or the NH$_2$-terminus of the peptide was discovered. In the first iteration, three R residues were added, one at the COOH-terminus and two at the NH$_2$ terminus. The effect on solubility and activity by using arginine residues was markedly improved. Based on this successful result, each of the three sequences was synthesized as a peptide backbone having a total of five arginine residues (e.g., one at the COOH-terminus and four at the NH$_2$-terminus, e.g., see SEQ ID NOS:18-20 in Table 1). Scale-up of the compounds was successful, enabling synthesis of gram quantities of each peptide. Moreover, the in vitro antibacterial activity was significantly greater than what had been previously observed with the original peptides. The three 5-arginine peptides showed >97% kill at concentrations as low as 2.5 µM, which is 10-fold higher than what had been observed previously. All three 5-arginine peptides (SEQ ID NOS:18-20) also showed potent activity against other Gram negative organisms including *Escherichia coli* and *Salmonella typhimurium*. Due to the increased potency of these newly synthesized peptides, it was queried whether the peptides may have cytotoxicity on mammalian cells. The peptides were evaluated using the Lactic Dehydrogenase Cytotoxicity Detection kit (Roche Diagnostics Corp., Indianapolis, Ind.), and it was found that the peptides had minimal cytotoxic activity even at the highest concentrations tested (75 µM). After 4 hours incubation, all three peptides showed <4% cytotoxicity. After 24 hours incubation, there was a slight increase in cytotoxicity levels; peptide 20-44$_{ser26}$ (SEQ ID NO:18) showed 23%, 20-44$_{ser42}$ (SEQ ID NO:19) showed 5%, and 20-44$_{cys}$ (SEQ ID NO:20) showed 10% activity.

All three 5-arginine peptides (SEQ ID NOS:18-20) bound *Pseudomonas* LPS, as measured by the Limulus Amebocyte Lysate (LAL) assay. However, it had not been demonstrated that these peptides could neutralize the toxic effects of LPS. The well-characterized response of RAW264.7 macrophage cells was used to produce tumor necrosis-factor-alpha (TNF-α) in response to LPS to determine whether the peptides could dampen the release of this cytokine. All three 5-arginine peptides attenuated the release of TNF-α in response to *Pseudomonas* LPS; and this result was dose dependent. Importantly, pre-treatment (3 hours prior to LPS addition) as well as post-treatment of the RAW264.7 cells (3 hours post LPS addition) with peptide dampened the cytokine release. A control peptide was unable to attenuate the release of TNF-α. Further studies showed that this attenuation was most likely due to blocking of the activity of the transcription factor nuclear factor—kappa B (NF-κB). The finding that the novel peptides bind and neutralize the effect of *Pseudomonas* LPS is of critical importance since this ensures that the novel therapeutic peptide compounds described herein will not only kill the bacteria, but will also neutralize the LPS endotoxin released by the bacteria which plays such an important role in the rapid progression of sepsis.

When the arginines were linked to the peptide to form the peptide backbone (SEQ ID NOS:18-20), there was marked increase in solubility of the peptides and very potent activity (capable of reducing bacterial load from 1×10⁶ CFU/ml to 1×10 CFU/ml, a 5 log reduction). However, although these peptides (SEQ ID NOS:18-20) were highly potent, they could not be purified beyond about 70% purity. Much time and experimental effort was spent in the laboratory exploring purification techniques, but yield and purity could not be increased beyond about 70%. This was extremely disappointing, since a large number of in vitro LPS binding experiments and bactericidal studies had been performed to demonstrate efficacy. Finally, after extensive additional experimentation, another solubilizing moiety was added to the peptides, and this addition increased half-life, solubility, and purity of the peptides. In this embodiment, the solubilizing moiety comprised a pair of small ("mini") PEG molecules AEEP, each having a molecular weight of about 160.

The two PEG solubilizing moieties comprising AEEP were linked end-to-end to the amino terminal end of the peptide backbone. Table 1 shows the three peptide compounds comprising two AEEP molecules linked to each of SEQ ID NO:18, SEQ ID NO:19, and SEQ ID NO:20 and designated therein by the compound names BCC002-5RMP (SEQ ID NO:21), BCC03-5RMP (SEQ ID NO:22), and BCC01-5RMP (SEQ ID NO:23), respectively. In these 3 peptide compounds (referring to Formula (I) described above), S is AEEP-AEEP, $X_R$ is RRRR (SEQ ID NO:15), $Y_R$ is R, and Pep is SEQ ID NO:1, SEQ ID NO:4, and SEQ ID NO:7, respectively.

Purity of these peptides with the 5 arginines and the two AEEA moieties range consistently from 96.12% to 98.62%. Good laboratory practice (GLP) grade peptide synthesis has been achieved with BCC002-5RMP (SEQ ID NO: 21), and 75 grams of peptide have been synthesized at 97.24% purity.

In addition to peptides based on the 20-44 sequence (SEQ ID NO: 21 to SEQ ID NO: 23), the inclusion of the five arginine residues and the two small PEG (AEEP) molecules during the synthesis of the peptides based on amino acids 95-122 (SEQ ID NO: 26 and SEQ ID NO: 27) and 120-146 (SEQ ID NOS: 32-35) will aid in the overall scale-up of these peptides as well.

In vitro bactericidal activity: The three peptide compounds BCC01-5RMP (SEQ ID NO:23), BCC002-5RMP (SEQ ID NO:21), and BCC003-5RMP (SEQ ID NO:22) were assayed for in vitro bactericidal activity against *Pseudomonas aeruginosa, Escherichia coli, Salmonella typhimurium*, and *Acinetobacter baumannii*. The starting inoculum for all experiments was 1×10⁶ colony forming units (CFU)/ml. The CFU remaining at the end of 60 to 180 minute incubation was determined, and the data plotted as a log reduction in CFU/ml. The peptides were most active against *Pseudomonas* and *Acinetobacter* with strong, but lesser activity against *Salmonella* and *E. coli*. Table 3 shows activity of the compounds against *Pseudomonas*. The in vitro bactericidal activity shown in Table 3 indicates that BCC003-5RMP (SEQ ID NO:22) has a slight edge over the other two peptides in this assessment.

TABLE 3

| | *P. aeruginosa* ATCC 27853% kill | | | |
|---|---|---|---|---|
| Peptide concentration | Experiment #1 | Experiment #2 | Experiment #3 | Experiment #4 |
| BCC02-5RMP (SEQ ID NO: 21 ) | | | | |
| 50 µg/ml | 100 | 100 | 100 | 100 |
| 25 µg/ml | 100 | 99.98 | 100 | 100 |
| 12.5 µg/ml | 98.21 | 90.78 | 99.93 | 99.96 |
| 6.25 µg/ml | Not done | Not done | 98.85 | 99.26 |
| BCCO3-5RMP (SEQ ID NO: 22) | | | | |
| 50 µg/ml | 100 | Not done | Not done | Not done |
| 25 µg/ml | 100 | 100 | 100 | 100 |
| 12.5 µg/ml | 99.91 | 99.98 | 100 | 99.56 |
| 6.25 µg/ml | Not done | 99.34 | 99.93 | 98.32 |
| | Experiment #1 | | | |
| BCC01-5RMP (SEQ ID NO: 23) | | | | |
| 50 µg/ml | 100 | | | |
| 25 µg/ml | 99.83 | | | |
| 12.5 µg/ml | 79.21 | | | |

Tables 4-6 show the results of various peptides and peptide compounds against *P. aeruginosa*. Table 4 shows the results of an investigation of the effects of peptide or peptide compounds BCC01-5R (SEQ ID NO: 20), BCC01-5RMP (SEQ ID NO: 23), BCC002-5R (SEQ ID NO: 18), BCC002-5RMP (SEQ ID NO: 21), BCC003-5R (SEQ ID NO: 19), BCC003-5RMP (SEQ ID NO:22), and BCC003-MP (SEQ ID NO:24) against *P. aeruginosa* ATCC® strain 27853™ (American Type Culture Collection, Manassas, Va.). A comparison of activity BCC003-5R (SEQ ID NO: 19) and BCC003-5RMP (SEQ ID NO: 22), the two peptide compounds with the additional five arginine residues versus BCC003-MP (SEQ ID NO: 24) (i.e., the peptide SEQ ID NO:4 which has the solubilizing moiety S attached thereto but does not have the five additional R residues) shows that the inclusion of the 5 arginines enhance bactericidal activity. Table 4 further compares the activity of several other compounds, including the "5R" versions of BCC01, i.e., SEQ ID NO:20 (which comprises SEQ ID NO: 7 with five additional arginines), the "5R" version of BCC002 (i.e., SEQ ID NO:18, which comprises SEQ ID NO: 1 with five additional arginines), and the 5RMP versions of BCC01 (SEQ ID NO: 23) and BCC002 (SEQ ID NO: 21). The data generally indicate the superiority of BCC003-5RMP (SEQ ID NO:22) and BCC002-5RMP (SEQ ID NO: 21) and the superiority of the 5R or 5RMP versions of the peptide over the "AEEP only" peptide against *P. aeruginosa*. Table 5 shows the strong activity of BCC003-5RMP (SEQ ID NO: 22) against a number of clinical isolates of *Pseudomonas* obtained from infected skin wounds with various antibiotic resistant profiles. Table 6 shows the strong in vitro bactericidal activity of BCC002-5RMP (SEQ ID NO: 21) against clinical isolates of *Pseudomonas aeruginosa* obtained from patients with bacterial keratitis.

In vivo bactericidal activity of BCC002-5RMP (SEQ ID NO:21): FIG. 1 shows results of the use of BCC002-5RMP (SEQ ID NO:21) in vivo in a bacterial keratitis model in C57/BL6 mice. A circular wound (2 mm) was created on the mouse cornea by removing the epithelium and infecting the wound with $10^5$ CFU of *P. aeruginosa* (ATCC® 27853™ (American Type Culture Collection, Manassas, Va.)). Infected wounds were treated with saline or saline containing indicated concentrations of peptide every 15 minutes for 2 hours, then every 30 minutes for 3 hours on the first day. Infected wounds were treated twice on the second day and once on the third day. Mice were killed at 48 hours post-infection, and the colony forming units per eye (CFU/eye) were quantified. The means are plotted and are representative of 5 to 9 mice per group. Mann Whitney test was performed for each group as compared to the saline control group. The peptide compound effectively killed all bacteria and cured the infection at concentrations ranging between 0.25 and 0.75 mg/ml.

TABLE 4

Percent Kill and Log Reduction

| | BCC01 | | | | BCC02 | | | |
|---|---|---|---|---|---|---|---|---|
| | BCC01 5R Lot #026C09 SEQ ID NO: 20 *Pseudomonas aeruginosa* | | BCC01 5R MP Lot #J918 SEQ ID NO: 23 *Pseudomonas aeruginosa* | | BCC02 5R Lot #028C09 SEQ ID NO: 18 *Pseudomonas aeruginosa* | | BCC02 5R MP Lot #J880 SEQ ID NO: 21 *Pseudomonas aeruginosa* | |
| Peptide | ATCC 27853 | | ATCC 27853 | | ATCC 27853 | | ATCC 27853 | |
| Concentration µg/mL | Percent Kill | Log Reduction | Percent Kill | Log Reduction | Percent Kill | Log Reduction | Percent Kill | Log Reduction |
| 400 | | | | | | | | |
| 200 | | | | | | | | |
| 100 | | | | | | | | |
| 87.6 | 100.0 | 2.4 | | | 100.0 | 2.4 | | |
| 50 | | | 100.0 | 5.5 | | | 100.0 | 6.5 |
| 25 | | | 99.8 | 3.0 | | | 100.0 | 6.0 |
| 12.5 | | | 79.2 | 0.5 | | | 100.0 | 3.0 |
| 8.76 | 99.5 | 1.8 | | | 99.6 | 1.8 | | |
| 6.25 | | | | | | | 99.3 | 1.5 |
| 3.125 | | | | | | | | |
| 2.19 | 87.9 | 0.4 | | | 87.0 | 0.8 | | |
| 1.56 | | | | | | | | |
| 0.78 | | | | | | | | |
| 0.5475 | 63.2 | 0.0 | | | 75.6 | 0.1 | | |
| 0.137 | 25.4 | −0.3 | | | 24.9 | −0.3 | | |

| | BCC03 | | | | | |
|---|---|---|---|---|---|---|
| | BCC03 5R Lot #027C09 SEQ ID NO: 19 *Pseudomonas aeruginosa* | | BCC03 5R MP Lot #J971 SEQ ID NO: 22 *Pseudomonas aeruginosa* | | BCC03 MP Lot #130L09 SEQ ID NO: 24 *Pseudomonas aeruginosa* | |
| Peptide | ATCC 27853 | | ATCC 27853 | | ATCC 27853 | |
| Concentration µg/mL | Percent Kill | Log Reduction | Percent Kill | Log Reduction | Percent Kill | Log Reduction |
| 400 | | | | | 92.8 | 0.4 |
| 200 | 100.0 | 3.1 | | | 74.4 | −0.1 |
| 100 | 100.0 | 3.1 | | | 44.0 | −0.3 |
| 87.6 | 100.0 | 2.4 | | | | |
| 50 | 100.0 | 3.1 | | | −2.9 | −0.4 |
| 25 | 100.0 | 3.1 | 100.0 | 7.0 | −27.3 | −0.5 |
| 12.5 | 100.0 | 3.1 | 100.0 | 5.0 | −45.6 | −0.5 |
| 8.76 | 99.1 | 1.4 | | | | |
| 6.25 | 100.0 | 3.1 | 99.93 | 2.5 | −38.2 | −0.5 |
| 3.125 | | | | | | |

TABLE 4-continued

| Percent Kill and Log Reduction | | |
|---|---|---|
| 2.19 | *77.1* | *0.2* |
| 1.56 | | |
| 0.78 | | |
| 0.5475 | *65.1* | *0.0* |
| 0.137 | *33.8* | *-0.2* |

$5*10^3$ CFU/ml unless Italicized = $1*10^6$ CFU/ml

TABLE 5

| | Pseudomonas aeruginosa clinical isolates from infected skin wounds | | | | | | | |
|---|---|---|---|---|---|---|---|---|
| | Isolate #97-1 | | Isolate #98-1 | | Isolate #99-1 | | Isolate #100-1 | |
| | BCC03-5RMP (SEQ ID NO: 22) | | | | | | | |
| Peptide concentration | Expt #1 | Expt #2 | Expt #1 | Expt #2 | Expt #1 | Expt #2 | Expt #1 | Expt #2 |
| 25 µg/ml | 99.99 | 100 | 99.42 | 100 | 100 | 100 | 100 | 100 |
| 12.5 µg/ml | 99.66 | 100 | 98.47 | 99.99 | 100 | 100 | 99.98 | 99.99 |

TABLE 6

| | Pseudomonas aeruginosa clinical isolates from bacterialkeratitis patients | | | | | | | | | |
|---|---|---|---|---|---|---|---|---|---|---|
| | Isolate #5 | | | Isolate #6 | | | Isolate #18 | | | Isolate #46 |
| Peptide | BCC02 5RMP (SEQ ID NO: 21) | | | | | | | | | |
| concentra- | Expt # | | | Expt # | | | Expt # | | | Expt # |
| tion | 1 | 2 | 3 | 1 | 2 | 3 | 1 | 2 | 3 | 1 |
| 25 µg/ml | 100 | 99.99 | 100 | 100 | 100 | 100 | 100 | 100 | 100 | 100 |
| 12.5 µg/ml | 99.97 | 99.77 | 99.91 | 100 | 99.1 | 99.98 | 100 | 99.88 | 99.99 | 100 |

| | Pseudomonas aeruginosa clinical isolates frombacterialkeratitis patients | | | | | | | |
|---|---|---|---|---|---|---|---|---|
| | Isolate #46 | | Isolate #47 | | | Isolate #67 | | |
| Peptide | BCC02 5RMP (SEQ ID NO: 21) | | | | | | | |
| concentra- | Expt # | | Expt # | | | Expt # | | |
| tion | 2 | 3 | 1 | 2 | 3 | 1 | 2 | 3 |
| 25 µg/ml | 100 | 100 | 100 | 100 | 100 | 100 | 99.99 | 100 |
| 12.5 µg/ml | 99.95 | 99.99 | 99.9 | 99.76 | 99.97 | 99.99 | 99.55 | 99.64 |

Example 2: In Vitro LPS Binding and Neutralization

BCC01-5RMP (SEQ ID NO:23), BCC002-5RMP (SEQ ID NO:21), and BCC003-5RMP (SEQ ID NO:22) were tested for their ability to bind lipopolysaccharide (LPS) using the limulus amebocyte lysate method (LAL). All three peptides bound Pseudomonas LPS. There was no statistical difference in their ability to bind LPS using the LAL technique. The ability of the peptides to neutralize LPS was assessed by determining their ability to attenuate the release of tumor necrosis factor-alpha (TNF-α) from LPS-stimulated RAW264.7 cells (a mouse macrophage cell line). All three peptides were seen to attenuate the release of TNF-α. No significant differences were observed between the three peptides to neutralize LPS as measured by cytokine release. Peptides based on sequence 120-146 (SEQ ID NOS:28-31) also bind and neutralize Pseudomonas LPS.

Example 3: Synthesis and Purification of BCC003-5RMP

The purpose of this synthesis was to synthesize the peptide BCC003-5R (SEQ ID NO:19) and couple it to two small PEG molecules (AEEP) to produce BCC003-5RMP (SEQ ID NO:22): (AEEP)-(AEEP)-RRRRNQGRHFCG-GALIHARFVMTAASSFQR. After the synthesis, the peptide compound was purified and lyophilized. As noted previously, in the compound name BCC003-5RMP, "R" refers to arginine and "MP" refers to a solubilizing group S made up of two AEEP moieties.

Synthesis: The peptide compound may be synthesized using solid phase peptide synthesis using Fmoc chemistry protocol. The peptide chain was synthesized on Fmoc-Arg (Pbf)-Wang resin. Three equivalents of amino acids were used for each coupling, and couplings were performed using the DIC/HOBT method. After complete synthesis of the peptide chain, both Fmoc-mini-PEG™s were coupled by the DIC/HOBT method. After the synthesis, the resin was washed and dried.

The peptide compound was deprotected and cleaved from the resin using a cocktail of TFA-containing scavengers. Resin was filtered off, and filtrate was evaporated on an evaporator to remove TFA. The peptide compound was precipitated with ether; precipitate was filtrated off and dried under reduced pressure to get crude peptide.

Purification: The purification may be performed by RP-HPLC using the YMC ODS Gel C18 as support. 0.1% TFA/H$_2$O and acetonitrile were used as solvents for purification. The fractions were checked by analytical HPLC, and fractions with required purity were pooled together. The pool was evaporated and lyophilized. Purity of peptides generated using this technique was consistently >95%.

In other embodiments of the presently disclosed inventive concepts, the peptide compounds comprise derivatives of other amino acid portions of the CAP37 protein, including, but not limited to, peptides 23-42, 95-122, 102-122, and 120-146 which have been derivatized with substitutions (e.g., at positions 131 and/or 132), and/or with N- and/or C-terminal arginine residues and small PEG molecules as described elsewhere herein, such as in Formula (I) and Table 1 and accompanying description elsewhere herein. Such peptides 23-42, 95-122, 102-122, and 120-146 of CAP37 protein are described for example in U.S. Pat. Nos. 5,107,460; 7,354,900; and 7,893,027; which are hereby expressly incorporated by reference herein in their entireties.

The "Pep" sequence of the Formula (I) peptide compound described herein may comprise the following sequence (SEQ ID NO:25):

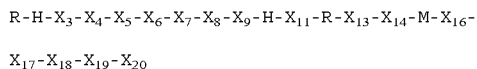

wherein $X_3$ and $X_{13}$ are phenylalanine, tyrosine, arginine, lysine or histidine; $X_4$ is selected from cysteine, serine, threonine, and methionine; $X_5$ and $X_6$ are selected from glycine and alanine; $X_7$, $X_{11}$, and $X_{14}$ are selected from alanine, leucine, isoleucine, and valine; $X_9$, $X_{17}$, and $X_{18}$ are selected from alanine, leucine, isoleucine, and valine; $X_{16}$ is selected from serine, threonine, and methionine; $X_{19}$ is selected from serine, threonine and methionine; $X_{20}$ is selected from cysteine, serine, and methionine; R is arginine; H is histidine; and M is methionine. This sequence is a derivative of SEQ ID NO:14 (i.e., amino acids 23-42 of CAP37 protein).

Similarly, the "Pep" sequence of the Formula (I) peptide compound described herein may comprise the following sequence (SEQ ID NO:47):

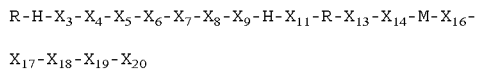

wherein $X_3$ and $X_{13}$ are phenylalanine, tyrosine, arginine, lysine, or histidine; $X_4$ is selected from cysteine, serine, threonine, and methionine; $X_5$ and $X_6$ are selected from glycine and alanine; $X_7$, $X_{11}$, and $X_{14}$ are selected from alanine, leucine, isoleucine, and valine; $X_9$, $X_{17}$, and $X_{18}$ are selected from alanine, leucine, isoleucine, and valine; $X_{16}$ is selected from serine, threonine, and methionine; $X_{19}$ is selected from serine, threonine, and methionine; $X_{20}$ is selected from cysteine, serine, threonine, and methionine; R is arginine; H is histidine; and M is methionine.

Example 4

Chemotactic and Wound Healing Activity of 95-122-Based (SEQ ID NOS:26-27, 46, 48-50) and 120-146-Based (SEQ ID NOS:28-35) Peptide Compounds.

In one embodiment, certain peptide compounds disclosed herein including those comprising SEQ ID NOS:26-35 have chemotactic activity for host cells including monocytes and corneal epithelial cells. For example, peptide 95-122 is shown herein to promote corneal wound healing in an in vivo mouse model of corneal epithelial abrasion and dermal skin wound healing in swine. Peptide compounds based on peptide 120-146 of CAP37 protein also have bacterial activity as well as immune regulation of host cells. Non-limiting examples of such peptide compounds are described below and are listed in Table 1 (see SEQ ID NOS:26-35).

Peptide compounds of the presently disclosed inventive concepts, such as but not limited to those mentioned below, can be used as therapeutics in aiding the rapid healing of wounds. Although antibiotics exist that can be used to treat infected wounds, none of these agents has been shown to both kill bacteria and accelerate wound healing and/or improve skin graft acceptance. Peptide compounds such as those described herein that can do both will have a great benefit medically and thus have strong commercial potential. Among the types of wounds that can be treated using these peptide compounds include, but are not limited to, chronic "non-healing" wounds such as diabetic ulcers, "bed sores," burns patients, infected psoriasis lesions, "dry eye" inflammatory conditions, as well as acute wounds such as ocular ulcers, ocular wounds, and wounds of skin and epithelial tissues. As noted, another function of the peptide compounds is promotion of the healing and acceptance of grafts such as skin grafts.

Peptides 95-122 and 102-122: Peptide 95-122 (LDREANLTSSVTILPLPLQNATVEA GTR; SEQ ID NO:26) corresponds to amino acids 95-122 of CAP37 protein. Peptide 102-122 (TSSVTILPLPLQNATVEAGTR; SEQ ID NO:27) is a truncation of Peptide 95-122 and corresponds to amino acids 102-122 of CAP37 protein. These peptides and derivatives thereof can be used in therapeutically-effective amounts to, for example, increase proliferation and migration of corneal epithelial cells in a subject having a corneal ulcer or wound and increasing their adherence and in accelerating dermal wound healing.

Figure 2:
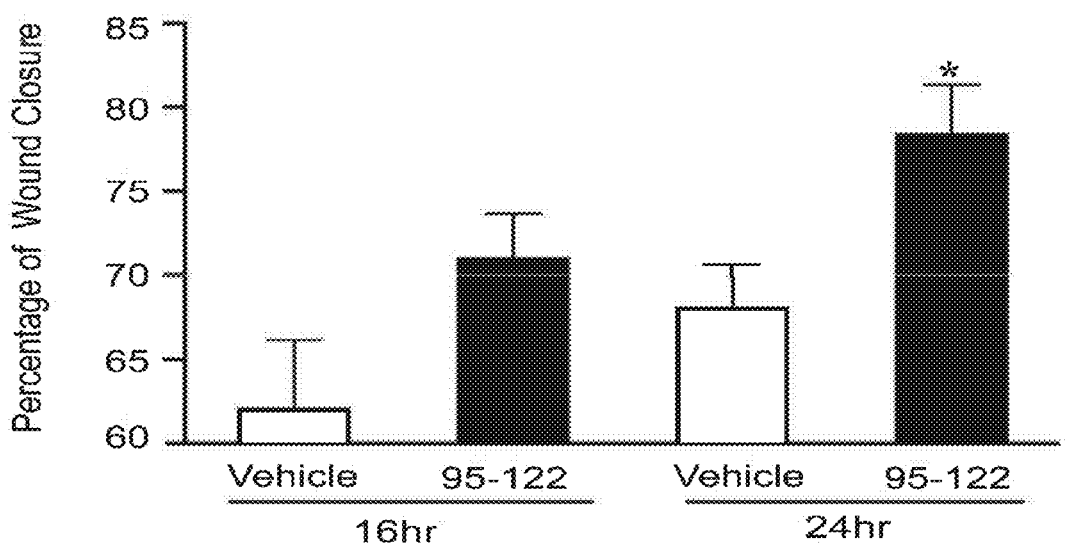
FIG. 2 shows that peptide 95-122 (SEQ ID NO:26) promotes corneal wound healing in vivo. The mouse corneal epithelium was removed using the AlgerBrush II (The Alger Company, Inc., Lago Vista, Tex.), and corneal abrasions were treated at 0 hours and 16 hours with peptide 95-122 ($10^{-5}$ M), or were left untreated in 0.9% sodium chloride (saline vehicle) Wound healing was monitored at 0, 16, and 24 hours using fluorescein staining and a camera-equipped inverted microscope. Data are represented as the percentage of wound closure at 16 hours and 24 hours and are expressed as means±SEM. The data are representative of at least 6 mice per group. *$P<0.05$ by unpaired t-test as compared to vehicle (0.9% sodium chloride) treated controls.
Figure 3:
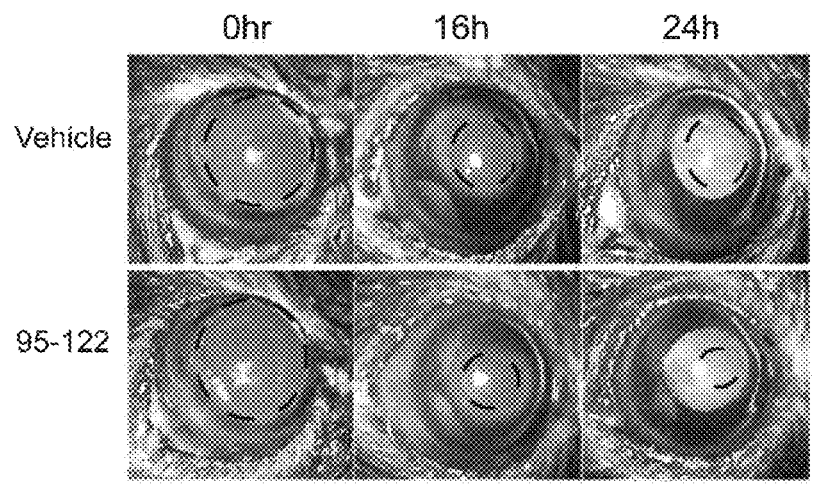
FIG. 3 shows that peptide 95-122 (SEQ ID NO:26) promotes corneal wound healing in vivo. The mouse corneal epithelium was removed using the AlgerBrush II, and corneal abrasions were treated at 0 hours and 16 hours with peptide 95-122 ($10^{-5}$ M), or were left untreated in 0.9% sodium chloride (saline vehicle). Wound healing was monitored at 0, 16, and 24 hours using fluorescein staining and a camera-equipped inverted microscope. Representative images of in vivo corneal abrasions are shown at 0, 16, and 24 hours.
Figure 5:
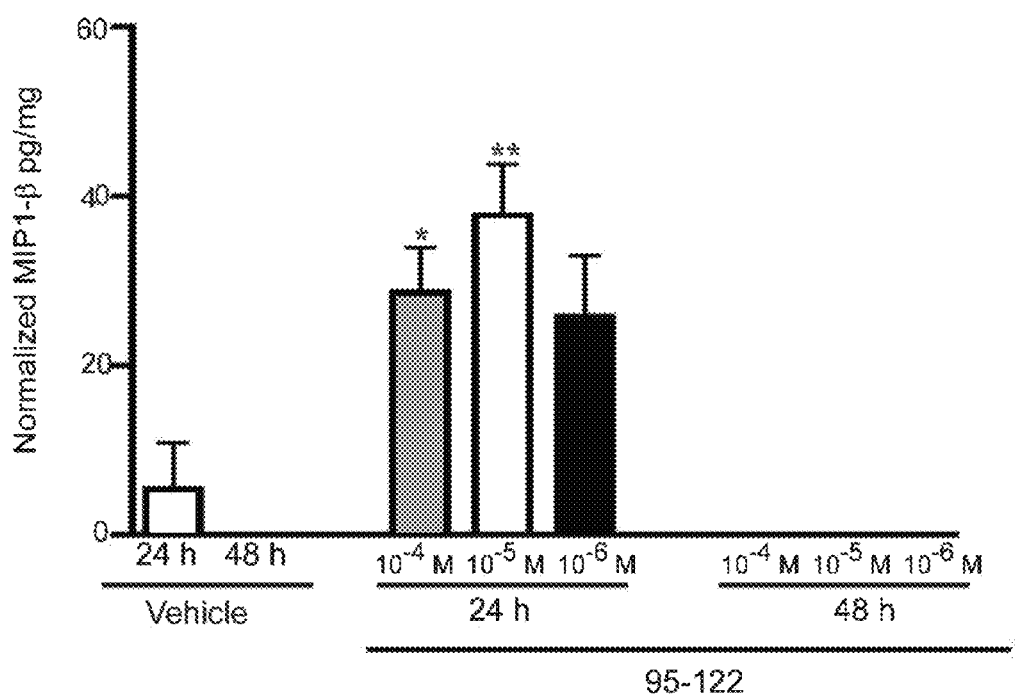
FIG. 5 shows that peptide 95-122 (SEQ ID NO:26) significantly increases MIP1-β. Corneas were injected intrastromally with 0.5 μl of peptide 95-122 at a final concentration of $10^{-4}$ M, $10^{-5}$ M, and $10^{-6}$ M and vehicle (saline) control. Corneas were collected and flash frozen at 24 hours and 48 hours. Corneal lysates were analyzed for cytokines using the MILLIPLEX® MAP mouse cytokine assay for MIP1-β (EMD Millipore Corp., Billerica, Mass.). **$P<0.01$, *$P<0.05$ by unpaired t-test as compared to vehicle treated controls.
Figure 4:
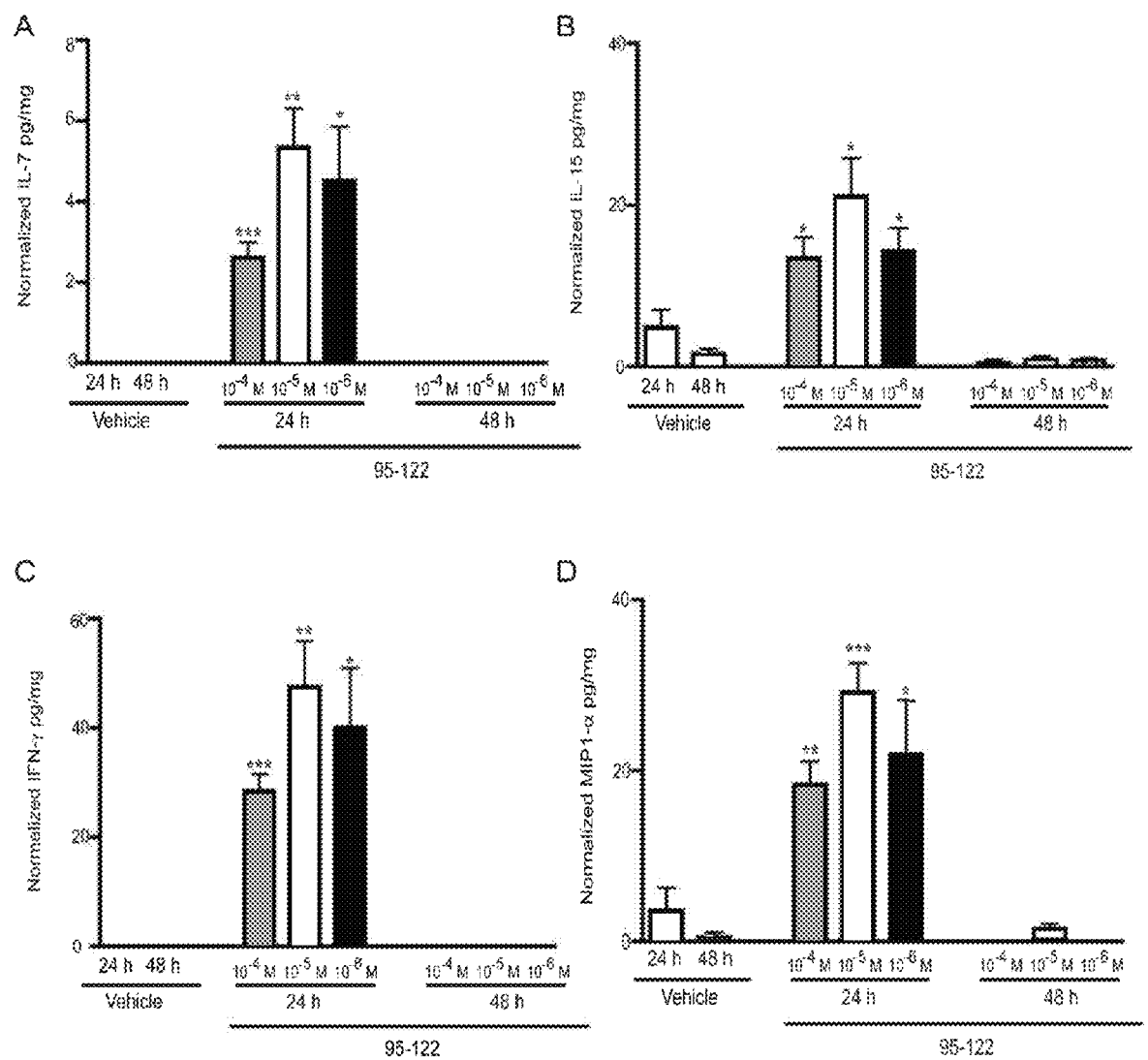
FIG. 4 shows that peptide 95-122 (SEQ ID NO:26) significantly increases IL-7, IL-15, IFN-γ, and MIP1-α. Corneas were injected intrastromally with 0.5 μl of peptide 95-122 at a final concentration of $10^{-4}$ M, $10^{-5}$ M, and $10^{-6}$ M and vehicle (saline) control. Corneas were collected and flash frozen at 24 hours and 48 hours. Corneal lysates were analyzed for cytokines using the MILLIPLEX® MAP mouse cytokine assay for IL-7(A), IL-15 (B), IFN-γ (C), MIP1-α (D) (EMD Millipore Corp., Billerica, Mass.). The means of independent experimental values are shown±SEM. *$P<0.001$, $P<0.01$, *$P<0.05$ by unpaired t-test as compared to vehicle treated controls.
Figure 6:
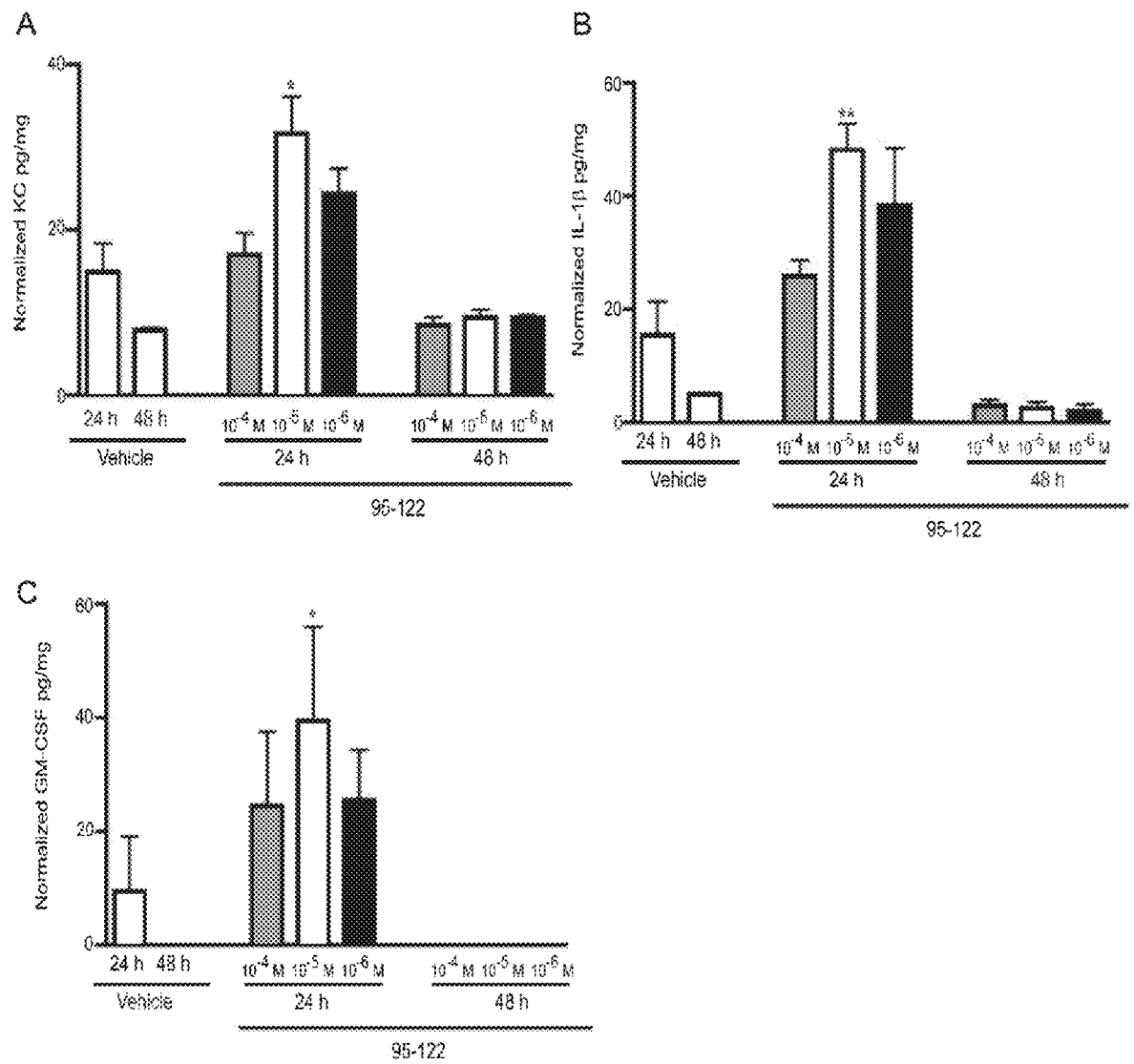
FIG. 6 shows that peptide 95-122 (SEQ ID NO:26) significantly increases KC, IL-10, and GM-CSF. Corneas were injected intrastromally with 0.5 μl of peptide 95-122 at a final concentration of $10^{-4}$ M, $10^{-5}$ M, and $10^{-6}$ M and vehicle (saline) control. Corneas were collected and flash frozen at 24 hours and 48 hours. Corneal lysates were analyzed for cytokines using the MILLIPLEX® MAP mouse cytokine assay for KC (A), IL-1β (B), and GM-CSF (C) (EMD Millipore Corp., Billerica, Mass.). **$P<0.01$, *$P<0.05$ by unpaired t-test as compared to vehicle treated controls.

These peptides (as shown, for example, in FIGS. 2-6 for Peptide 95-122), can be used, for example, to cause and/or promote: (a) chemotaxis of monocytes; (b) chemotaxis of human epithelial cells such as corneal epithelial cells; (c) wound healing in corneal epithelia (FIGS. 2 and 3), and (d) dermal wound healing. FIG. 2 is data analyzed and represented as histogram. FIG. 3 is the actual photograph of a treated mouse eye. Data from this photograph was used to generate the histogram in FIG. 2; and (d) cytokine production in response to intrastromal injection of the peptides (FIGS. 4-6).

"Peptides 95-122/102-122" (and derivatives): Described below are several peptides based on Peptide 95-122 (SEQ ID NO:26) and Peptide 102-122 (SEQ ID NO:27). These peptides include, but are not limited to, 95-122-5RMP$_{AEEA}$, 95-122-5RMP$_{AEEP}$, 102-122-5RMP$_{AEEA}$, and 102-122-5RMP$_{AEEP}$.

Peptide 95-122-5RMP$_{AEEA}$ is a derivatized version of peptide 95-122 which includes 2 small PEG (AEEA) moieties ("MP") and 4 arginine (R) residues at the amino terminus, and one R at the carboxy terminus. This peptide has the following sequence: (AEEA)-(AEEA)-RRRRL-DREANLTSSVTILPLPLQNATVEAGTRR (SEQ ID NO:48).

Peptide 95-122-5RMP$_{AEEP}$ is a derivatized version of peptide 95-122 which includes 2 small PEG (AEEP) moieties ("MP") and 4 arginine (R) residues at the amino terminus, and one R at the carboxy terminus. This peptide has the following sequence: (AEEP)-(AEEP)-RRRRL-DREANLTSSVTILPLPLQNATVEAGTRR (SEQ ID NO:46).

Peptide 102-122-5RMP$_{AEEA}$ is a derivatized version of peptide 102-122 which includes 2 small PEG (AEEA) moieties ("MP") and 4 arginine (R) residues at the amino terminus, and one R at the carboxy terminus. This peptide has the following sequence: (AEEA)-(AEEA)-RRRRTSSVTILPLPLQNATVEAGTRR (SEQ ID NO:50).

Peptide 102-122-5RMP$_{AEEP}$ is a derivatized version of peptide 102-122 which includes 2 small PEG (AEEP) moieties ("MP") and 4 arginine (R) residues at the amino terminus, and one R at the carboxy terminus. This peptide has the following sequence: (AEEP)-(AEEP)-RRRRTSSVTILPLPLQNATVEAGTRR (SEQ ID NO:49).

"Peptide 120-146" (and derivatives): Described below are several peptides based on Peptide 120-146 (SEQ ID NO:28), also known as 120-146QR. These peptides include, but are not limited to, 120-146QH, 120-146WR, 120-146WH, 120-146QR-5RMP, 120-146 QH-5RMP, 120-146WR-5RMP, and 120-146WH-5RMP.

Peptide 120-146, also referred to herein as peptide 120-146QR for the glutamine (Q) at position 131 and arginine (R) at position 132, has the following sequence: GTRCQVAGWGSQRSGGRLSRFPRFVNV (SEQ ID NO:28).

Peptide 120-146QH is derived from an induced form of CAP37 protein that was sequenced from corneal epithelial cells and has the following sequence, which is the same as peptide 120-146QR except that the arginine at position 132 is replaced by a histidine (hence the name 120-146QH): GTRCQVAGWGSQHSGGRLSRFPRFVNV (SEQ ID NO:29).

Peptide 120-146WR is an analog of peptide 120-146QR wherein the Glutamine (Gln, Q) at position 131 has been replaced by a tryptophan (Trp, W). This peptide has the following sequence:

(SEQ ID NO: 30)
GTRCQVAGWGSWRSGGRLSRFPRFVNV.

Peptide 120-146WH is an analog of peptide 120-146QH which has had the glutamine at position 131 replaced by a tryptophan (Trp, W). This peptide has the following sequence: GTRCQVAGWGSWHSGGRLSRFPRFVNV (SEQ ID NO:31).

Peptide 120-146QR-5RMP is a derivatized version of peptide 120-146QR which includes 2 small PEG (AEEP) moieties ("MP") and 4 arginine (R) residues at the amino terminus, and one R at the carboxy terminus. This peptide has the following sequence: (AEEP)-(AEEP)-RRRRGTRCQVAGWGSQRSGGRLSRFPRFVNVR (SEQ ID NO:32).

Peptide 120-146QH-5RMP is a derivatized version of peptide 120-146QH which includes 2 small PEG (AEEP) moieties ("MP") and 4 arginine (R) residues at the amino terminus, and one R at the carboxy terminus. This peptide has the following sequence: (AEEP)-(AEEP)-RRRRGTRCQVAGWGSQHSGGRLSRFPRFVNVR (SEQ ID NO:33).

Peptide 120-146WR-5RMP is a derivatized version of peptide 120-146WR which includes 2 small PEG (AEEP) moieties ("MP") and 4 arginine (R) residues at the amino terminus, and one R at the carboxy terminus. This peptide has the following sequence: (AEEP)-(AEEP)-RRRRGTRCQVAGWGSWRSGGRLSRFPRFVNVR (SEQ ID NO:34).

Peptide 120-146WH-5RMP is a derivatized version of peptide 120-146WH which includes 2 small PEG (AEEP) moieties ("MP") and 4 arginine (R) residues at the amino terminus, and one R at the carboxy terminus. This peptide has the following sequence: (AEEP)-(AEEP)-RRRRGTRCQVAGWGSWHSGGRLSRFPRFVNVR (SEQ ID NO:35).

Materials and Methods of Example 4

Synthesis of peptides: Peptides were synthesized using solid phase synthesis on an Applied Biosystems model 430A peptide synthesizer (0.1-mmol or 0.5-mmol scale).

Animals: C57BL/6 female mice were purchased from The Jackson Laboratory (Bar Harbor, Me., USA). All animals were treated humanely. The Institutional Animal Care and Use Committee (IACUC) at the University of Oklahoma, Okla. City, Okla. and the Dean McGee Eye Institute, Oklahoma City, Okla., approved all animal research protocols.

In vivo model of corneal wound healing: The in vivo model of wound healing was carried out using a disposable biopsy punch (2 mm, Miltex, York, Pa.) to demarcate the mouse cornea and a 0.5 mm burr using the AlgerBrush II (The Alger Company, Inc., Lago Vista, Tex.) to remove the corneal epithelium. The corneal abrasions were treated at 0 and 16 hours with peptide 95-122 ($10^{-5}$ M), peptide 120-146WH ($10^{-6}$ M and $10^{-8}$ M), peptide 120-146WR (($10^{-6}$ M and $10^{-8}$ M), or vehicle control (0.9% sodium chloride, pH 5.5, Baxter, Deerfield, Ill.). Corneal abrasions were visualized using sterile fluorescein sodium ophthalmic strips USP (Fluorets®, Chauvin Laboratory, Aubenas, France) dampened with sterile PBS. Images were taken at 0, 16, and 24 hours immediately following fluorescein staining.

Chemotaxis: Chemotaxis assays were performed using the modified Boyden chemotaxis chamber assay. Peptide 120-146QH was used at $10^{-4}$ M, $10^{-6}$ M, $10^{-8}$ M, $10^{-10}$ M, and $10^{-12}$ M, and peptide 120-146QR was used at $10^{-4}$ M, $10^{-6}$ M, $10^{-8}$M, and $10^{-10}$M.

Statistical analysis: In vivo wound healing experiments were analyzed using an unpaired t-test and ANOVA. Boyden chamber chemotaxis experiments were analyzed using a Wilcoxon signed-rank test. Statistics were calculated using GraphPad Prism 4.03 (GraphPad Software, Inc., San Diego, Calif.). The means of independent experimental values are shown±SEM and a P value of <0.05 was considered significant for all statistical analyses.

Results of Example 4

Figure 7:
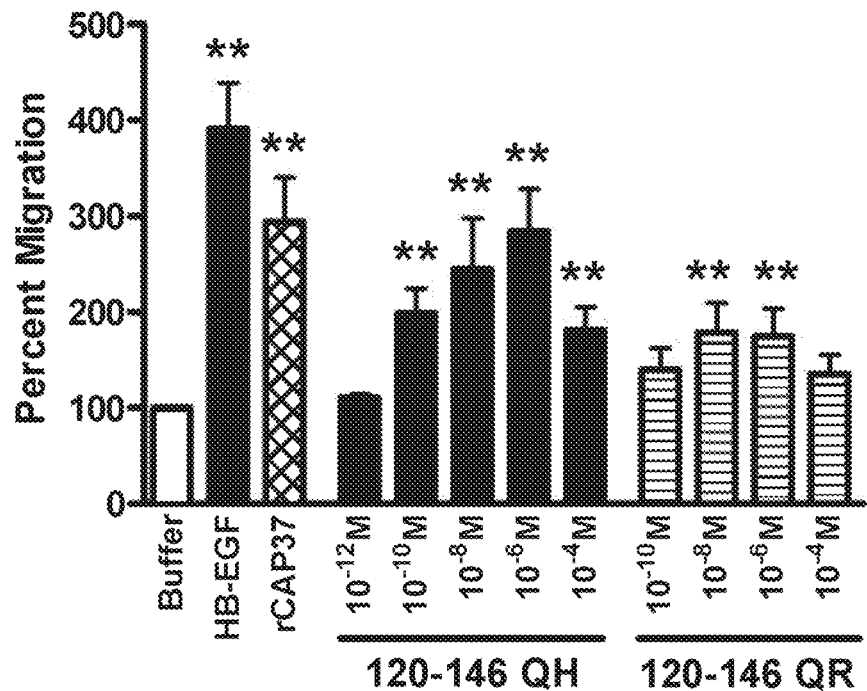
FIG. 7 shows that peptides 120-146QH (SEQ ID NO:29) and 120-146QR (SEQ ID NO:28), based on the native sequence of CAP37, mediate human corneal epithelial cell (HCEC) chemotaxis. The effect of buffer control (0.1% BSA in Gey's buffer), heparin binding-epidermal growth factor (HB-EGF, 50 ng/ml), recombinant CAP37 (rCAP37, 250 ng/ml), 120-146QH ($10^{-12}$M, $10^{-10}$ M, $10^{-8}$ M, $10^{-6}$M, and $10^{-4}$M,) and 120-146QR ($10^{-10}$M, $10^{-8}$M, $10^{-6}$M, and $10^{-4}$M) on HCEC chemotaxis was determined by the modified Boyden chemotaxis chamber method. HCEC chemotaxis was measured in response to HB-EGF, rCAP37, and peptides 120-146QH (SEQ ID NO:29) and 120-146QR (SEQ ID NO:28) after incubation for 3 hours at 37° C. Chemotaxis is expressed as a percent migration. The buffer control (no chemoattractant) is arbitrarily assigned the value of 100% migration. Data are expressed as means±SEM and are calculated from 6 observations for each test point. **$P<0.01$ by Wilcoxon signed-rank test as compared to controls.

Peptides 120-146QR (SEQ ID NO:28) and 120-146QH (SEQ ID NO:29) facilitate chemotaxis in HCECs. To elucidate the effect of CAP37-derived peptides on HCEC migration, HCECs were treated with peptides 120-146QH (SEQ ID NO:29), based on the native CAP37 sequence found in HCECs, and 120-146QR (SEQ ID NO:28), based on the native CAP37 sequence found in neutrophils, and migration in response to these peptides was measured using the modified Boyden chemotaxis chamber assay. Treatment with peptide 120-146QH (SEQ ID NO:29) at $10^{-4}$ M, $10^{-6}$ M, $10^{-8}$M, and $10^{-10}$ M and with peptide 120-146QR (SEQ ID NO:28) at $10^{-6}$ M and $10^{-8}$ M was found to significantly increase migration of HCECs in a dose-dependent manner (FIG. 7). Both peptides maximally facilitated migration between $10^{-6}$ M and $10^{-8}$ M. There was a significant increase in migration in response to HB-EGF (positive control) and CAP37 (positive control for the peptide) (FIG. 7). The migration with 120-146QH (SEQ ID NO:29) at $10^{-6}$ M and $10^{-8}$ M was comparable to the migration obtained with the whole CAP37 protein. Levels of migration with 120-146QR (SEQ ID NO:28) were less than the migration obtained with the whole protein, but significant when compared to the buffer control.

Peptide 120-146WH (SEQ ID NO:31) facilitates corneal epithelial wound healing. To determine the effect of both 120-146WR (SEQ ID NO:30) and 120-146WH (SEQ ID NO:31) peptides on corneal wound healing, an in vivo model of wound healing was utilized. Peptide 120-146WH (SEQ ID NO:31) contributed to the healing of in vivo wounds in a dose-dependent manner (FIGS. 8 and 9).

Results showed that peptide 120-146WH (SEQ ID NO:31) maximally facilitated wound healing between $10^{-6}$ M and $10^{-8}$ M. The amount of healing in 120-146WH-treated wounds was significantly greater (***$P<0.001$ and *$P<0.05$ as determined by unpaired t-test) than vehicle-treated samples (FIG. 8). Representative images of the in vivo wounds show a dose-dependent increase in wound healing in the 120-146WH-treated wounds versus the vehicle treated wounds (FIG. 9). Data presented herein indicate that the 120-146-based peptide compounds not only kill bacteria but also mediate chemotaxis and promote wound healing. None of the other bioactive peptides based on residues 20-44 (SEQ ID NO:7) and 95-122 (SEQ ID NO:26) of the native CAP37 protein have this dual function.

Figure 8:
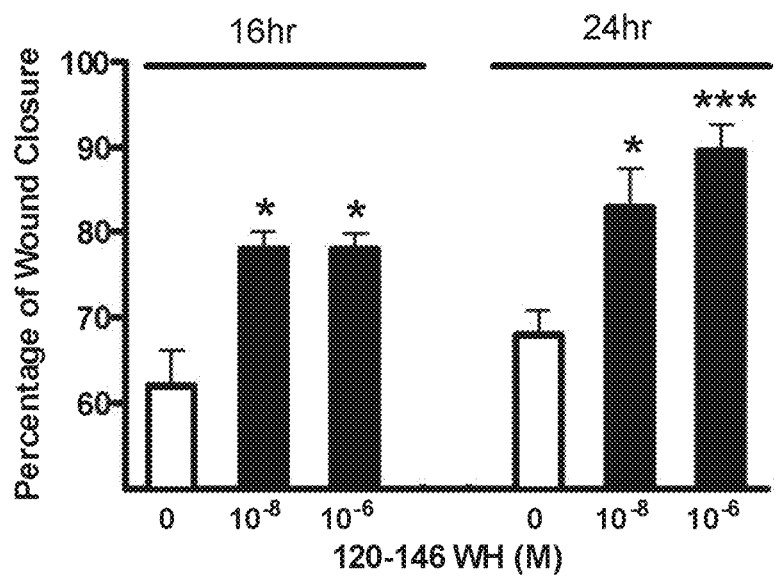
FIG. 8 shows that peptide 120-146WH (SEQ ID NO:31) promotes corneal wound healing in vivo. The mouse corneal epithelium was removed using the AlgerBrush II, and corneal abrasions were treated at 0 and 16 hours with peptide 120-146WH ($10^{-8}$ M or $10^{-6}$ M), or were left untreated in 0.9% sodium chloride (saline vehicle control). Wound healing was monitored at 0, 16, and 24 hours using fluorescein staining and a camera-equipped inverted microscope. Data are represented as the percentage of wound closure at 16 hours and 24 hours and are expressed as means±SEM. The data are representative of at least 6 mice per group. ***$P<0.001$, *$P<0.05$ by unpaired t-test as compared to vehicle (0.9% sodium chloride) treated controls.
Figure 9:
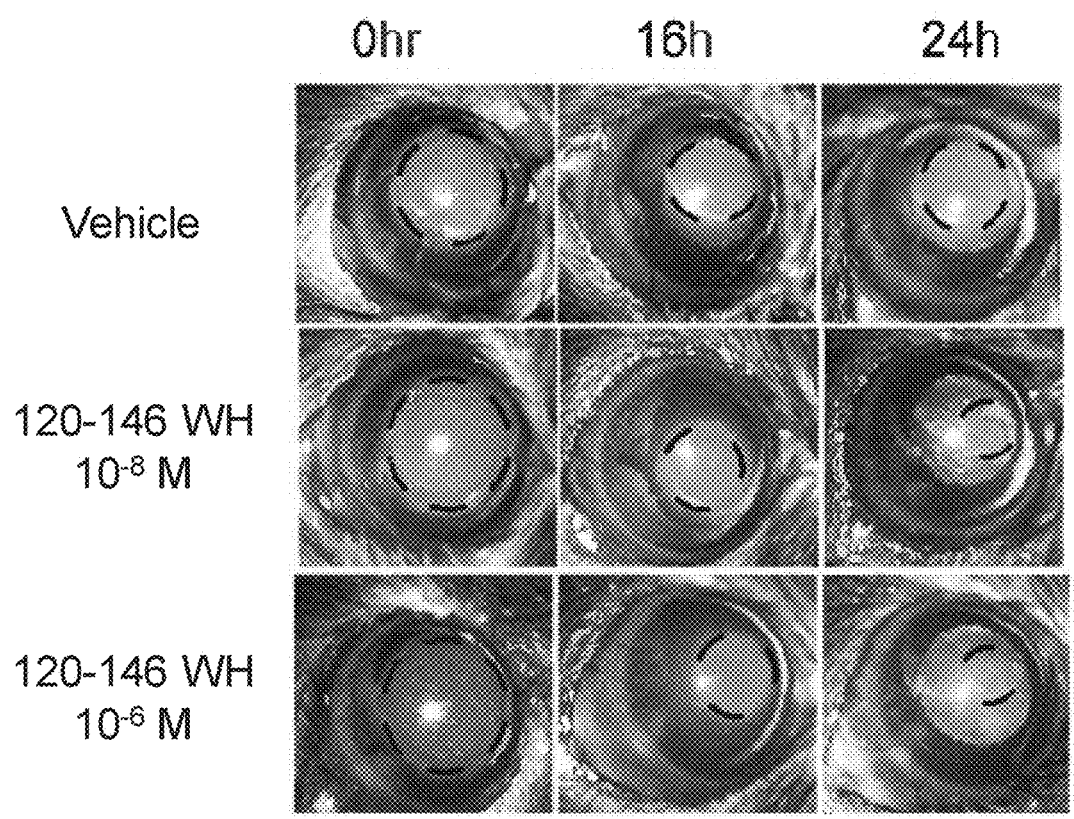
FIG. 9 shows that peptide 120-146WH (SEQ ID NO:31) promotes corneal wound healing in vivo. The mouse corneal epithelium was removed using the AlgerBrush II, and corneal abrasions were treated at 0 and 16 hours with peptide 120-146 WH ($10^{-8}$ M or $10^{-6}$ M), or were left untreated in 0.9% sodium chloride (saline vehicle control). Wound healing was monitored at 0, 16, and 24 hours using fluorescein staining and a camera-equipped inverted microscope. Representative images of in vivo wound closure of corneal abrasions are shown at 0, 16, and 24 hours.

Derivatives of peptides 95-122 and 120-146 comprise, in one embodiment, formulations suitable for dermal and or ophthalmic use, and in certain embodiments, formulations for wound healing are effective in wound healing (FIGS. 7-9 show, for example, 120-146-based peptides (e.g., SEQ ID NOS: 28-31). Certain embodiments of the presently disclosed inventive concepts further include combinations of a therapeutic using a presently disclosed peptide compound with wound healing properties along with another of the 120-146-based peptide compounds or any of the 20-44-5RMP series of CAP37 peptide compounds (i.e., SEQ ID NOS:21-23) to provide both healing as well as anti-infective power.

Example 5: Antibiotic Activity of 120-146-Based Peptide Compounds

Figure 10:
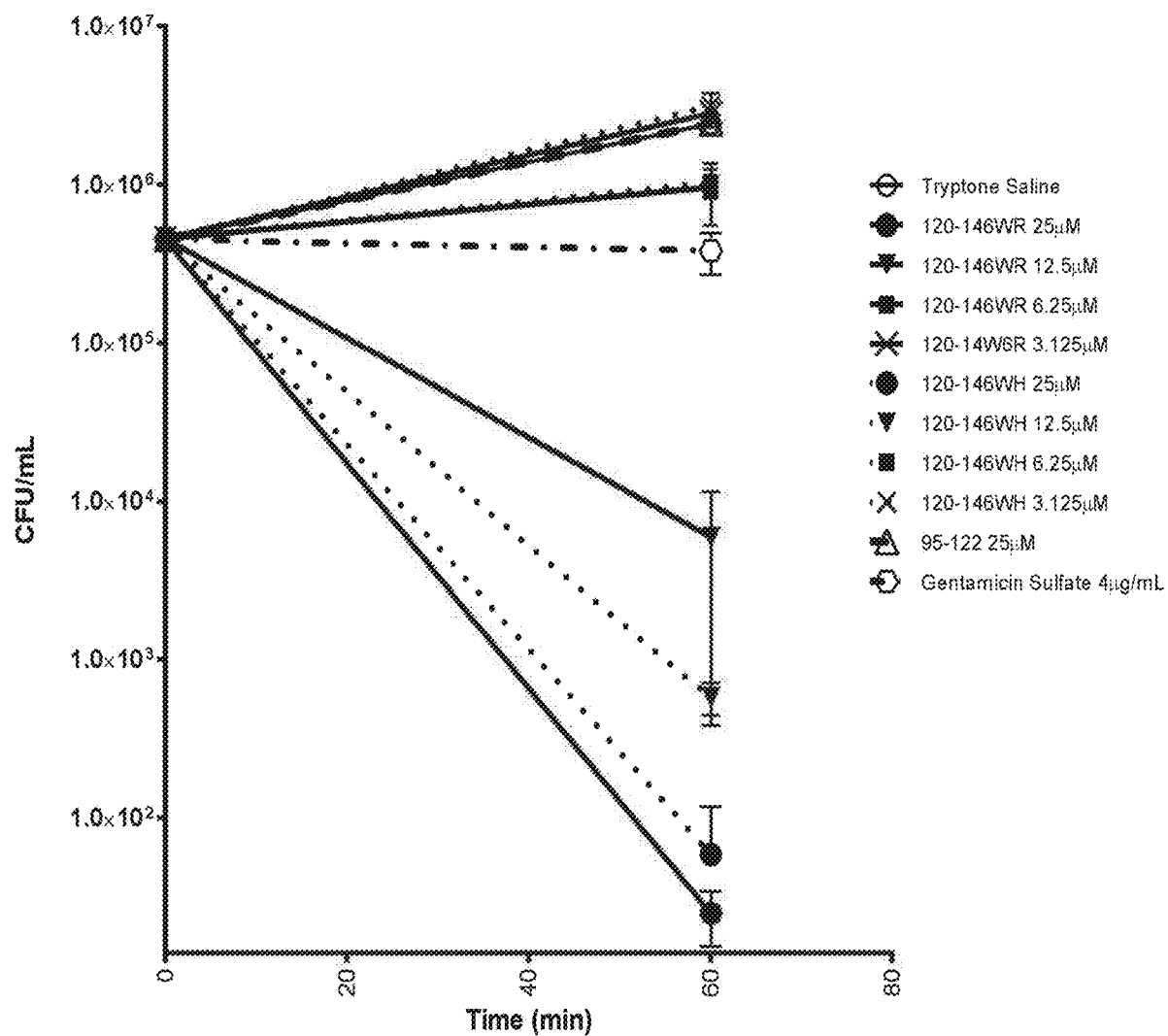
FIG. 10 shows bactericidal activity of CAP37 peptides 120-146WR (SEQ ID NO:30), 120-146WH (SEQ ID NO:31), and 95-122 (SEQ ID NO:26) compared with gentamicin as the comparator antibiotic. Each of the test peptides was used at 25, 12.5 6.25 and 3.12 μM. The gentamicin was used at 4 μg/ml. $1\times10^6$/ml *Acinetobacter baumannii* ATCC® BAA-747™ (American Type Culture Collection, Manassas, Va.) were incubated with the peptides, negative buffer control (tryptone saline), and positive control gentamicin for 60 minutes at pH 5.5. 50 μl aliquots were plated out on agar plates and incubated overnight. Colony forming units were counted after overnight incubation and CFU/ml calculated.

In this Example, peptide compounds based on Peptide 120-146 (i.e., SEQ ID NOS:28-35), as well as compositions containing these compounds, were shown to possess antibacterial activity against various bacteria. This Example demonstrates the usefulness of these compounds/compositions as antibiotics for treating various infections, including but not limited to, Pseudomonas aeruginosa, Acinetobacter baumannii, and other bacteria (see FIGS. 10-14). These peptide compounds/compositions can be used in monotherapy against bacteria that are resistant to standard antibiotics; these peptide compounds/compositions can also be used as antibiotics which are effective at neutral pH (FIGS. 11-12), and which are also active at low pH, including levels where gentamicin is not effective (FIGS. 10 and 13).

Materials and Methods of Example 5

For FIGS. 10-13, in vitro bactericidal assays were performed using a starting inoculum of $1\times10^6$ CFU/ml of the bacterial suspension. The CFU remaining at the end of the 60-180 minute incubation was determined, and the data was plotted as log reduction in CFU/ml.

In particular, each of the test peptides (CAP37 peptides 120-146WR, 120-146WH, and 95-122 (SEQ ID NOS:30, 31, and 26, respectively)) was used at 25, 12.5, 6.25, and 3.12 µM. Gentamicin was used at 4 µg/ml. $1\times10^6$/ml Acinetobacter baumannii ATCC® BAA-747™ or Pseudomonas aeruginosa ATCC® 27853™ (American Type Culture Collection, Manassas, Va.) were incubated with the peptides, negative buffer control (tryptone saline), and positive control gentamicin at pH 5.5 or 7.2. A 60 minute incubation was used for Acinetobacter baumannii ATCC® BAA-747™, while a 180 minute incubation was used for Pseudomonas aeruginosa ATCC® 27853™. 50 µl aliquots were plated out on agar plates and incubated overnight. Colony forming units were counted after overnight incubation and CFU/ml calculated.

Figure 14:
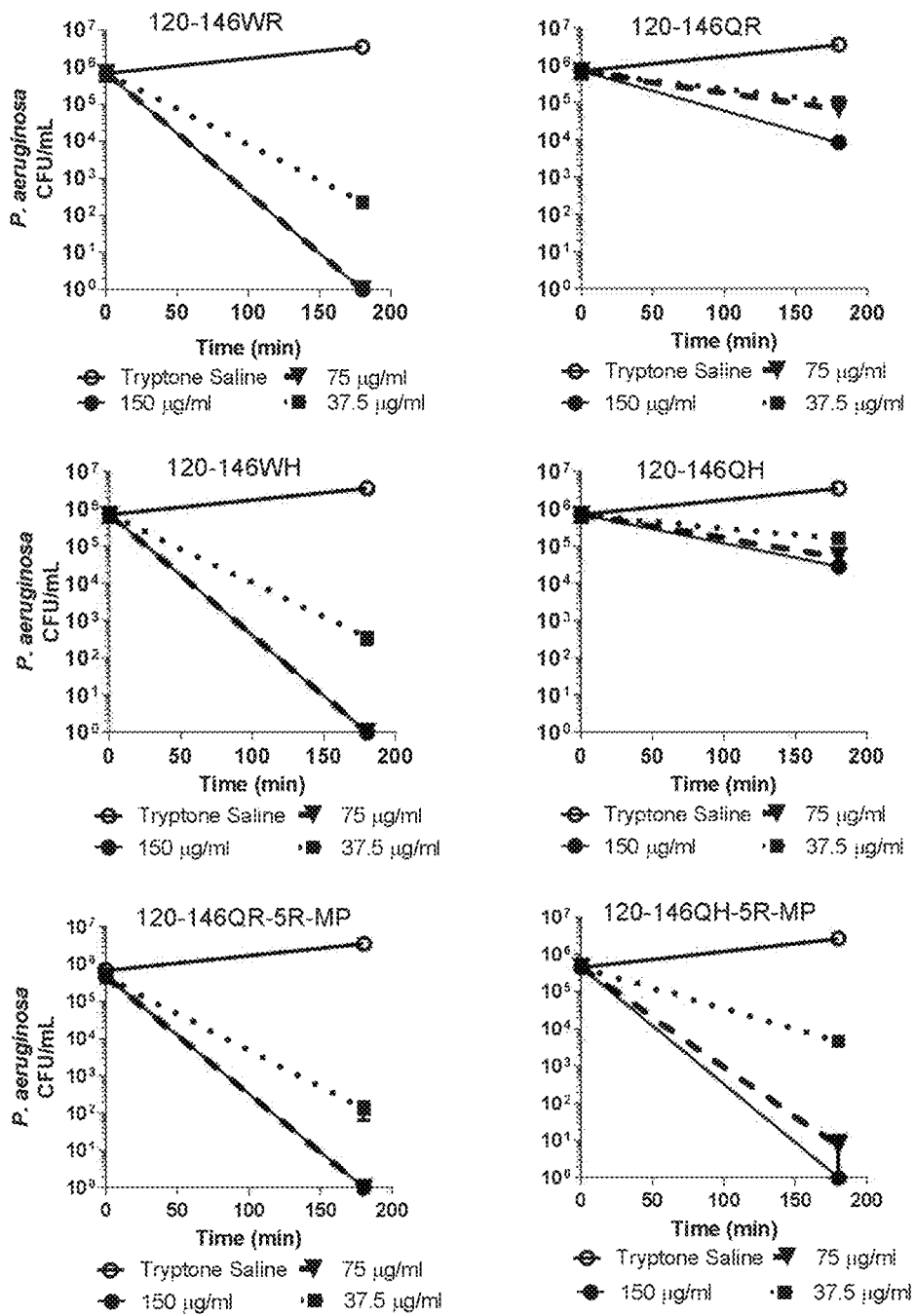
FIG. 14 is a comparison of bactericidal activity of CAP37 peptides 120-146WR (SEQ ID NO:30), 120-146WH (SEQ ID NO:31), 120-146QR (SEQ ID NO:28), 120-146QH (SEQ ID NO:29), 120-146QR-5RMP (SEQ ID NO:32), and 120-146QH-5RMP (SEQ ID NO:33) for *Pseudomonas aeruginosa* ATCC® 27853™ (American Type Culture Collection, Manassas, Va.). 1×10$^6$/ml *Pseudomonas aeruginosa* ATCC® 27853™ were incubated with the peptides at 150, 75, and 37.5 µg/ml and negative buffer control (tryptone saline) for 180 minutes at pH 5.5. 50 µl aliquots were plated out on agar plates and incubated overnight. Colony forming units were counted after overnight incubation and CFU/ml calculated.

For FIG. 14, $1\times10^6$/ml Pseudomonas aeruginosa ATCC® 27853™ were incubated with each of the test peptides (CAP37 peptides 120-146WR, 120-146WH, 120-146QR, 120-146QH, 120-146QR-5RMP, and 120-146QH-5RMP (SEQ ID NOS:30, 31, 28, 29, 32, and 33, respectively)) at 150, 75, and 37.5 µg/ml, or negative buffer control (tryptone saline), for 180 minutes at pH 5.5. 50 µl aliquots were plated out on agar plates and incubated overnight. Colony forming units were counted after overnight incubation and CFU/ml calculated.

Figure 15:
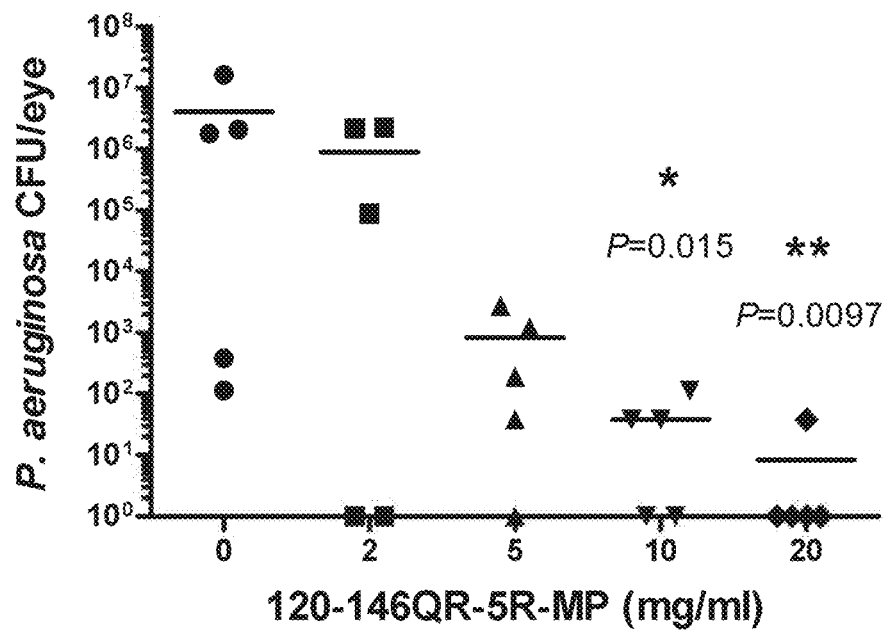
FIG. 15 shows that peptide 120-146QR-5RMP (SEQ ID NO:32) has antimicrobial activity in a mouse model of *Pseudomonas* keratitis. A circular wound was created on the mouse cornea by removing the epithelium, and the wound was infected with 10$^5$ CFU of *P. aeruginosa* (ATCC® 27853™ (American Type Culture Collection, Manassas, Va.)). Infected wounds were treated with saline or saline containing indicated concentrations (2, 5, 10, and 20 mg/ml) of peptide every 30 minutes for 6 hours on the first day. Infected wounds were treated twice on the second day and once on the third day. Mice were killed at 48 hours post-infection, and the CFU/eye were quantified. The means are plotted and are representative of 5 mice per group. Mann Whitney test was performed for each group as compared to the saline control group. *P=0.015 and **P=0.097.
Figure 16:
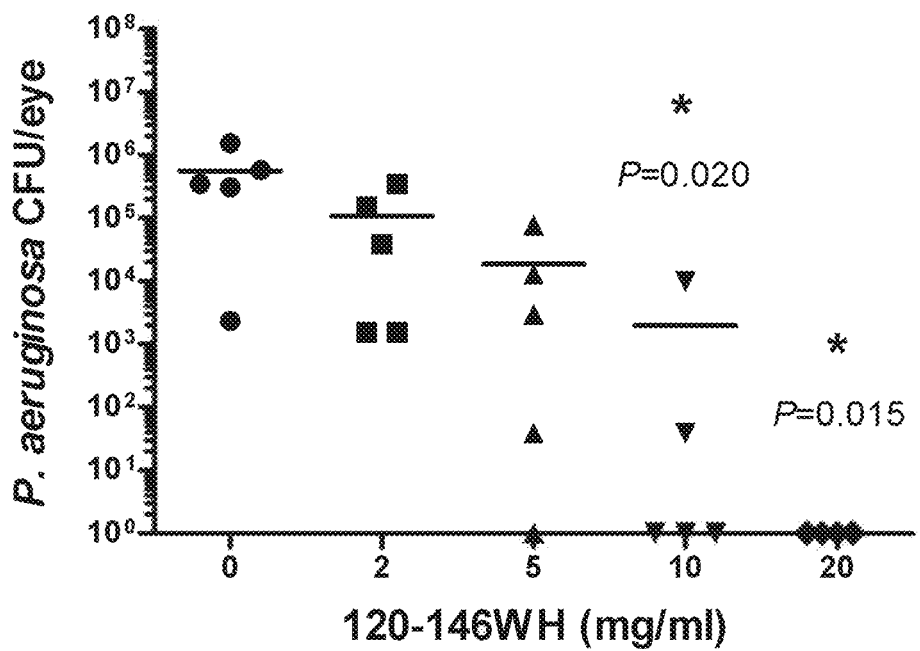
FIG. 16 shows that peptide 120-146WH (SEQ ID NO:31) has antimicrobial activity in a mouse model of *Pseudomonas* keratitis. A circular wound was created on the mouse cornea by removing the epithelium, and the wound was infected with 10$^5$ CFU of *P. aeruginosa* (ATCC® 27853™ (American Type Culture Collection, Manassas, Va.)). Infected wounds were treated with saline or saline containing indicated concentrations (2, 5, 10, and 20 mg/ml) of peptide every 30 minutes for 6 hours on the first day. Infected wounds were treated twice on the second day and once on the third day. Mice were killed at 48 hours post-infection, and the CFU/eye were quantified. The means are plotted and are representative of 4 to 5 mice per group. Mann Whitney test was performed for each group as compared to the saline control group.
Figure 17:
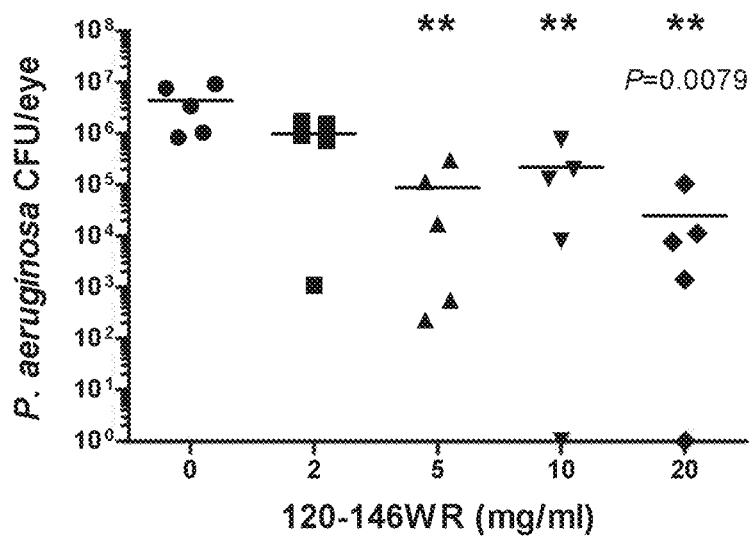
FIG. 17 shows that peptide 120-146WR (SEQ ID NO:30) has antimicrobial activity in a mouse model of *Pseudomonas* keratitis. A circular wound was created on the mouse cornea by removing the epithelium, and the wound was infected with 10$^5$ CFU of *P. aeruginosa* (ATCC® 27853™ (American Type Culture Collection, Manassas, Va.)). Infected wounds were treated with saline or saline containing indicated concentrations (2, 5, 10, and 20 mg/ml) of peptide every 30 minutes for 6 hours on the first day. Infected wounds were treated twice on the second day and once on the third day. Mice were killed at 48 hours post-infection, and the CFU/eye were quantified. The means are plotted and are representative of 5 mice per group. **P=0.0079 by Mann Whitney test as compared to the saline control group.

For FIGS. 15-17, in vivo bactericidal activity of the peptides was also investigated using the standard Pseudomonas keratitis model in the mouse eye (FIGS. 15-17). Peptides 120-146QR-5RMP (SEQ ID NO:32), 120-146WH (SEQ ID NO:31), and 120-146WR (SEQ ID NO: 30) were applied topically at doses of 2, 5, 10, and 20 mg/ml to the wounded cornea that had been infected with $10^5$ CFU of Pseudomonas aeruginosa. The efficacies of the peptides were compared to treatment with the vehicle control. Mice were euthanized at 48 hours post infection, and the CFU/eye were quantified.

Results of Example 5

Figure 11:
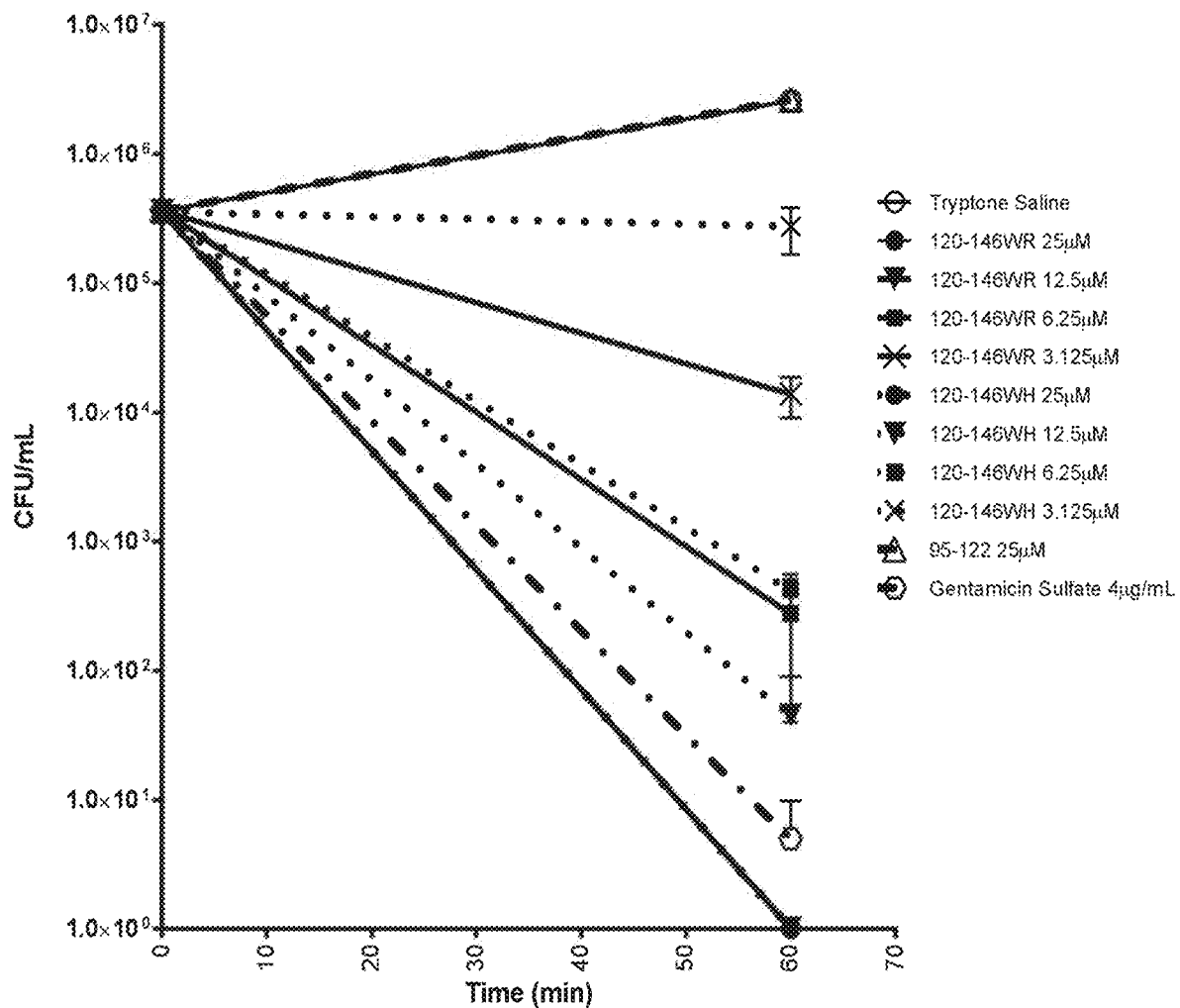
FIG. 11 shows bactericidal activity of CAP37 peptides 120-146WR (SEQ ID NO:30), 120-146WH (SEQ ID NO:31), and 95-122 (SEQ ID NO:26) compared with gentamicin as the comparator antibiotic. Each of the test peptides was used at 25, 12.5 6.25 and 3.12 μM. The gentamicin was used at 4 μg/ml. $1\times10^6$/ml *Acinetobacter baumannii* ATCC® BAA-747™ (American Type Culture Collection, Manassas, Va.) were incubated with the peptides, negative buffer control (tryptone saline), and positive control gentamicin for 60 minutes at pH 7.2. 50 μl aliquots were plated out on agar plates and incubated overnight. Colony forming units were counted after overnight incubation and CFU/ml calculated.

FIGS. 10 and 11 show bactericidal activity of CAP37 peptides 120-146WR (SEQ ID NO:30), 120-146WH (SEQ ID NO:31), and 95-122 (SEQ ID NO:26) against Acinetobacter baumannii ATCC® BAA-747™ (American Type Culture Collection, Manassas, Va.) at two different pH's, and as compared with gentamicin as the comparator antibiotic. As can be seen, the CFU/ml were reduced by almost 4 logs at pH 5.5 (FIG. 10) and by almost 5.5 logs at pH 7.2 (FIG. 11) at the highest peptide concentrations of the CAP37 peptides 120-146WR and 120-146WH used; thus, the peptides had greater activity at pH 7.2 than at pH 5.5. The standard antibiotic gentamicin was unable to kill the bacteria at pH 5.5, even though it was used at more than its standard minimum inhibitory concentrations (MIC). In contrast, the standard antibiotic gentamicin was active against the bacteria at pH 7.2. Peptide 95-122 was not active against Acinetobacter at either pH. Peptides 120-146WR and 120-146WH at 25 µM and peptide 120-146WR at 12.5 µM were highly active against A. baumannii.

Figure 12:
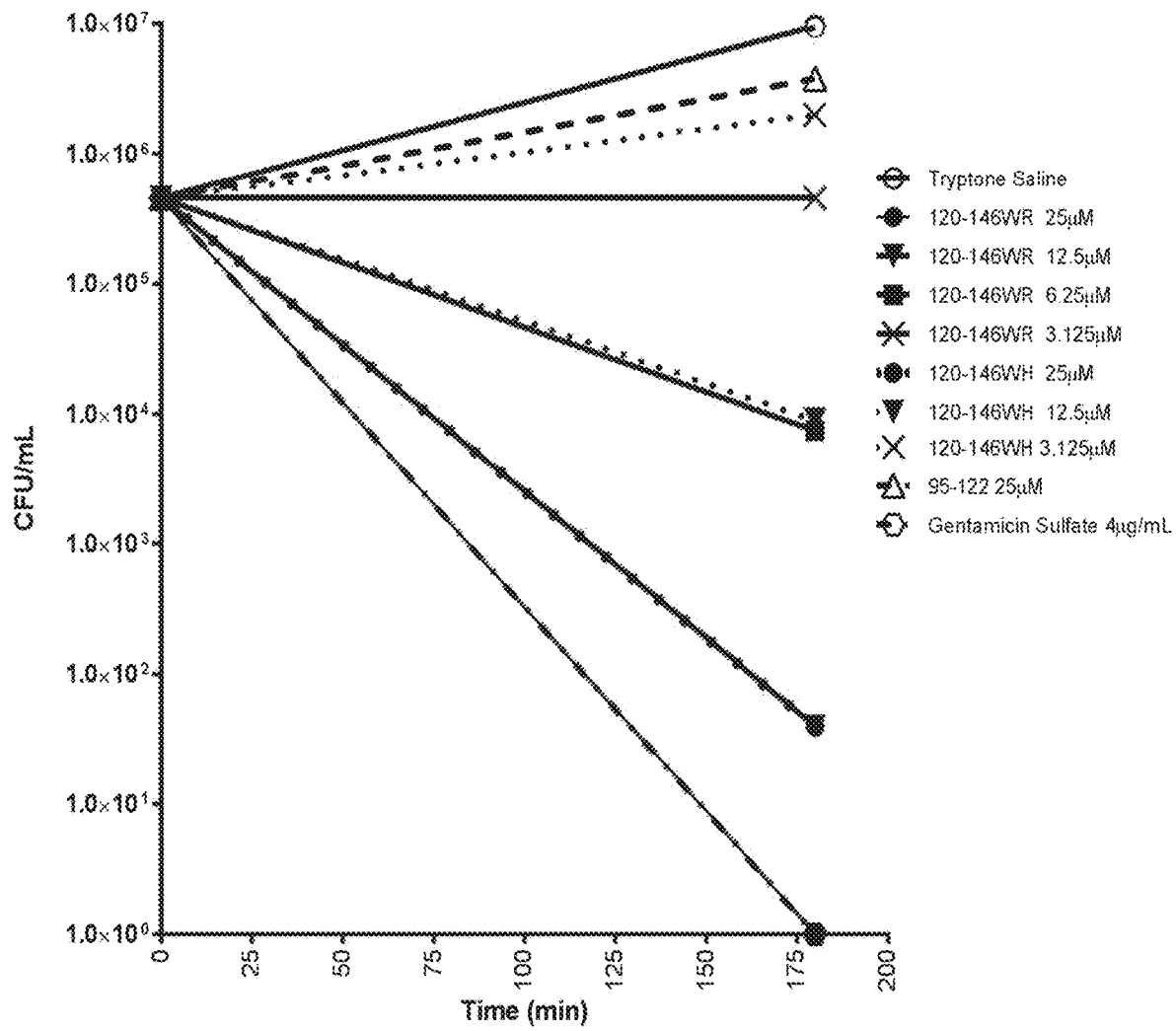
FIG. 12 shows bactericidal activity of CAP37 peptides 120-146WR (SEQ ID NO:30), 120-146WH (SEQ ID NO:31), and 95-122 (SEQ ID NO:26) compared with gentamicin as the comparator antibiotic. Each of the test peptides was used at 25, 12.5 6.25, and 3.12 μM. The gentamicin was used at 4 μg/ml. $1\times10^6$/ml *Pseudomonas aeruginosa* ATCC® 27853™ (American Type Culture Collection, Manassas, Va.) were incubated with the peptides, negative buffer control (tryptone saline), and positive control gentamicin for 180 minutes at pH 7.2. 50 μl aliquots were plated out on agar plates and incubated overnight. Colony forming units were counted after overnight incubation and CFU/ml calculated.
Figure 13:
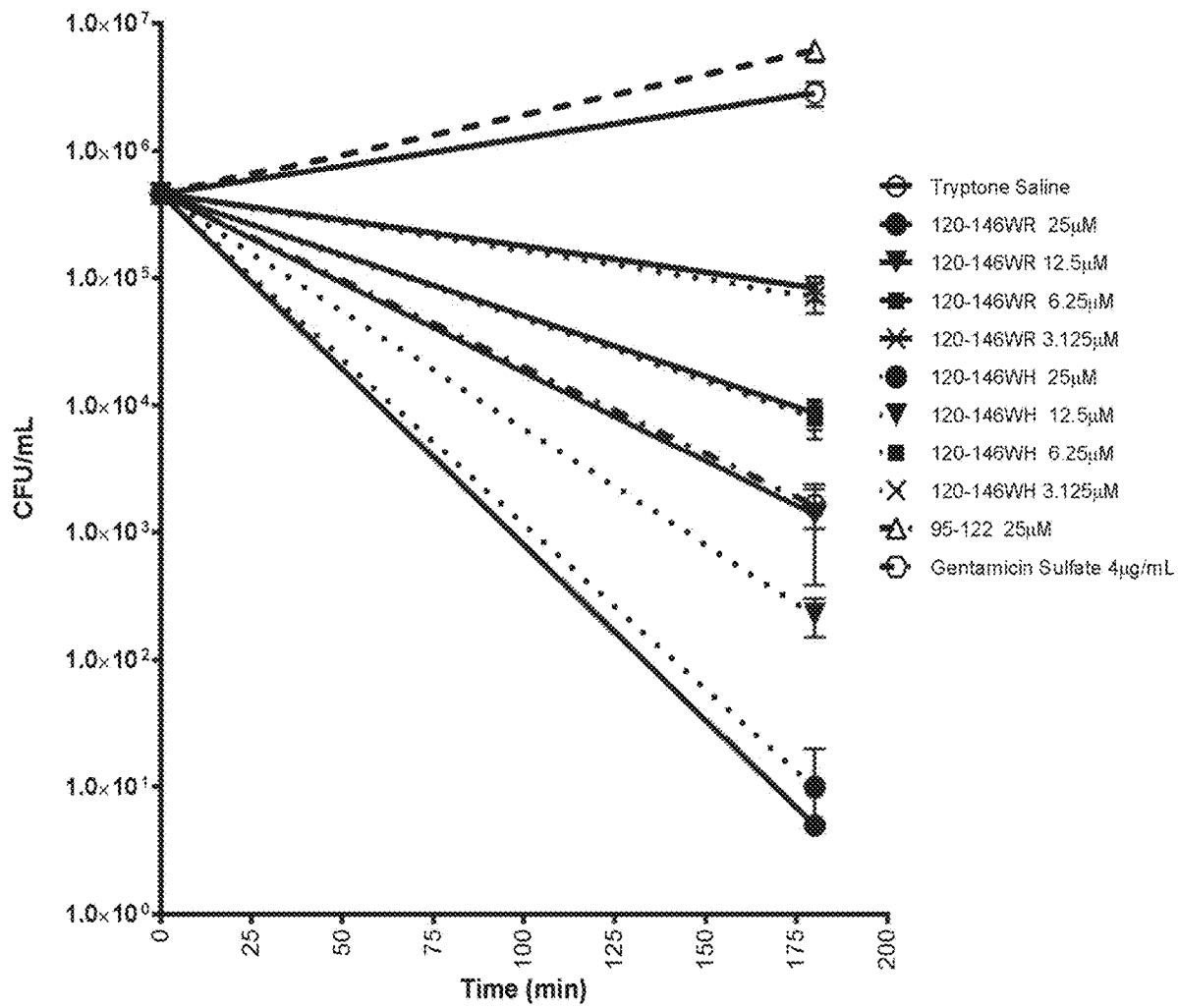
FIG. 13 shows bactericidal activity of CAP37 peptides 120-146WR (SEQ ID NO:30), 120-146WH (SEQ ID NO:31), and 95-122 (SEQ ID NO:26) compared with gentamicin as the comparator antibiotic. Each of the test peptides was used at 25, 12.5, 6.25, and 3.12 µM. The gentamicin was used at 4 µg/ml. 1×10$^6$/ml *Pseudomonas aeruginosa* ATCC® 27853™ (American Type Culture Collection, Manassas, Va.) were incubated with the peptides, negative buffer control (tryptone saline), and positive control gentamicin for 180 minutes at pH 5.5. 50 µl aliquots were plated out on agar plates and incubated overnight. Colony forming units were counted after overnight incubation and CFU/ml calculated.

FIGS. 12 and 13 show bactericidal activity of CAP37 peptides 120-146WR (SEQ ID NO:30), 120-146WH (SEQ ID NO:31), and 95-122 (SEQ ID NO:26) against Pseudomonas aeruginosa ATCC® 27853™ (American Type Culture Collection, Manassas, Va.) at two different pH's, and as compared with gentamicin as the comparator antibiotic. As can be seen, the CFU/ml were reduced by 6 logs at pH 7.2 (FIG. 12) and by 4-5 logs at pH 5.5 (FIG. 13) at the highest concentrations of peptides 120-146WR and 120-146WH used; thus, the peptides had greater activity at pH 7.2 than at pH 5.5. Peptides 120-146WR and 120-146WH at 25 µM were as effective as the standard antibiotic gentamicin at pH 7.2; gentamicin was not as effective as the peptides against the bacteria at pH 5.5 (showing only a 2 log reduction), even though it was used at more than its standard MIC. Peptide 95-122 was not active against Pseudomonas aeruginosa at either pH. Peptides 120-146WH at 25 µM and 120-146WR at 12.5 µM had the same effect. Peptide 120-146WR at 25 µM and gentamicin were highly active against *P. aeruginosa*.

FIG. 14 is a comparison of bactericidal activity of CAP37 peptides 120-146WR (SEQ ID NO:30), 120-146WH (SEQ ID NO:31), 120-146QR (SEQ ID NO:28), 120-146QH (SEQ ID NO:29), 120-146QR-5RMP (SEQ ID NO:32), and 120-146QH-5RMP (SEQ ID NO:33) for *Pseudomonas aeruginosa* ATCC® 27853™ (American Type Culture Collection, Manassas, Va.). As can be seen at the highest concentrations of peptides with the native sequence (120-146QR and 120-146QH, SEQ ID NOS:28 and 29, respectively), the CFU count was lowered by 1-2 logs. With the replacement of the amino acid residue at position 131 with a tryptophan, the killing efficiency of the peptides (120-146WR and 120-146WH, SEQ ID NOS:30 and 31, respectively) was increased, reducing the CFU by 6 logs. Modification of the native sequence (120-146QR-5RMP and 120-146QH-5RMP, SEQ ID NOS:32 and 33, respectively), which possesses relatively low activity, by the addition of the 5RMP increased killing such that approximately a 6 log reduction in CFU was obtained, even at the lower concentrations of the peptide (75 µg/ml). It was concluded by extrapolation that peptides generated with sequences 120-146WR-5RMP (SEQ ID NO:34) and 120-146WH-5RMP (SEQ ID NO:35) are highly effective, even at substantially lower concentrations of the peptide.

FIG. 14 shows in detail how the addition of the 5RMP extension (SEQ ID NOS:32-33) to the relatively inactive peptides 120-146QR (SEQ ID NO:30) and 120-146QH (SEQ ID NO:29) enhanced bactericidal activity significantly. Peptides 120-146WR (SEQ ID NO:30) and 120-146WH (SEQ ID NO:31) were strongly active in in vitro killing assays, indicating that the replacement of the glutamine residue (Q) at position 131 with a tryptophan residue (W) markedly increased killing. It can thus be predicted that a peptide based on 120-146WR-5RMP (SEQ ID NO:34) or 120-146WH-5RMP (SEQ ID NO:35) would have superior killing capabilities.

In vivo bactericidal activity of Peptides 120-146QR-5RMP (SEQ ID NO:32), 120-146WH (SEQ ID NO:31), and 120-146WR (SEQ ID NO: 30) was also investigated using the standard *Pseudomonas* keratitis model in the mouse eye (FIGS. 15-17). FIG. 15 shows that peptide 120-146QR-5RMP (SEQ ID NO:32) significantly reduced the CFU/eye at doses of 10 and 20 mg/ml. Six of the 10 mice in these two groups had no viable bacteria in the eye after treatment. FIG. 16 shows that peptide 120-146WH (SEQ ID NO:31) significantly reduced the CFU/eye at doses of 10 and 20 mg/ml. FIG. 17 shows that peptide 120-146WR (SEQ ID NO:30) significantly reduced infection at 5, 10, and 20 mg/ml.

Example 6

Dermal Wound Healing Studies Using 95-122-Based and 120-146-Based Peptide Compounds.

In this Example, peptide compounds of the presently disclosed inventive concepts were evaluated as to their activity on the dermal wound healing process in a clinically relevant swine full thickness excisional wound model. Three different peptide formulations (Group B, Peptide 95-122 (SEQ ID NO:26); Group C, Peptide 120-146WH (SEQ ID NO:31); and Group D, Peptide 120-146QH-5RMP (SEQ ID NO:33)) were each evaluated at the same concentration (3 mg/ml). Sterile saline served as the control (Group A).

Full thickness excisional wounds were induced on the dorsum of swine (N=3) using a 1.0 cm biopsy punch. Treatments were administered (0.20 ml) to each wound (N=6 wounds per group), and the wounds were dressed with standard occlusive dressing (TEGADERM™, 3M Corporation, St. Paul, Minn.). Treatments were reapplied daily and dressings changed. Clinical wound healing observations and wound area (2 mm) measurements were performed on days 0, 3, 5, 7, 10, and 14 post-wounding. Wound area (2 mm) data were expressed as percentage (%) of wound healing. Animals were terminated on day 14 with wounds harvested and processed for histological evaluation. Clinical observations revealed no remarkable differences between groups for erythema and edema throughout the study. All peptide formulation treatment groups healed faster with greater rate of closure and re-epithelialization over time, as compared to the saline control (Group A).

Figure 18:
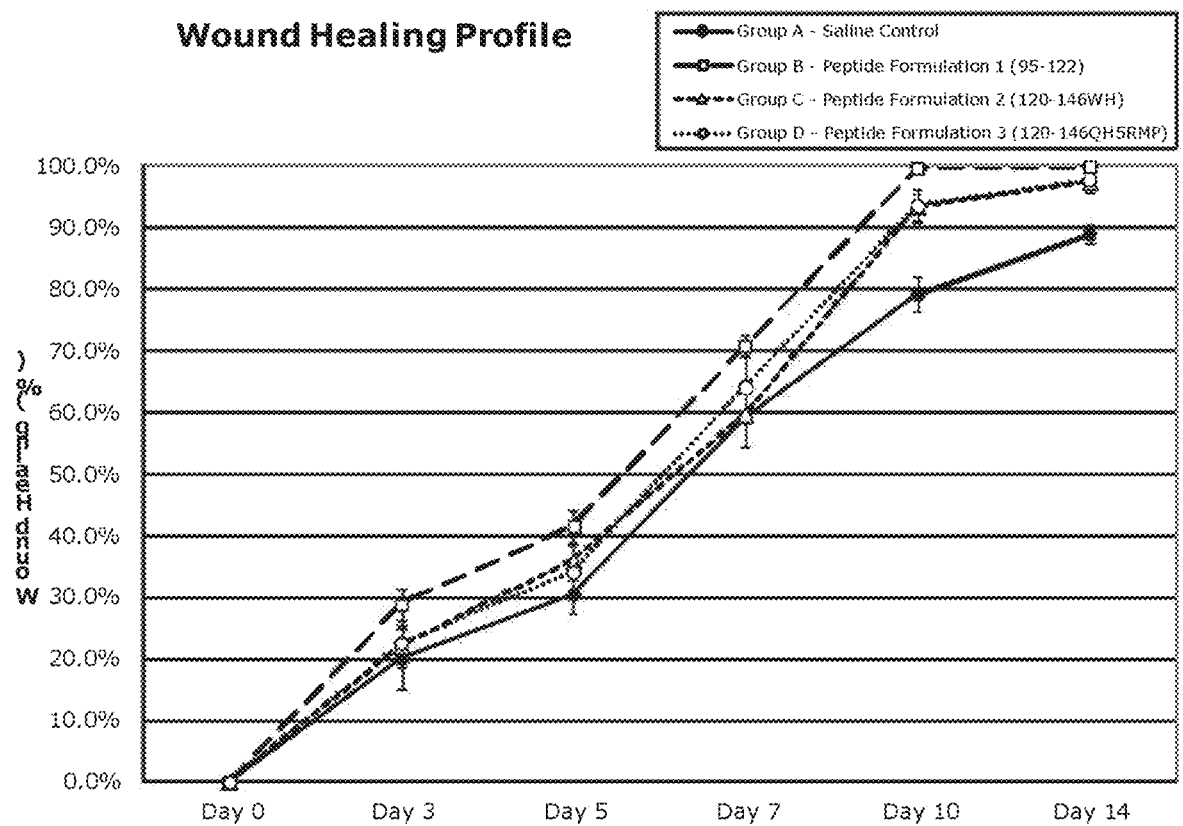
FIG. 18 shows that CAP37 peptides 95-122 (SEQ TD NO:26), 120-146WH (SEQ ID NO:31), and 120-146QH-5RMP (SEQ ID NO:33) accelerate dermal wound healing. Graphical results of in vivo wound healing in swine skin over 14 days using saline as a control and three CAP37-based peptide compounds used topically at 3 mg/ml are shown.

The results (see FIG. 18 and Table 7) from the quantitative wound area measurements indicate, in comparison to the saline control Group A, the percentage (%) of wound healing was greater for Group B (95-122; SEQ ID NO:26) wounds throughout the study. Group B (95-122) demonstrated a significant (p<0.05) increase in the percentage of wound healing on days 5, 7, 10, and 14, with 99.7% of the wounds closed and re-epithelialized by day 10. Groups C (120-146WH, SEQ ID NO:31) and D (120-146QH-5RMP, SEQ ID NO:33) also demonstrated a significant (p<0.05) increase in the percentage of wound healing on days 10 and 14 post-wounding Table 8 shows the statistical analysis for the wound healing measurements.

TABLE 7

Swine Wound Healing Results

| Mean Wound Healing (%) | Day: | | | | | |
|---|---|---|---|---|---|---|
| | 0 | 3 | 5 | 7 | 10 | 14 |
| Group A - Saline Control | 0.0% | 20.1% | 30.5% | 59.0% | 79.2% | 88.9% |
| Group B - Peptide Formulation 1 (95-122) | 0.0% | 28.9% | 41.5% | 70.8% | 99.7% | 100.0% |
| Group C - Peptide Formulation 2 (120-146WH) | 0.0% | 22.1% | 35.9% | 59.7% | 93.5% | 97.5% |
| Group D - Peptide Formulation 3 (120-146QH5RMP) | 0.0% | 22.5% | 34.1% | 64.1% | 93.7% | 98.0% |

TABLE 8

Statistical Analysis of Swine Wound Healing Results

| | Day 3 | Day 5 | Day 7 | Day 10 | Day 14 |
|---|---|---|---|---|---|
| Group A vs Group B | 0.1407 | 0.0196 * | 0.0350 * | 0.0000 *** | 0.0000 *** |
| Group A vs Group C | 0.7388 | 0.2264 | 0.9200 | 0.0022 ** | 0.0030 ** |

TABLE 8-continued

Statistical Analysis of Swine Wound Healing Results

|  | Day 3 | Day 5 | Day 7 | Day 10 | Day 14 |
|---|---|---|---|---|---|
| Group A vs Group D | 0.7032 | 0.5124 | 0.4766 | 0.0041 ** | 0.0017 ** |

Figure 19:
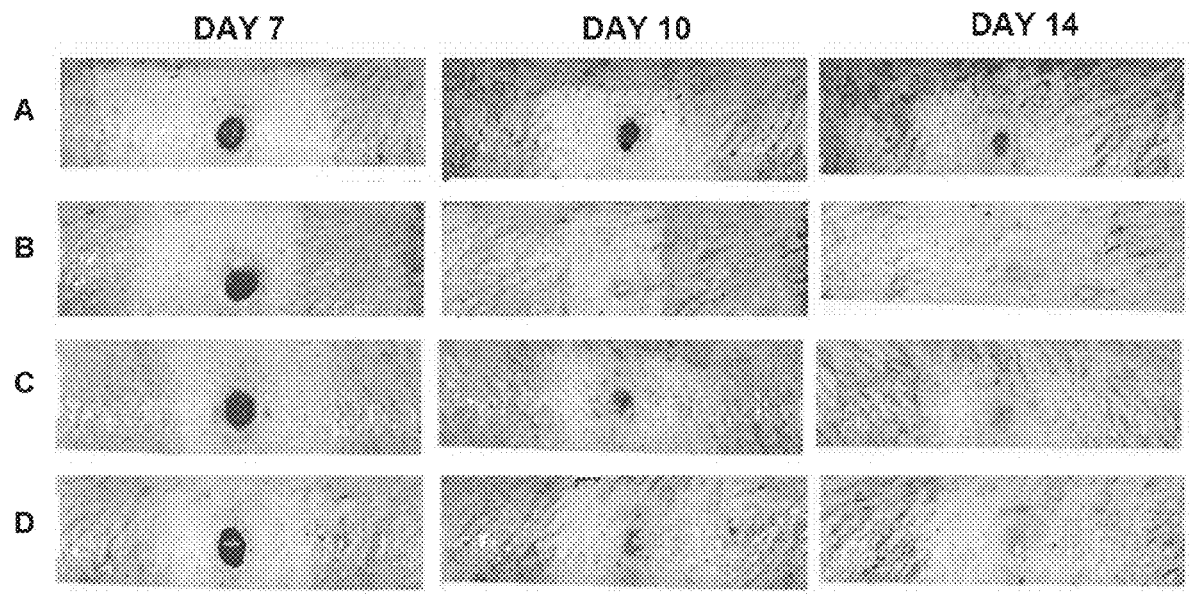
FIG. 19 contains representative results of dermal wound healing in swine, as evidenced by photographs of the results shown graphically in FIG. 18. Panel A: Saline vehicle control. Panel B: peptide 95-122 (SEQ ID NO:26). Panel C: peptide 120-146WH (SEQ ID NO:31). Panel D: peptide 120-146QH-5RMP (SEQ ID NO:33).

FIG. 19 shows representative pictures taken on days 7, 10, and 14 demonstrating the extent of wound healing in response to saline (top row) or peptide 95-122 (SEQ ID NO:26; second row), peptide 120-146WH (SEQ ID NO:31; third row), or peptide 120-146QH-5RMP (SEQ ID NO:33; fourth row). The percent values in Table 7 are measurements taken from the results shown in FIG. 19.

Figure 20:
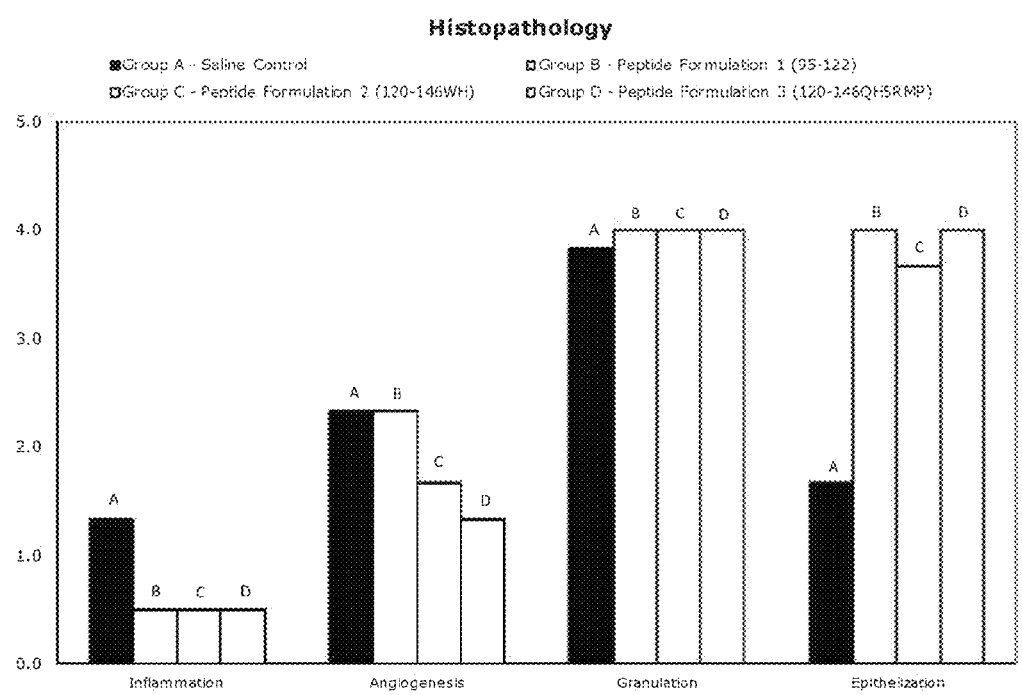
FIG. 20 shows histopathology from swine dermal wound healing study based on the criteria of inflammation, angiogenesis, granulation, and epithelialization of the results of FIGS. 18-19. The characteristics that were measured are required to indicate features of a well-healed wound. Inflammation should be low and re-epithelialization high.

The histology correlated with the clinical observations. All peptide treatment groups (Group B, 95-122 (SEQ ID NO:26); Group C, 120-146WH (SEQ ID NO:31); and Group D, 120-146QH-5RMP (SEQ ID NO:33)) demonstrated a greater extent of epidermal resurfacing and maturation of the epidermis at day 14 post-wounding, as compared to the saline control (Group A). The results from the histological evaluation are provided in FIG. 20 and Table 9. There were minimal differences in the amount or character of granulation tissue, inflammation, and angiogenesis. All the wounds were well filled and vascularized. The major difference was that Groups B, C, and D demonstrated a greater extent of epidermal resurfacing and maturation of the epidermis (stratification of basal and suprabasal layers, appearance of a well-organized stratum corneum), as compared to the saline control.

TABLE 9

Histopathology Results

| Mean | Inflammation | Angiogenesis | Granulation | Epithelization |
|---|---|---|---|---|
| Group A - Saline Control | 1.3 | 2.3 | 3.8 | 1.7 |
| Group B - Peptide Formulation 1 (95-122) | 0.5 | 2.3 | 4.0 | 4.0 |
| Group C - Peptide Formulation 2 (120-146WH) | 0.5 | 1.7 | 4.0 | 3.7 |
| Group D - Peptide Formulation 3 (120-146QH5RMP) | 0.5 | 1.3 | 4.0 | 4.0 |

Example 7: Treatment of Corneal Wound Healing with CAP37 Protein

Human corneal epithelial cell (HCEC) monolayers were "wounded" then treated with CAP37, and wound closure was recorded over time. In an in vivo model of corneal wound healing, a 2 mm diameter wound was made on the mouse cornea. Wounds were treated with CAP37, and wound closure was monitored at 16 and 24 hours by fluorescein staining. CAP37 treatment was shown to facilitate corneal wound healing. Relevant CAP37 sequences are disclosed in U.S. Pat. No. 7,354,900, which is hereby expressly incorporated herein by reference in its entirety.

Materials and Methods of Example 7

Cell culture: SV40 adenovirus immortalized HCECs were obtained as a generous gift from Dr. James Chodosh (Boston, Mass.). HCECs were maintained in defined keratinocyte-serum free media (KSFM, Gibco, Grand Island, N.Y.) supplemented with L-glutamine (2 mM, Gibco), antibiotic-antimycotic (0.1 units/mL penicillin G sodium, 100 μg/mL streptomycin sulfate, 0.25 μg/mL amphotericin B, Gibco), and growth supplements as provided by the manufacturer. HCECs used in these experiments were between passage 10 and 20.

Primary HCECs were isolated from donor corneas acquired from the Lions Eye Bank (Oklahoma City, Okla.). Each cornea was quadrisected and placed in Hank's balanced salt solution (HBSS, Gibco) containing dispase (25 caseinolytic U/mL; Becton Dickinson Discovery Labware, Bedford, Mass.) and 5 μg/mL gentamicin (A.G. Scientific Inc., San Diego, Calif.). The corneal tissue was incubated overnight on ice at 4° C. Corneal epithelial cells were obtained by lifting the epithelial layer from the surface of the cornea with a scalpel. Following a 5 minute digest in 0.25% Trypsin-EDTA (trypsin-ethylenediaminetetraacetic acid, Gibco), an equal amount of heat-inactivated fetal bovine serum (FBS, Gibco) was added to the corneal epithelial cells. The cells were centrifuged at 450×g for 5 minutes, and the cell pellet was resuspended in KSFM supplemented with growth factors, as specified by the manufacturer. Cells were seeded and cultured on tissue culture dishes treated with an FNC coating mix containing fibronectin, collagen, and albumin (AthenaES, Baltimore, Md.). Prior to performing all experiments, HCEC cultures were placed in KSFM that did not contain growth factors (basal KSFM) for a minimum of 18 hours.

Production of recombinant CAP37: Recombinant CAP37 (rCAP37) was produced in human embryonic kidney (HEK) 293 cells using an RSV-PL4 expression vector. The recombinant protein was purified on an HPC4 immunoaffinity column as previously described. All preparations of rCAP37 were dialyzed in 0.01% acetic acid and determined to be pure by sodium dodecyl sulfate polyacrylamide gel electrophoresis (SDS-PAGE) and Western blot analysis. Functional activity was assessed using the modified Boyden chemotaxis chamber assay as previously described. rCAP37 preparations used in these studies had <0.05 endotoxin units per microgram of protein, as determined by the Limulus Amebocyte Lysate assay (QCL 1000, Lonza, Basel, Switzerland).

Animals: C57BL/6 female mice were purchased from Jackson Laboratory (Bar Harbor, Me.). Mice were acclimated for 4-7 days and were all 8 weeks of age at the start of the experiments. The animal research protocols were reviewed and approved by the Institutional Animal Care and Use Committee (IACUC) at the University of Oklahoma Health Sciences Center, Oklahoma City, Okla. and the Dean McGee Eye Institute, Oklahoma City, Okla.

In vitro model of wound healing: An in vitro scratch assay was used in order to determine the ability of rCAP37 to facilitate corneal wound healing. Human corneal epithelial cells were cultured as described above until they reached a confluent monolayer. Each monolayer was scratched using a 10 μl pipette tip to create two perpendicular lines. Monolayers were treated with heparin binding-epidermal growth factor (HB-EGF, 250 ng/ml; Becton Dickinson), rCAP37 (25-2000 ng/ml), or basal KSFM (Gibco). Wound closure was monitored at 0, 18, 24, and 48 hours utilizing a camera-equipped inverted microscope (TE2000-E; Nikon, Melville, N.Y.). Time-lapse images of in vitro wound closure were obtained using a camera-equipped inverted microscope (TE2000-E; Nikon) from β-18 hours. HCEC monolayers were treated with HB-EGF, rCAP37, and basal KSFM as described above. The width of each scratch was quantitated using ImageJ software (US National Institutes of Health, Bethesda, Md.). Results are presented as the percentage of wound closure.

In vivo model of wound healing: Mice were anesthetized using ketamine (100 mg/kg; Bionichepharma, LLC., St. Lake Forrest, Ill.) and xylazine (10 ng/kg; Rompun; Bayer Corp., Shawnee Mission, Kans.), and the right cornea was wounded as follows. A disposable biopsy punch (2 mm, Miltex, York, Pa.) was used to demarcate the mouse cornea. The corneal epithelium was carefully removed within the 2 mm demarcated area with a 0.5 mm burr using the Alger-Brush II (The Alger Company, Inc., Lago Vista, Tex.). The corneal abrasions were treated at 0 and 16 hours with HB-EGF (250 ng/ml), rCAP37 (250 ng/ml), or vehicle control (0.9% sodium chloride, pH 5.5, Baxter, Deerfield, Ill.). Corneal abrasions were visualized using sterile fluorescein sodium ophthalmic strips USP (FLUORETS®, Chauvin Laboratory, Aubenas, France) dampened with sterile PBS. Images were taken at 0, 16, 24, and 48 hours immediately following fluorescein staining using a surgical microscope equipped with a camera (Carl Zeiss OPMI VISU 140, Carl Zeiss Surgical, Inc., Oberkochen, Germany). The areas of the open wound were quantitated using ImageJ software (US National Institutes of Health), and the results were reported as the percentage of wound closure.

Histology: Whole mouse eyes were collected for histology at 0, 6, 16, 24, and 48 hours post wounding and were immediately placed in Prefer fixative (Anatech LTD., Battle Creek, Mich.) for 20 minutes before being transferred to 70% ethanol. Tissues were paraffin-embedded and cut at a thickness of 5 µm, mounted on SUPERFROSTPLUS® slides (Statlab Medical Products, Lewisville, Tex.), and subsequently deparaffinized, rehydrated, and washed in deionized water. Sections were stained with hematoxylin (Leica Microsystems, Buffalo Grove, Ill.) and rinsed twice in deionized water before being washed in Blue Buffer (Leica Microsystems). The sections were finally washed in deionized water and 95% ethanol prior to being counterstained with eosin (Leica Microsystems). Sections were dehydrated in ethanol and cleared in xylene.

Immunohistochemistry: Whole mouse eyes were collected, fixed, embedded, and cut as previously described. Antigen retrieval was performed by treating sections with Rodent Decloaker (BioCare Medical, Concord, Calif.) and steaming them for 20 minutes before cooling with deionized water for 20 minutes. Sections were blocked for 30 minutes in Rodent Blocker M (BioCare Medical, Concord, Calif.), washed three times for 5 minutes per wash in deionized water, and blocked in peroxide block (Cell Marque, Rocklin, Calif.) for 10 minutes. Sections were then washed three times for 5 minutes in deionized water and incubated overnight at 4° C. with rabbit anti-PKCδ (4 µg/ml; Santa Cruz Biotechnology, Inc. Santa Cruz, Calif.). Sections incubated with rabbit IgG (Cell Signaling Technology, Danvers, Mass.) overnight at 4° C. served as controls for nonspecific staining. After incubation with primary antibody, sections were washed three times for 5 minutes in Tris-buffered saline (TBS) and incubated with rabbit-on-rodent horseradish peroxidase (HRP)-polymer (BioCare Medical) for 30 minutes. Following three, 5 minute washes in TBS, sections were stained with 3',3'-diaminobenzidine tetrahydrochloride (DAB) chromogen (Cell Marque, Rocklin, Calif.), washed in deionized water, and counterstained with Immuno Master Hematoxylin (American Master*Tech Scientific, Inc., Lodi, Calif.). Images of the stained tissues were obtained using an inverted microscope (TE2000-E; Nikon) equipped with a camera.

Immunofluorescence: HCECs and primary HCECs were cultured on Lab-Tek® II glass chamber slides (Nunc, Rochester, N.Y.) and starved overnight in basal media. For wounding studies, monolayers were scratched with a 10 µl pipette tip or left unscratched and treated with 1 µM phorbol 12-myristate 13-acetate (PMA, Sigma-Aldrich), rCAP37 (25-500 ng/ml), or basal KSFM (Gibco) for 15 minutes. After treatment, the cells were fixed in 4% (v/v) formaldehyde solution (Thermo, Rockford, Ill.) in PBS (Gibco) for 20 minutes at room temperature followed by permeabilization in 0.5% TRITON™-X 100 (Mallinckrodt, St. Louis, Mo.) in PBS for 10 minutes. Remaining formaldehyde was quenched with 0.05 M ammonium chloride ($NH_4Cl$, Sigma-Aldrich, St. Louis, Mo.) in PBS for 10 minutes. Cells were washed in PBS and incubated in blocking buffer (10% (v/v) normal goat serum in PBS containing 5% bovine serum albumin (BSA, Calbiochem, Gibbstown, N.J.)) and 0.5% TRITON™-X 100 (Mallinckrodt, St. Louis, Mo.) at room temperature for 1 hour. To detect the PKC isoforms, cells were incubated in primary mouse antibodies (Becton Dickinson Discovery Labware) directed against PKCδ (250 ng/ml), PKCθ (500 ng/ml), PKCα, (1 µg/ml), or PKCγ (1 µg/ml) for 1 hour at room temperature. Mouse IgG (1 µg/ml; Jackson ImmunoResearch) served as the control for non-specific staining. The cells were washed in PBS containing 0.25% TRITON™-X 100 (Mallinckrodt) and incubated in secondary antibody (4 µg/ml in blocking buffer; ALEXA FLUOR® 488 dye (Life Technologies Corp., Grand Island, N.Y.)) for 1 hour at room temperature. Cells were washed three times for 5 minutes in PBS followed by a final water wash and mounted using PROLONG® Gold Antifade containing DAPI (Molecular Probes/Life Technologies Corp., Grand Island, N.Y.). Images were obtained using an inverted epifluorescent microscope (TE2000-E; Nikon).

siRNA transfection and gene silencing: Stealth RNAi™ (10 µM, Ambion®, Grand Island, N.Y.) directed against PKCδ or Stealth RNAi™ siRNA Negative Control Hi GC (10 µM, Ambion®) was delivered into the mouse conjunctiva through a 5 µl subconjunctival injection using a 33-gauge needle (Hamilton®, Reno, Nev.). After subconjunctival injection, the corneas were immediately wounded using the AlgerBrush II as described above. Wound closure was quantitated at 16 and 24 hours as described. Animals were humanely euthanized at 24 hours, and each cornea was excised using a SklarSafe™ Safety Scalpel #11 (SKLAR®, West Chester, Pa.). Tissues were immediately flash frozen. Corneal homogenates were prepared as described below and analyzed for levels of PKCδ by Western blot analysis to confirm the efficiency of each knockdown. The level of PKCδ in the knockdown cornea was compared to the Stealth RNAi™ siRNA Negative Control Hi GC (Ambion®).

Protein extraction and Western blotting: Mouse corneas were excised using a SklarSafe™ Safety Scalpel #11 (SKLAR®) and frozen at the indicated time points as described above. Corneas were placed in 200 µl of radioimmunoprecipitation assay (RIPA) buffer containing a 1× cocktail of cOmplete ULTRA Protease Inhibitors (Roche Diagnostics Corp., Indianapolis, Ind.). Tissue homogenates were created by disrupting the corneas for 10 minutes at maximum speed in the BULLET BLENDER® (Next Advance, Inc., Averill Park, N.Y.) using 0.9-2 mm stainless steel beads (Next Advance, Inc.). The homogenates were centrifuged at 16,000×g for 10 minutes, and the protein concentration of the supernatant from each corneal homogenate sample was determined using a BCA protein concentration assay (Pierce, Rockford, Ill.).

Protein (20 μg) from each sample of corneal homogenate was analyzed by electrophoresis on a 10% SDS-PAGE gel. Following electrophoresis, samples were transferred to nitrocellulose membranes (Whatman® Inc. Florham Park, N.J.) for Western blot analysis. Nitrocellulose membranes (Whatman® Inc.) were blocked for 1 hour in 5% BSA (Calbiochem) in Tris Buffered Saline with TWEEN®20 (Thermo Fisher Scientific, Pittsburgh, Pa.) (TBST) and then incubated overnight at 4° C. with 5% BSA (Calbiochem) in TBST containing primary antibodies directed against PKCδ (Santa Cruz) or 3-actin (Sigma-Aldrich) as specified by the manufacturers. The membranes were washed three times for 5 minutes in TBST before being incubated at room temperature for 1 hour with rabbit (Cell Signaling Technology, Danvers, Mass.) or mouse (Sigma-Aldrich) secondary antibody conjugated to HRP. Secondary antibodies were used as directed by the manufacturer. Blots were developed using Pierce ECL Western Blotting Substrate and visualized using the UltraLum Imager (Omega, Claremont, Calif.). Blots were analyzed and semi-quantitated using ImageJ software (U.S. National Institutes of Health, Bethesda, Md.).

Statistics: In vitro wound healing experiments were analyzed using a one-way analysis of variance (ANOVA) followed by a Dunnett's multiple comparison test. In vivo wound healing and PKCδ knockdown studies were analyzed using an unpaired t-test. GraphPad Prism 4.03 (GraphPad Software, Inc., San Diego, Calif.) was used for statistical analysis. The independent means of experimental values are shown±SEM. $P<0.05$ was considered significant for all statistical analyses.

Results of Example 7

Figure 21:
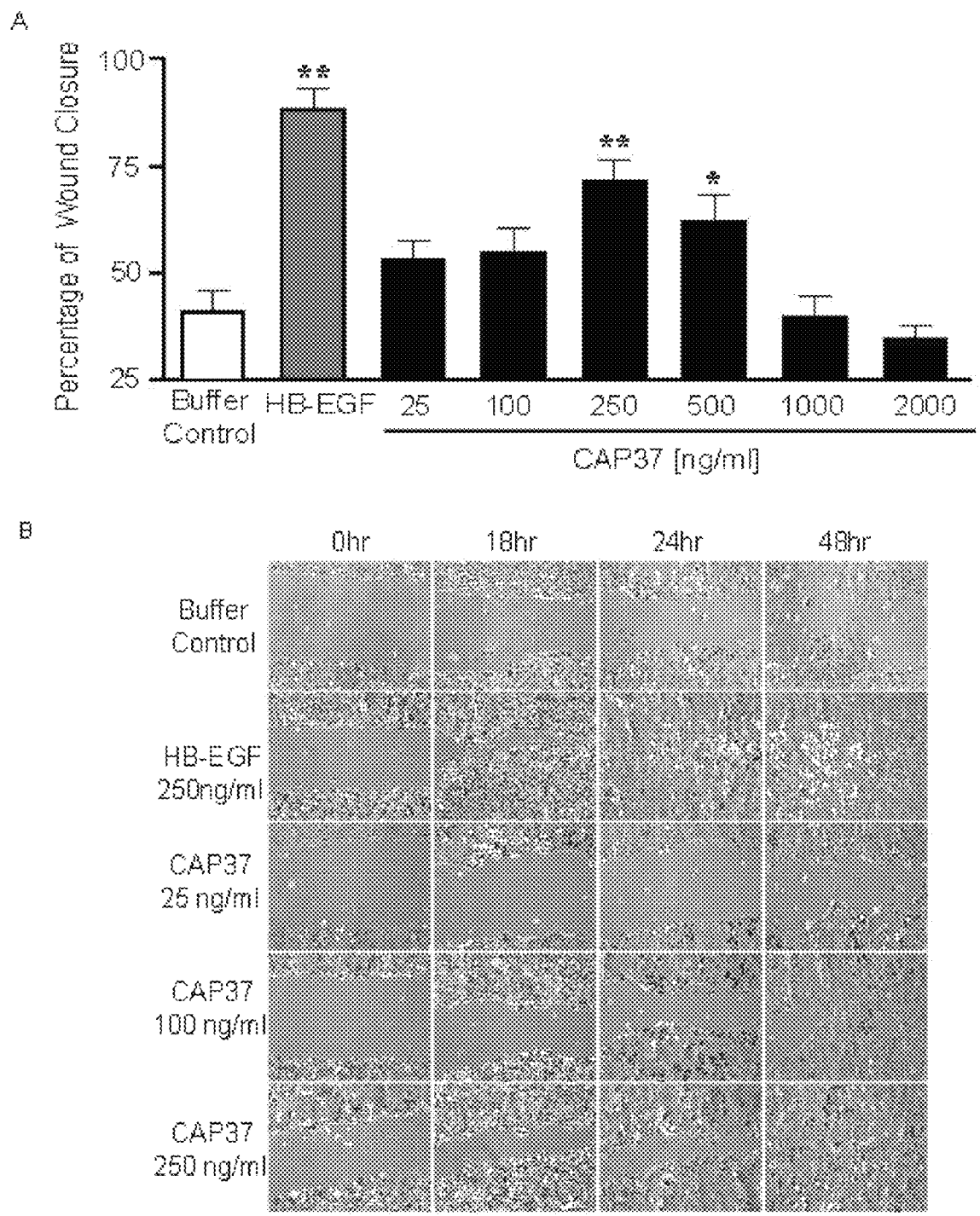
FIG. 21 shows that CAP37 increases wound closure in HCEC monolayers. (A) HCECs were grown to confluency and scratched using a 10 µl pipette tip. Scratched HCEC monolayers were treated with HB-EGF (250 ng/ml) or rCAP37 (25-2000 ng/ml), or were left untreated in basal Keratinocyte Serum Free Medium (KSFM). Wound closure was monitored at 0, 18, 24, and 48 hours utilizing a camera-equipped inverted microscope. The histogram represents data acquired at 48 hours, and the values are the mean±SEM of the percentage of wound closure. The data are representative of at least 4 independent experiments. The percentage of wound closure in treated monolayers was compared to untreated controls by one-way analysis of variance (ANOVA) followed by Dunnett's multiple comparison test, **P<0.01, *P<0.05. (B) Representative images of scratched monolayers treated with buffer control, HB-EGF, and rCAP37 (at 25, 100, and 250 ng/ml) are shown for each time point. Images were taken at 20× objective.

CAP37 facilitates wound closure in vitro: Previous studies have shown that CAP37 mediates HCEC proliferation, migration, and adhesion, leading the inventors to hypothesize that CAP37 may facilitate the process of corneal wound healing. To investigate this premise, an in vitro scratch model was utilized to determine if CAP37 could promote wound closure. The findings show that CAP37 promoted wound closure in vitro in a dose-dependent manner (FIG. 21, Panel A). CAP37 maximally facilitated wound closure when used at concentrations between 250 and 500 ng/ml. The percentage wound closure in CAP37-treated wounds with 250 ng/ml of CAP37 was almost 71% at 18 hours and was significantly greater (**$P<0.01$) than basal media-treated samples that showed approximately 41% closure. Treatment of wounds with 500 ng/ml of CAP37 resulted in approximately 62% closure and was significantly greater than the buffer control (*$P<0.05$). HB-EGF, which was used as the positive control, showed almost 88% closure of treated monolayers (FIG. 21, Panel A). Representative images of the in vitro scratch assay taken at each time point show the extent of closure in response to the various treatments. Wounds treated with HB-EGF were completely closed by 24 hours, whereas wounds treated with 250 ng/ml of CAP37 required between 24 to 48 hours for complete closure to occur. Buffer-treated wounds did not reach full closure at 48 hours of treatment (FIG. 21, Panel B).

Time-lapse microscopy studies of in vitro wound closure during the first 18 hours post wounding revealed differences in the manner in which the leading edge of cells responded to HB-EGF versus CAP37. In the CAP37-treated samples, it was noticed that individual cells would detach from the leading edge and crawl rapidly across the wounded area independent of the other cells. The cells showed polarization, with obvious lamellipodia indicative of activation. Not all cells at the leading edge showed activation or produced lamellipodia. However, the edge of the wound displayed more dynamic activity than the HB-EGF treated monolayers. HB-EGF-treated cells showed a strikingly different method of wound closure. These cells appeared to advance in a sheet, and individual cells did not detach or appear to migrate independently of the advancing sheet of cells across the wound. Morphological changes in the CAP37-treated cells, such as polarization and lamellipodia formation, were not as apparent in the HB-EGF or basal KSFM treated monolayers.

Figure 22:
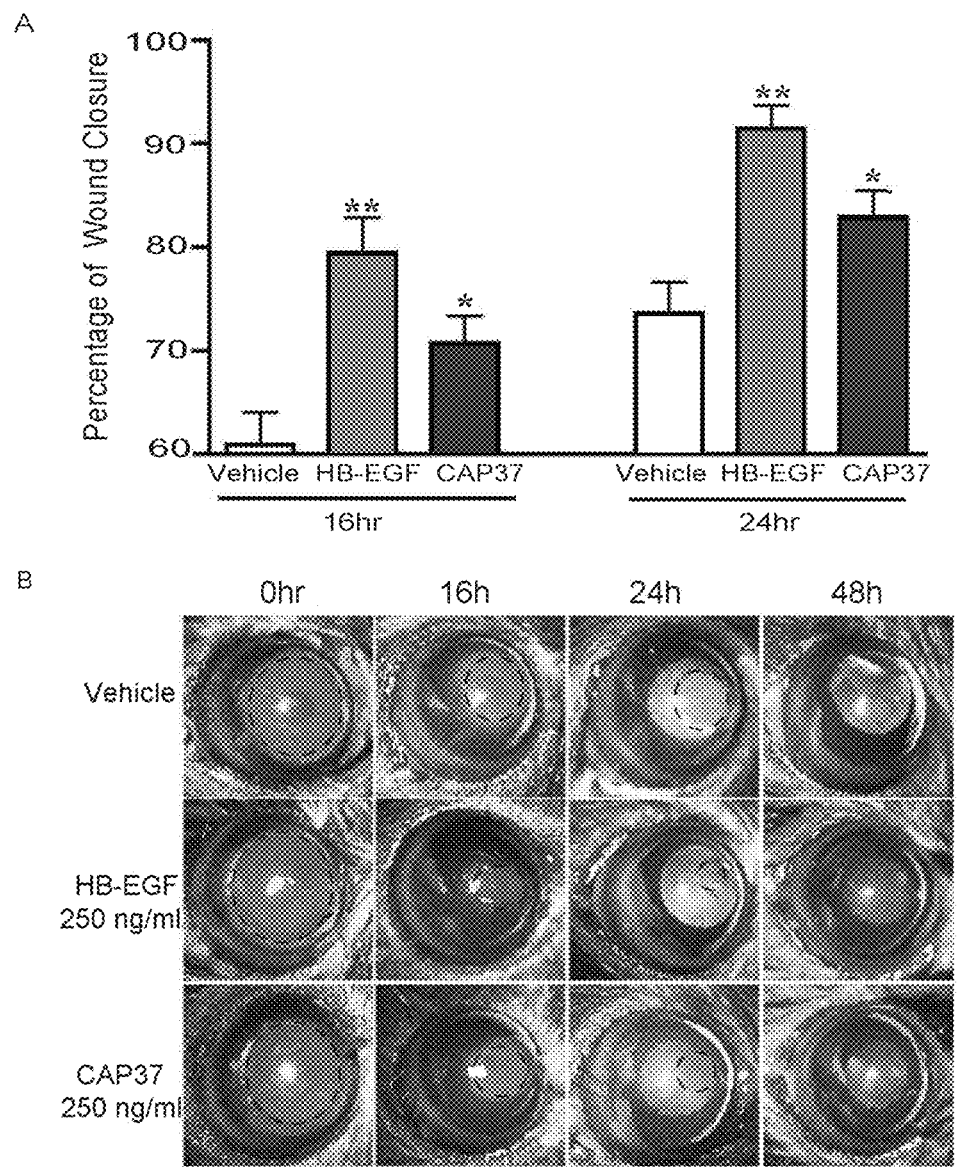
FIG. 22 shows that CAP37 promotes corneal epithelial wound healing in vivo. (A) The epithelium of the mouse cornea was removed using the AlgerBrush II, and corneal abrasions were treated at 0 and 16 hours with HB-EGF (250 ng/ml), rCAP37 (250 ng/ml), or vehicle control (normal saline). Wound closure was monitored at 0, 16, 24, and 48 hours using fluorescein staining and a camera-equipped inverted microscope. Data are represented as the percentage of wound closure and are expressed as mean±SEM. The data are representative of at least 6 mice per group. The percentage of wound closure in response to treatment was compared to vehicle-treated controls by unpaired t-test, **P<0.01, *P<0.05. (B) Representative images of mouse corneal wounds are shown at 0, 16, 24, and 48 hours following treatment with vehicle, HB-EGF, and CAP37. Black dotted lines indicate the wound edge.

CAP37 facilitates corneal wound healing in an in vivo mouse model: Using the in vivo mouse model of corneal wound healing described in the materials and methods section, the effect of topical application of CAP37 on wound closure was explored, and the rate of closure at 16, 24, and 48 hours was compared with the positive control HB-EGF and the negative vehicle control (FIG. 22, Panels A and B). At 16 hours, CAP37 had effectively reduced the size of the wound by 71%, and by 24 hours the CAP37-treated (250 ng/ml) wounds were 83% closed. At both time points, the CAP37 treated wounds were closed significantly more than the vehicle treated controls (*$P<0.05$ compared to the buffer control). A time dependent closure of wounds was also demonstrated with HB-EGF and was significantly higher compared to the buffer control (**$P<0.01$). Representative images of fluorescein stained wounds are shown in Panel B of FIG. 22 and demonstrate the time-dependent healing of the wounds in response to treatment with vehicle, HB-EGF and CAP37. As can be seen, all wounds indicated complete closure by 48 hours, as measured by fluorescein staining (FIG. 22, Panel B).

Figure 23:
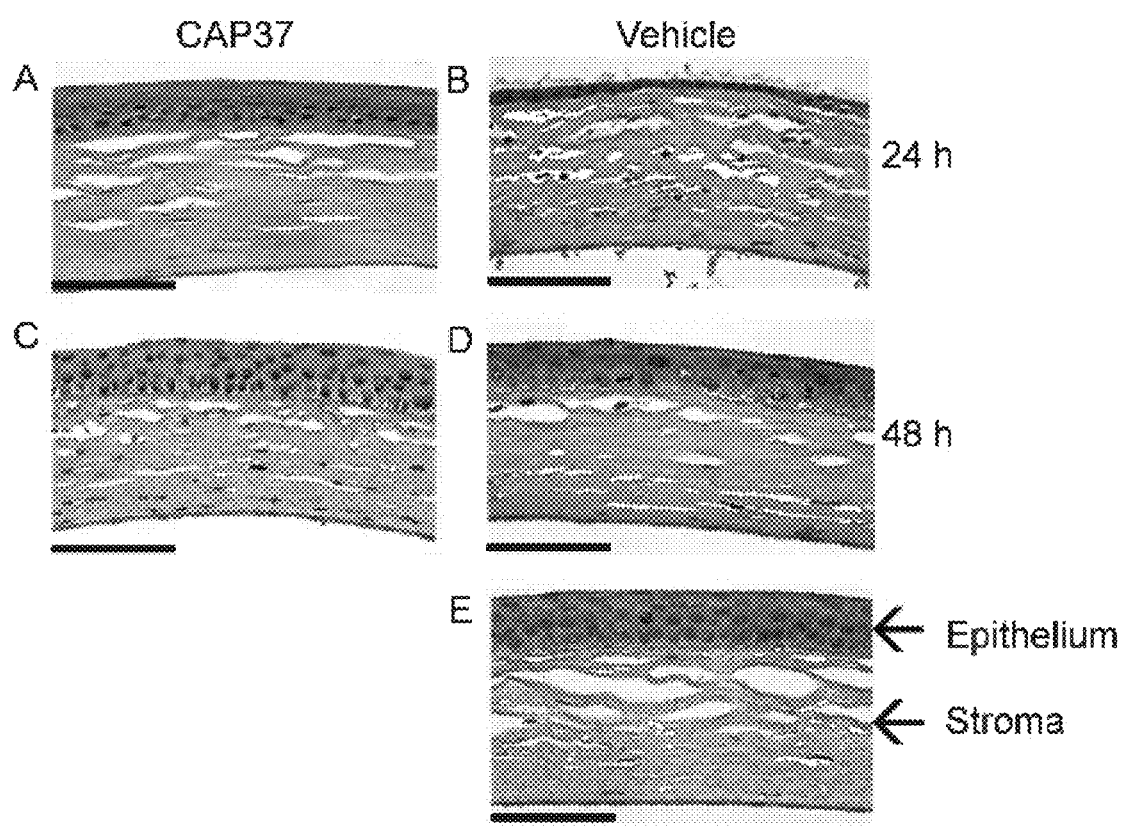
FIG. 23 is a histological analysis of corneal wound closure and re-epithelialization in response to CAP37. Corneas of mice were wounded using the Algerbrush II and treated at 0 and 16 hours with rCAP37 (250 ng/ml) or vehicle (normal saline). Whole eye globes were enucleated at 0, 24, and 48 hours post wounding, and sections were stained using hematoxylin and eosin (H&E). Representative images are shown of (A) CAP37-treated wound at 24 hours, (B) vehicle-treated wound at 24 hours, (C) CAP37-treated wound at 48 hours, and (D) vehicle treated wound at 48 hours. The extent of closure and re-epithelialization of wounds was compared with (E) normal unwounded cornea.

CAP37 leads to corneal re-epithelialization by 24 hours: The fluorescein staining method provides a gross morphologic approach to determine the extent of corneal abrasion and healing. However, to determine whether CAP37 promotes complete re-epithelialization and restores the structural integrity of the epithelial layers of the cornea, whole eye globes were collected at 16, 24, and 48 hours and processed for histology (FIG. 23, Panels A-E). Hematoxylin and eosin (H&E) stained sections revealed that re-epithelialization was well underway by 24 hours with restoration of the basal cell layers of the epithelium, indicating the proliferation of these cells in response to treatment with CAP37 (FIG. 23, Panel A). The migration and differentiation to squamous cells at 24 hours in response to CAP37 did not appear to be complete, possibly accounting for the detection of the low level of fluorescein staining at 24 hours shown in Panel B of FIG. 22. The re-epithelialization in response to CAP37 was greatly accelerated in comparison to the vehicle-treated wounds at 24 hours (FIG. 23, Panel B). As can be seen, the epithelium was only a single-layer thick in the central region of the wound, and proliferation of the basal cells was limited in comparison to the CAP37-treated wounds at this same time point. This is further confirmed in the fluorescein-stained wounds in Panel B of FIG. 22, showing that the vehicle-treated wounds had much stronger staining. At 48 hours, the CAP37-treated wounds (FIG. 23, Panel C) had regained full integrity and could not be histologically differentiated from the unwounded corneas (FIG. 23, Panel E). Although the vehicle-treated cornea had re-epithelialized by 48 hours, complete structural integrity of the apical layers was not observed (FIG. 23, Panel D).

Figure 24:
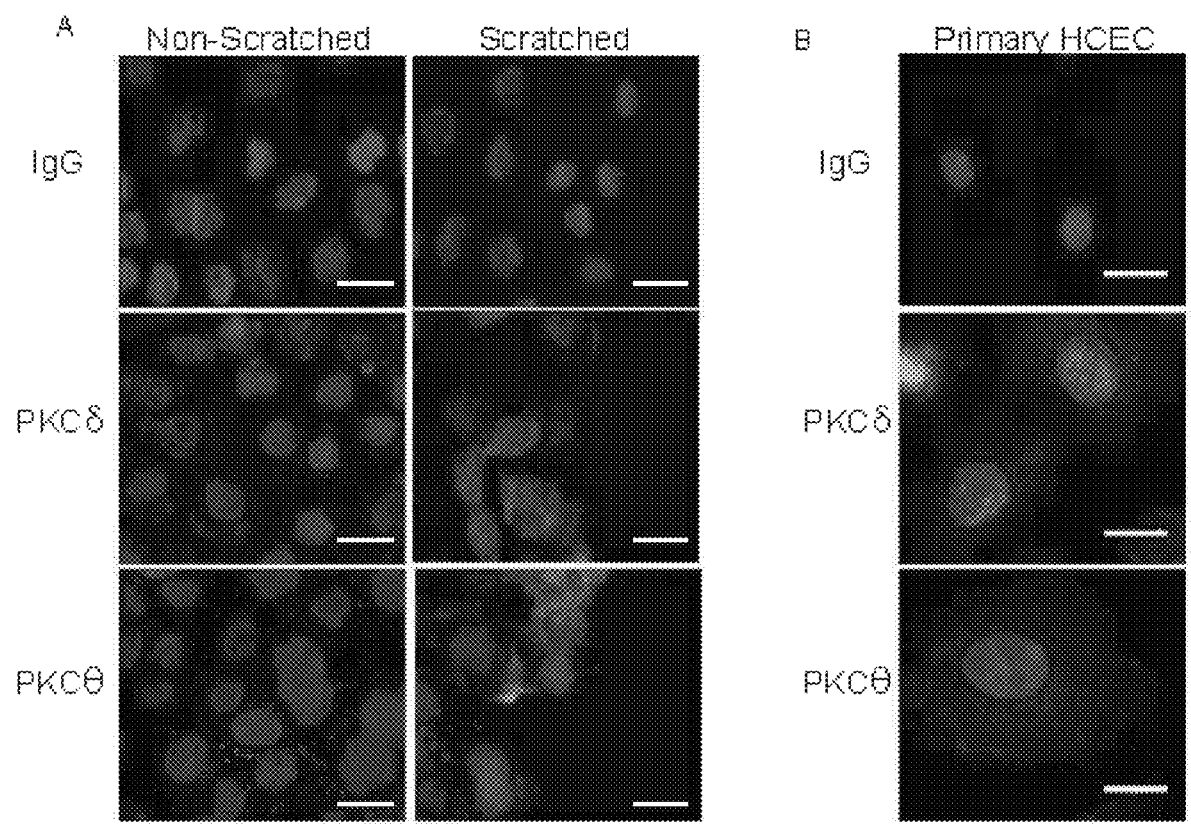
FIG. 24 shows that Protein Kinase C-delta (PKCδ) and Protein Kinase C-theta (PKCθ) are expressed in wounded and non-wounded HCEC monolayers. (A) HCECs (SV40 adenovirus immortalized cell line) were grown to confluency and were scratched with a 10 μl pipette tip (right hand panel) or left unscratched (left hand panel). Monolayers were stained for PKC isoforms at 2 hours post wounding using anti-PKCδ antibody (250 ng/ml), anti-PKCθ antibody (500 ng/ml), or IgG control (500 ng/ml), and anti-mouse secondary antibody (4 μg/ml, ALEXA FLUOR® 488 dye (Life Technologies Corp., Grand Island, N.Y.)). Representative images are shown. Scale bars, 20 μm. (B) Primary HCECs were stained to demonstrate constitutive expression of PKC isoforms δ and θ in unwounded monolayers. Representative images are shown. Scale bars, 20 μm.

PKCδ and PKCθ are present in wounded HCEC monolayers: Studies by the inventors show that PKC isoforms α, δ, ε, θ, η, ι, λ, and ζ are expressed in human corneal epithelial cells and that CAP37 specifically activates PKC δ and θ during chemotaxis. Since migration of epithelial cells is an important step in normal wound healing, it was questioned whether these isoforms were involved in wound healing. Unscratched and scratched HCEC monolayers were stained for the expression of PKC δ and θ. Results showed the constitutive expression of PKC isoforms δ and θ in unscratched HCEC monolayers and demonstrated the increased staining of both isoforms along the wound edge (FIG. 24, Panel A). The constitutive expression of PKC isoforms δ and θ was confirmed using primary HCECs (FIG. 24, Panel B). The specificity of the staining for these two isoforms in the SV40 HCEC cell line and primary HCECs was demonstrated using an IgG antibody control which showed no staining.

Figure 25:
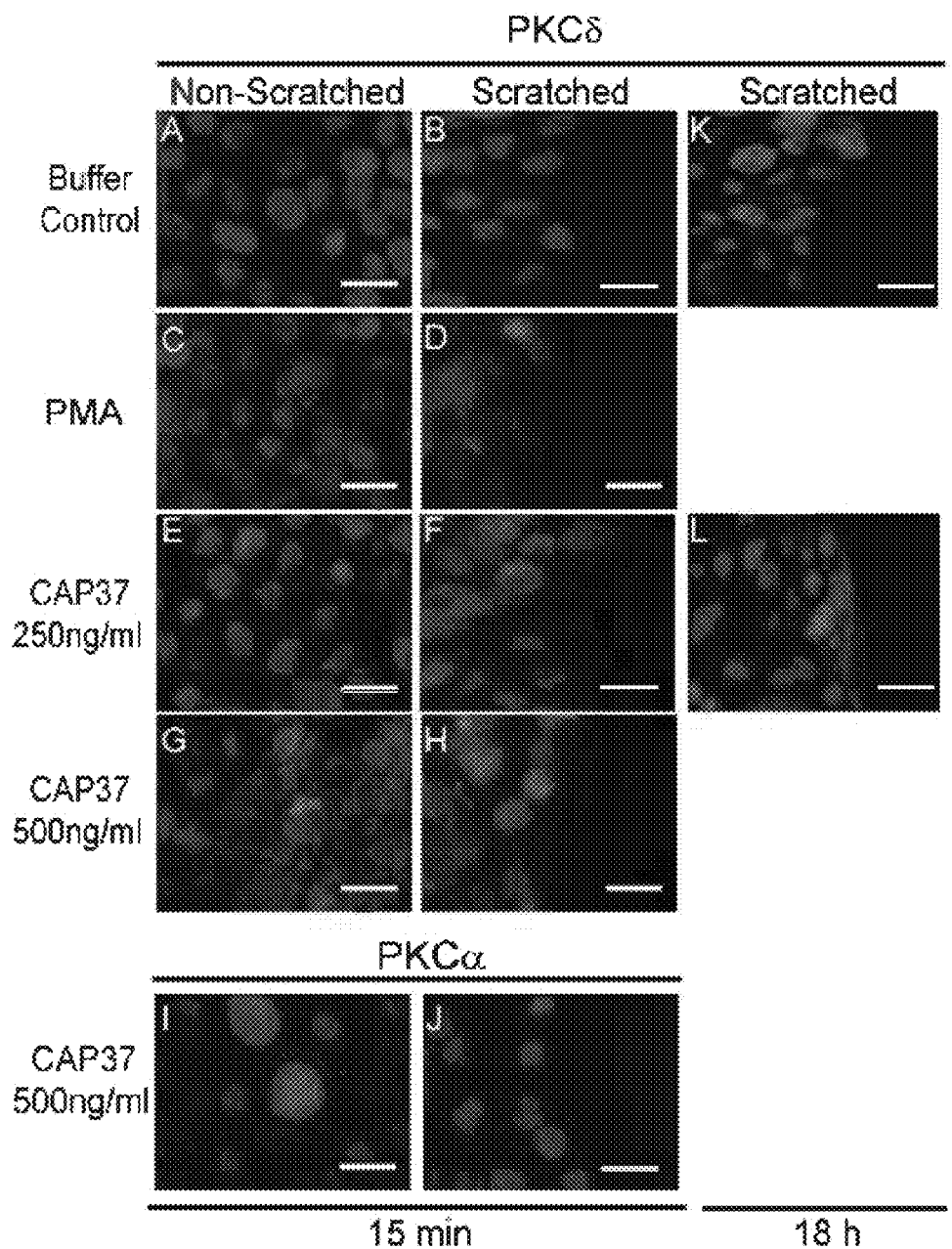
FIG. 25 shows that CAP37 treatment leads to an increase in PKCδ staining in HCEC monolayers. HCEC monolayers were grown to confluency and were scratched with a 10 μl pipette tip or left unscratched, and then the monolayers were treated for 15 minutes with (A-B) buffer, (C-D) PMA (1 μM), (E-F) 250 ng/ml CAP37, and (G-J) 500 ng/ml CAP37. Cells were stained for PKCδ (250 ng/ml; (A-H)), and PKCα (1 μg/ml; (I-J)) and detected using immunofluorescence (4 μg/ml, ALEXA FLUOR® 488 dye (Life Technologies Corp., Grand Island, N.Y.)). Representative images (C—H) show staining for PKCδ in non-scratched monolayers (C, E, and G) and increased staining in scratched monolayers (D, F, H) in response to PMA and CAP37. However, no increase in PKCα staining was observed following treatment of CAP37 (I-J). Scratched monolayers that were treated for 18 hours with CAP37 (250 ng/ml; (L)) or left untreated (K) were stained for PKCδ. Treatment with CAP37 showed marked staining along the wound edge was observed. Scale bars, 20 μm.

CAP37 treatment leads to an increase in PKCδ staining in HCEC monolayers: PKCδ was selected for further investigation in CAP37-mediated corneal wound healing. To determine if CAP37 had an effect on PKCδ expression in HCEC monolayers that were unscratched and scratched, HCECs were treated with CAP37 (250 and 500 ng/ml) and a positive control, PMA. A dose-dependent increase in PKCδ staining was seen at 15 minutes in CAP37-treated cells in both non-scratched (FIG. 25, Panels E and G) and scratched (FIG. 25, Panels F and H) monolayers over untreated non-scratched (FIG. 25, Panel A) and scratched (FIG. 25, Panel B) monolayers. The increase in PKCδ staining appeared to be dose-dependent, with greater staining observed following treatment with 500 ng/ml of CAP37. The increase in PKCδ staining in response to CAP37 was sustained for at least 18 hours (FIG. 25, Panel L) versus the untreated control (FIG. 25, Panel K). The expression of PKCδ was comparable between CAP37-treated cells (FIG. 25, Panels E-H) and PMA-treated cells (FIG. 25, Panels C and D). To establish that this increased expression in response to CAP37 treatment was specific for PKCδ, staining for the a isoform of PKC was also performed, but no increase in PKCα staining was found either within the monolayer (FIG. 25, Panel I) or along the wound edge (FIG. 25, Panel J) of the monolayer when treated with CAP37.

Figure 26:
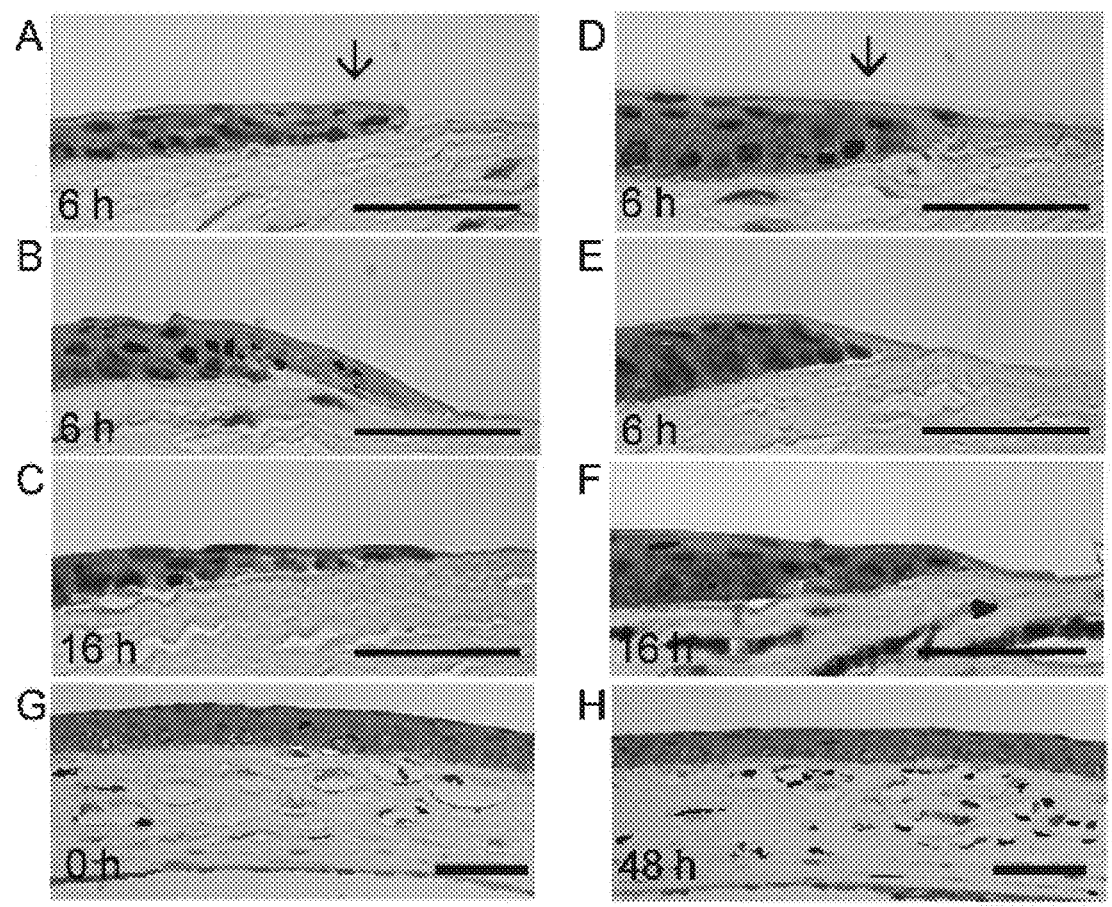
FIG. 26 shows that PKCδ is expressed along the leading edge of corneal epithelial wounds in vivo. Mice corneas were wounded using the AlgerBrush II and treated at 0 and 16 hours with vehicle (normal saline; (A-C)) or rCAP37 (250 ng/ml; (D-F)). Whole eye globes were enucleated at 6 hours (A, B, D, E), 16 hours (C, F), and 48 hours (H) post-wounding, and sections were stained for PKCδ. Representative images show constitutive staining for PKCδ in unwounded corneas (G). A lack of strong staining was seen at the leading wound edge (↓) in vehicle treated corneas at 6 hours (A, B) and 16 hours (C). Pronounced staining for PKCδ was seen along the leading wound edge (↓) in CAP37-treated corneas at 6 hours (D, E) and 16 hours (F). The presence of PKCδ was still seen 48 hours after wounding (H) and was comparable to the constitutive staining seen at 0 hours in the unwounded cornea (G). Scale bars, 100 μm.

PKCδ is expressed along the wound edge in vivo: Since staining for PKCδ was increased in response to wounding in cultured HCEC monolayers (FIG. 24, Panel A), studies were performed to determine whether an increase in expression of PKCδ would be seen in corneal wounds in vivo. Corneas were abraded as described previously, and the whole mouse eye globes were collected at 6, 16, and 48 hours post wounding for immunohistochemistry in order to determine the expression of PKCδ in response to wounding. Little to no detection of PKCδ was observed at the leading edge of the newly proliferating and migrating epithelial cells at 6 hours (FIG. 26, Panels A-B) and 16 hours (FIG. 26, Panel C) post wounding. However, the epithelial cells at a distance from the leading edge showed a low level of staining that was comparable to the constitutive expression of PKCδ in normal unwounded cornea (FIG. 26, Panel G).

To determine if CAP37 treatment of the wounds had an effect on PKCδ expression, corneas were wounded and treated immediately and 16 hours following wounding. Eyes that were enucleated at 6 and 16 hours had one treatment of CAP37 (0 hours) whereas the eyes that were enucleated at 48 hours were treated twice with CAP37 (0 and 16 hours). Sections stained at 6 hours showed strong staining for PKCδ in the newly migrating and proliferating epithelial cells as well as those cells distant from the wound edge (FIG. 26, Panels D-E). A similar staining pattern for PKCδ was seen in sections that were obtained at 16 hours post wounding (FIG. 26, Panel F). Sections that were obtained at 48 hours were completely healed and showed uniform staining throughout the epithelium (FIG. 26, Panel H) and was at an intensity similar to constitutive expression in unwounded corneas (FIG. 26, Panel G).

Figure 27:
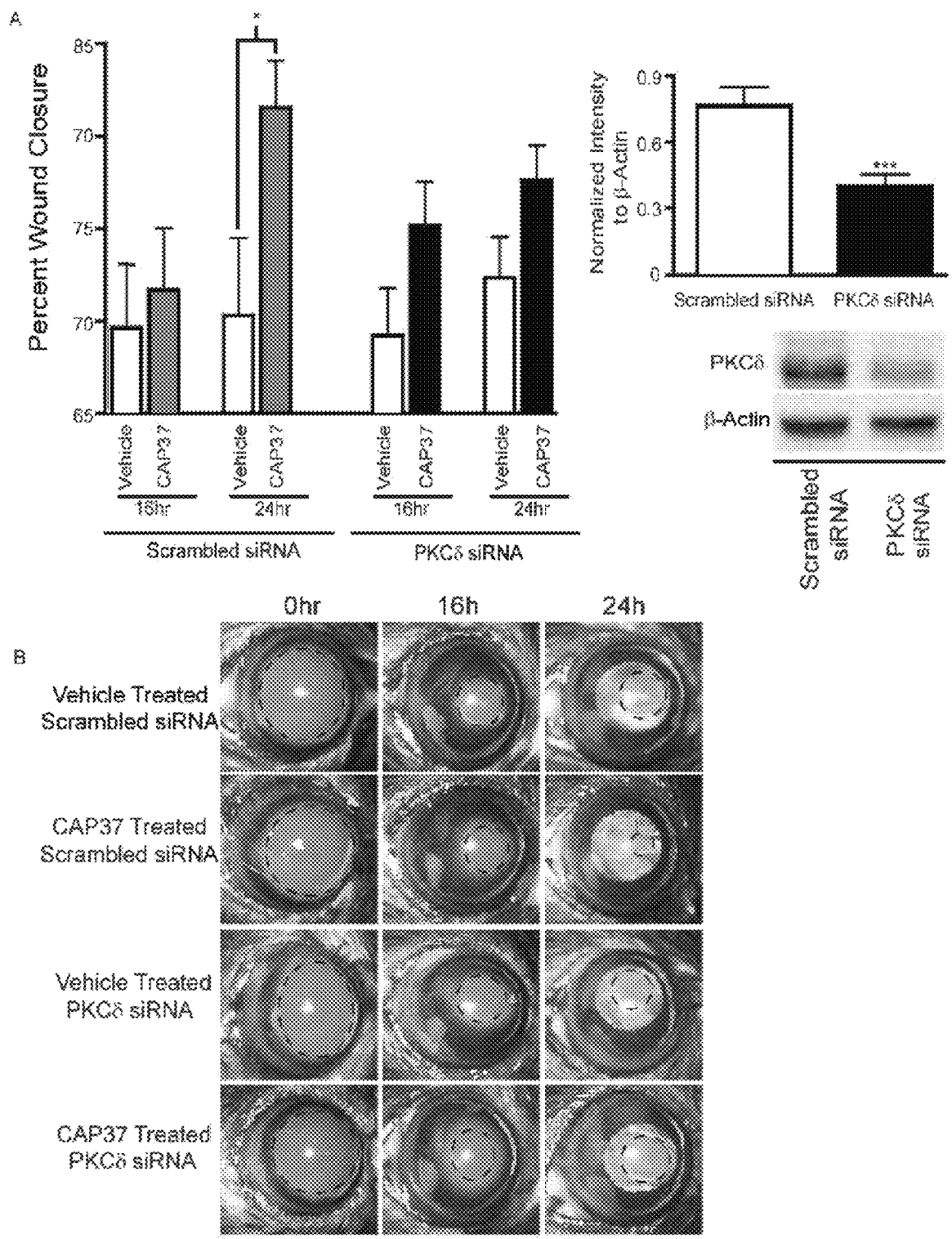
FIG. 27 shows that PKCδ is necessary for CAP37-induced wound healing in vivo. (A) siRNA directed against PKCδ or scrambled siRNA was injected into the mouse conjunctiva. The mouse corneal epithelium was removed with the AlgerBrush II. Corneal abrasions were treated at 0 and 16 hours with rCAP37 (250 ng/ml), or were left untreated (saline vehicle control). Wound healing was monitored at 0, 16, and 24 hours using fluorescein staining. Data are represented as the percentage of wound closure and are expressed as mean±SEM. The data are representative of at least 9 mice per group. *P<0.05 by unpaired t-test as compared to vehicle (normal saline) treated controls. The efficiency of the PKCδ knockdown in each cornea was confirmed by Western blot analysis 24 hours post-injection and determined in comparison to the scrambled siRNA-injected corneas. Data are representative of 22 experimental samples and are expressed as mean±SEM (***P<0.0005 by unpaired t-test). (B) Representative images stained with fluorescein indicating extent of closure of corneal abrasions at 0, 16, and 24 hours. The dotted line is used to demarcate the edge of the wound.

PKCδ is necessary for CAP37 wound healing in vivo: In vivo experiments were performed using siRNA to determine if CAP37 mediates wound healing via PKCδ. Mouse corneas were transfected with siRNA directed against PKCδ or with scrambled siRNA. Wounds were created as described following transfection with scrambled siRNA and PKCδ siRNA. Corneas were then treated with the vehicle or CAP37 (250 ng/ml), and wound closure was measured at 16 and 24 hours. Corneas transfected with scrambled siRNA showed the expected increase in wound closure following CAP37 treatment at 24 hours (P<0.05) (FIG. 27, Panel A). In corneas transfected with PKCδ siRNA, there was no significant increase in wound healing in response to CAP37 (FIG. 27, Panel A) at either the 16 or 24 hour time points. CAP37 treatment did lead, however, to a slight increase in wound healing over saline treated wounds, but this increase did not reach statistical significance (FIG. 27, Panel A). This could indicate that PKCδ is not the only signaling molecule involved, but is more likely a reflection that the knockdown of PKCδ in each cornea, as assessed by Western blot, was on average 50% (FIG. 27, Panel A). The level of knockdown was determined to be statistically significant (***P<0.005) when compared with the scrambled siRNA controls. Representative images of fluorescein stained wounds depict the extent of wound closure over time in corneas transfected with scrambled siRNA and treated with CAP37 (FIG. 27, Panel B). As can be seen, maximum wound closure was observed in animals that were transfected with scrambled siRNA and treated with CAP37.

These results demonstrate a novel function for the neutrophil-derived protein CAP37, also known as heparin binding protein and azurocidin. Using a series of in vitro and in vivo models of wound healing, it was shown that CAP37 accelerates wound closure in vitro as well as in a mouse model of corneal abrasion. Importantly, the mechanism whereby CAP37 facilitates corneal epithelial wound healing has been identified. By employing immunohistochemical and siRNA techniques, it was established that the protein kinase C (PKC) signaling pathway, specifically PKCδ, is the key modulator of CAP37-mediated corneal epithelial wound healing. This appears to be the first demonstration of an intracellular signaling mechanism employed by a neutrophil granule-derived antimicrobial protein in corneal epithelial wound healing.

The cornea is an immune privileged site, and therefore the process of healing in the cornea is not identical to the process that occurs in dermal skin wounds. However, one key feature in both corneal and dermal wound healing is that neutrophils are an essential cellular component. Neutrophils are early participants in the process and are fundamental to protecting the host from infection due to their potent antimicrobial and phagocytic activity. When the cornea is injured, neutrophils migrate through the limbal vessels into the cornea. Studies have shown that delayed corneal wound healing occurs in mice with antibody-induced neutropenia. Other studies using wild type and knockout mice for lumican and heme oxygenase, and rabbit models of corneal epithelial wound healing, have further established that the presence of neutrophils accelerates healing. This led the inventors to the concept that antimicrobial proteins found within the granules of neutrophils such as CAP37, LL-37, human β-defensin-1 (HBD-1), and bactericidal-permeability-increasing (BPI) protein may prove to be useful in modulating wound closure.

Neutrophils that are recruited to the wound site release their granule contents, including CAP37 and other antimicrobial proteins and peptides, which provide the first line of defense against corneal infection. It is now known that these antimicrobial peptides, in addition to killing the invading pathogens, are able to modulate functions of host cells that regulate innate immunity. Importantly, the neutrophil is not the only source of these antimicrobial proteins. CAP37 and LL-37 can be induced in host cells, including the corneal epithelium, in response to infection and wounding. LL-37 has been shown, like CAP37, to be antimicrobial, bind lipopolysaccharide, and promote corneal epithelial wound healing in vitro. Unlike CAP37, LL-37 does not promote HCEC proliferation, and the intracellular signaling mechanisms involved in its effects on corneal epithelial cell migration and wound healing have not been elucidated.

This Example not only confirmed that HB-EGF promotes wound healing in vitro, but also revealed for the first time that HB-EGF promotes corneal wound healing in vivo. HB-EGF was selected for use as a positive control, as it is also a heparin binding protein like CAP37 and because there is in vitro evidence that HB-EGF facilitates corneal wound healing in organ tissue cultures. Previous in vitro studies have indicated that HB-EGF, but not EGF, facilitates corneal wound healing through the prolonged activation of the EGF receptor. This is believed to be due to the fact that HB-EGF is able to bind to the negatively charged glycans on the corneal surface, while EGF is washed away after treatment. The heparin binding characteristics of HB-EGF that make it desirable as a long acting alternative to EGF also apply to CAP37, making it an effective therapeutic for ocular wound healing.

Without wishing to be bound by theory, the present work indicates that the CAP37-mediated cellular processes, previously defined as proliferation, migration, and adhesion, are working in conjunction to facilitate corneal epithelial wound healing. Time-lapse videos of CAP37-treated in vitro wounds infer that CAP37 affects corneal epithelial wound healing by primarily facilitating migration, at least in the early stages of wound repair. Other mechanisms, such as proliferation and adhesion, may be involved at later stages of the process.

One component of the work was the delineation of the intracellular signaling mechanism that evoked CAP37-mediated corneal epithelial wound healing. After demonstrating the ability of CAP37 to mediate corneal wound closure in vitro and in vivo (FIGS. 21-22), the presence of PKCδ was identified in untreated corneal epithelial cell culture monolayers and confirmed in primary corneal epithelial cells (FIG. 24). CAP37-treated corneal epithelial cell monolayers showed an increase in staining for PKCδ (FIG. 25) that persisted up to 18 hours after CAP37 treatment, indicating that the effect was not transient. While immunohistochemistry revealed the constitutive presence of PKCδ in unwounded mouse corneas, immunohistochemistry of CAP37-treated wounds revealed an increase in PKCδ staining along the leading edge of the wound at both 6 hours and 16 hours compared to vehicle-treated controls (FIG. 26). The presence of PKCδ along the wound edge and an increase in PKCδ in CAP37-treated wounds prompted studies in which PKCδ was knocked down in a mouse model of corneal epithelial wound healing. Results revealed that a partial knockdown of PKCδ is sufficient to reduce the effect of CAP37 on corneal wound healing in vivo. While the PKCδ knockdown did not entirely ablate the effects of CAP37, and there was no significant difference between the CAP37 treated wounds transfected with scrambled or PKCδ siRNA at either time point, the decrease in wound healing may still have a significant impact clinically (FIG. 27). The average PKCδ knockdown achieved was 50% and could explain why CAP37 still promoted a certain amount of wound closure in corneas transfected with siRNA directed against PKCδ. Another explanation for these findings is that other PKC isoforms such as PKCθ may partially contribute to CAP37-mediated wound healing. Others have shown that PKCα and PKCε are important in HGF-induced corneal wound healing, and that PKCα is a key modulator in rabbit corneal wound healing. In contrast, studies using PKCα knockout mice have demonstrated more rapid corneal epithelial wound healing, and the inventors indicate that this is perhaps due to fewer infiltrating neutrophils in this model. The studies with CAP37 did not show the involvement of PKCα. As with all inflammatory reactions, a fine balance exists between limiting the influx of inflammatory cells and promoting the healing process.

An interesting observation in FIG. 26 was the staining of the emigrating leukocytes in addition to the staining of PKCδ at the leading edge of CAP37 treated corneal wounds. Neutrophils are known to express PKCδ, which is required for the full NADPH oxidation and respiratory burst activation in neutrophils. Studies have shown that antimicrobial proteins such as LL-37 can induce the production of reactive oxygen species (ROS) in neutrophils in a time- and dose-dependent manner through the NADPH oxidase system. This is of particular relevance in terms of wound healing, because low levels ($10^{-20}$ μM) of hydrogen peroxide ($H_2O_2$) have been shown to induce corneal wound healing through the promotion of adhesion and migration of corneal epithelial cells. Unpublished results from the inventors showed that CAP37 increases the production of ROS in microglia and monocytes, cells in which CAP37 also mediates chemotaxis. It was also recently demonstrated that the NADPH oxidase is expressed in HCECs, and that these cells are also capable of producing superoxide through this enzymatic complex. Taken together, these studies indicate that CAP37 induces the expression of PKCδ in the corneal epithelium cells at the edge of the wound, thereby locally activating the NADPH oxidase and the production of ROS to facilitate wound healing.

Example 8

Synergism between BCC002-5RMP (SEQ ID N0:21) and Low Dosage Antibiotics.

Traditional efforts to counter antibiotic resistance have relied upon making incremental changes to existing drugs. This strategy provides short-term relief, but bacteria quickly develop resistance to these slight modifications. A serious gap exists in the drug development pipeline for safe and effective therapies for treating infections due to multidrug resistant Gram negative organisms. As discussed elsewhere herein, the peptide compounds of the presently disclosed inventive concepts contributes to the alleviation of this major healthcare problem as a new class of anti-infectives for the treatment of serious infections due to Gram negative pathogens, such as but not limited to, *Pseudomonas* sp., *Acinetobacter* sp., *Salmonella* sp., and *E. coli*. The presently disclosed inventive concepts thus include as embodiments a method of enhancing the efficacy of an antibiotic in the treatment of a bacterial infection. In the method, the antibiotic and the presently disclosed peptide compound are administered; the antibiotic is administered in an amount which (i) has suboptimal activity or is ineffective against the bacteria when administered alone, and (ii) is effective against the bacteria when administered in combination with the peptide compound.

The present therapeutic treatment uses, in at least one embodiment, the presently disclosed peptide compounds (e.g., BCC002-5RMP (SEQ ID NO:21)) to potentiate (enhance) the effect of standard of care antibiotics, making these antibiotics effective against resistant bacteria at dosage levels previously considered to be suboptimal or ineffective. These findings are significant because, if existing antibiotics can be used at a lower dose (suboptimal or <MIC), they are less likely to be toxic; in addition, when an existing antibiotic is administered at a lower dose (suboptimal or <MIC) and in combination with a peptide compound of the presently disclosed inventive concepts, bacteria are less likely to develop resistance to the antibiotic as compared to when the lower dose of antibiotic is administered on its own. Thus, administration of an antibiotic in combination with a peptide compound of the presently disclosed inventive concepts is more likely to extend the length of time the antibiotic can be used in the clinical setting.

The importance of these findings as explained above is that the presently disclosed peptide compounds, such as but not limited to BCC002-5RMP (SEQ ID NO:21), can potentiate the effect of standard of care antibiotics such that they can be used at a lower dose (suboptimal or <MIC) and regain their activity against organisms that have become resistant to it. In other words, the organism can be re-sensitized to antibiotics that were once thought to be ineffective against the organism due to resistance thereto.

Data in support of this result are shown in FIGS. 28-30. A clinical isolate of *P. aeruginosa* that was resistant to Levofloxacin and Ciprofloxacin with intermediate sensitivity to Cefotaxime was selected. The peptide and antibiotics were set up in the wells of the microtiter plate at starting ratios of MIC equivalents of antibiotic:peptide at 3:1, 1:1, and 1:3. They were serially diluted to concentrations well below suboptimal/sublethal levels of the antibiotic and peptide. The organism was added ($1 \times 10^5$ CFU/well), the BIO-SCREEN C™ assay (Growth Systems USA, Piscataway, N.J.) was performed, and data was collected over 24 hours. The results showed that although this organism was resistant to Ciprofloxacin (MIC of 8.4 µg/ml), Levofloxacin (MIC of 15 µg/ml), and Cefotaxime (MIC of 15 µg/ml), it was possible to make the *Pseudomonas* isolate sensitive to each of these antibiotics at a suboptimal/sublethal dose with the addition of the peptide.

Figures 28A, 28B:
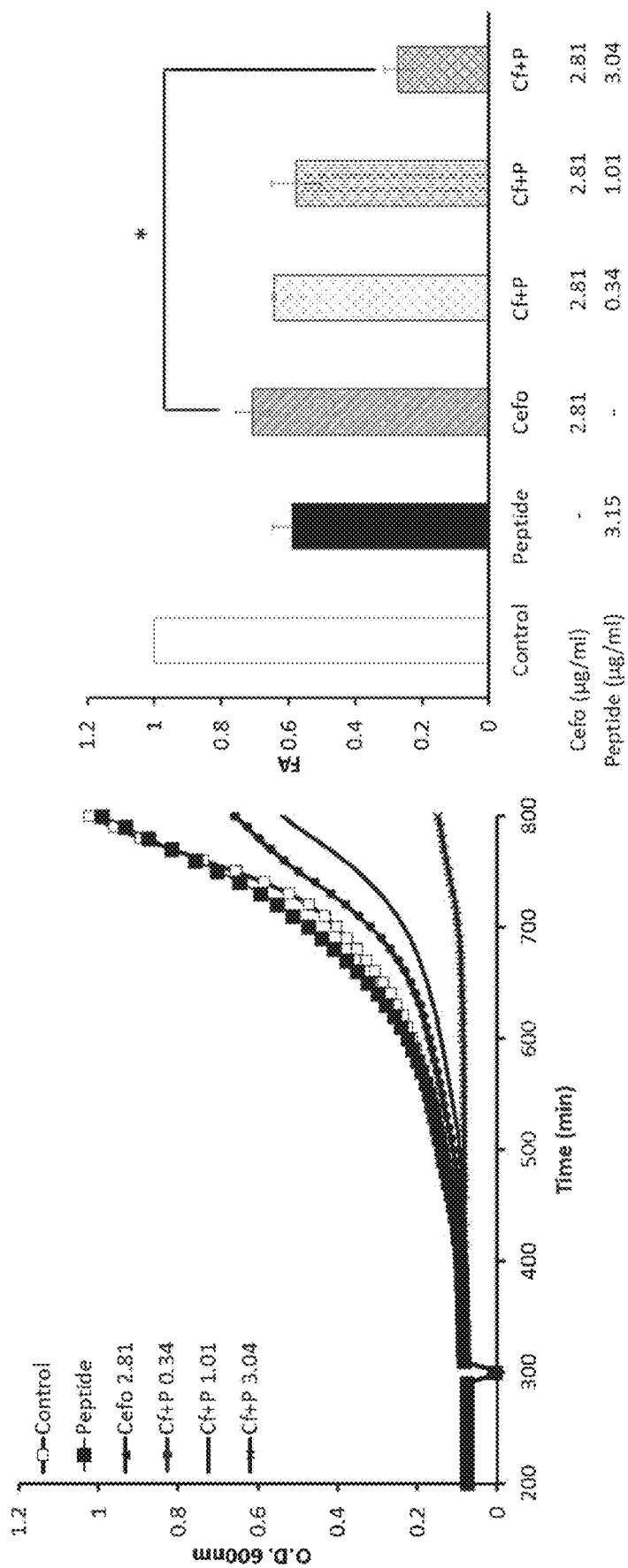
FIGS. 28A and 28B show the effect of BCC002-5R-MP (SEQ ID NO:21) in combination with Cefotaxime on MIC using Pseudomonas clinical isolate B64. Cefotaxime (Cefo) and peptide combinations included a constant amount of Cefotaxime (2.81 μg/ml) with suboptimal amounts of peptide (0, 0.34, 1.01, and 3.04 μg/ml).

For example, FIG. 28A shows the growth/survival curve of the organism in the presence of Cefotaxime at a sublethal concentration of 2.81 µg/ml, and growth curves with combinations of Cefotaxime at 2.81 µg/ml and peptide at 0.34, 1.01, and 3.04 µg/ml. The growth of the organism in the presence of peptide on its own at 3.15 µg/ml is shown. The growth of the *Pseudomonas* in the absence of peptide and antibiotic is also shown. As will be seen from the growth curve as well as the histogram showing fractional area (FA) (FIG. 28B), the addition of 2.8 µg/ml of Cefotaxime had very little bactericidal impact on the organisms, as growth in the presence of the antibiotic was very similar to the control growth curve. The addition of 0.34 and 1.0 µg/ml of peptide BCC02-5RMP (SEQ ID NO:21) had no statistical effect on the killing effect of the antibiotic. However, on the addition of 3.04 µg/ml of peptide, it was apparent that the bacterium with intermediate sensitivity to Cefotaxime was now sensitive (P=0.0143 by unpaired t test). This shows that when CAP37-based peptide compounds were used in combination with standard antibiotics, the therapeutic dose of the standard antibiotic was lowered, thus making a resistant organism sensitive to therapy.

Figures 29A, 29B:
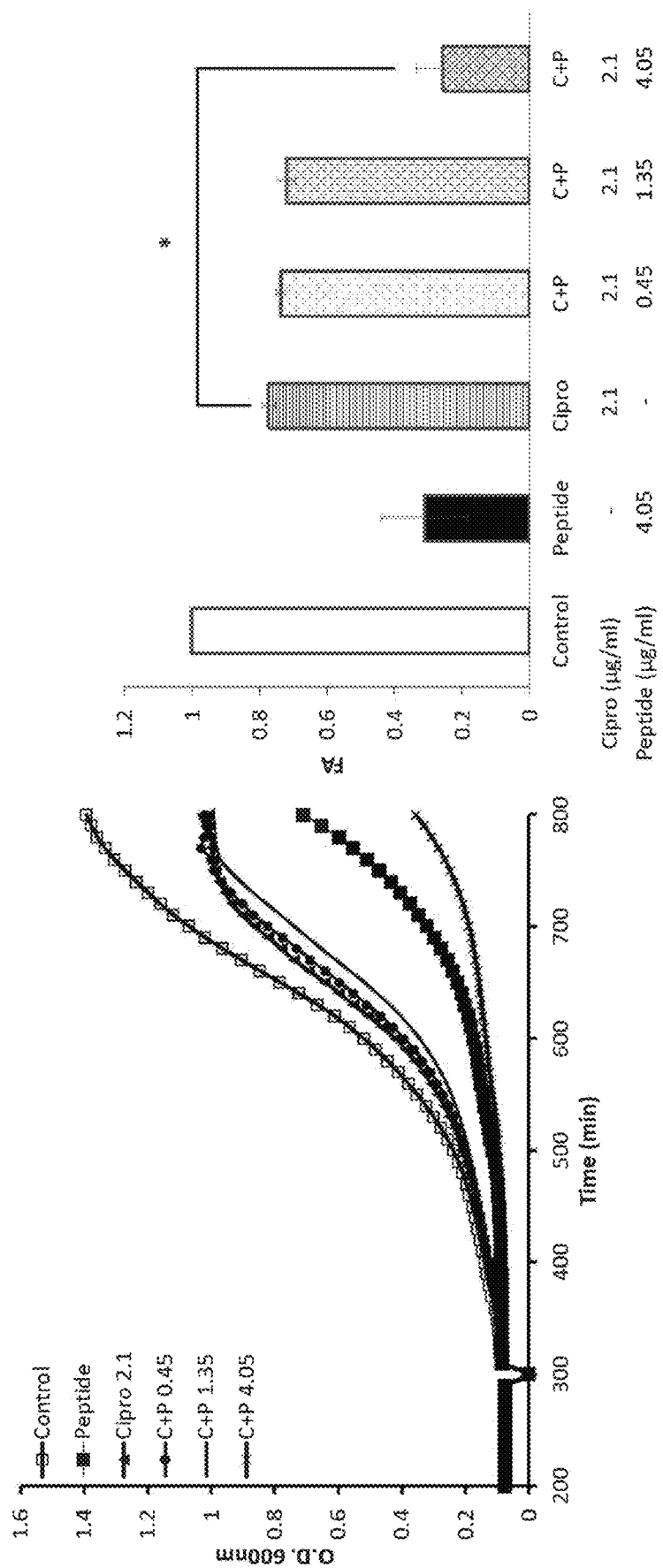
FIGS. 29A and 29B show the effect of BCC02-5R-MP (SEQ ID NO:21) in combination with Ciprofloxacin on MIC using Pseudomonas clinical isolate B64. Ciprofloxacin (Cipro) and peptide combinations included a constant amount of ciprofloxacin (2.1 μg/ml) with suboptimal amounts of peptide (0, 0.45, 1.35 and 4.05 μg/ml).
Figures 30A, 30B:
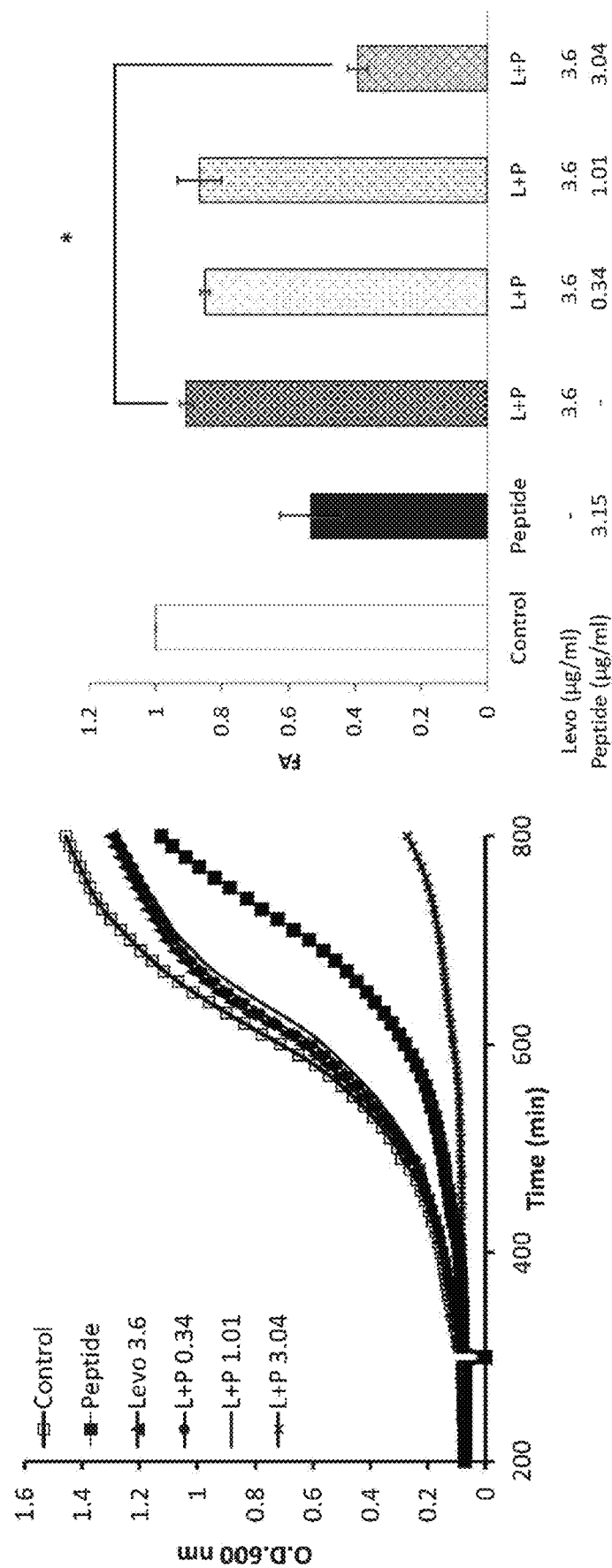
FIGS. 30A and 30B show the effect of BCC02-5R-MP (SEQ ID NO:21) in combination with Levofloxacin (Levo) and peptide combinations included a constant amount of Levofloxacin (3.6 μg/ml) with suboptimal amounts of peptide (0, 0.34, 1.01, 3.04 μg/ml).

To establish whether this effect might be seen with antibiotics from a different class, it was selected to perform these studies with Ciprofloxacin (FIG. 29A-B) and Levofloxacin (FIG. 30A-B). The addition of 4.05 µg/ml of peptide to 2.1 µg/ml of Ciprofloxacin significantly affected killing (P=0.0003 by unpaired t test). In other words, the methods described herein were able to reduce the MIC from 8.4 µg/ml to 2.1 µg/ml (FIG. 29A-B). Similarly, the methods were able to reduce the MIC of Levofloxacin from 15 µg/ml to 3.5 µg/ml in the presence of 3.04 µg/ml of the peptide (FIG. 30A-B).

While the presently disclosed inventive concepts have been described herein in connection with certain embodiments so that aspects thereof may be more fully understood and appreciated, it is not intended that the presently disclosed inventive concepts be limited to these particular embodiments. On the contrary, it is intended that all alternatives, modifications and equivalents are included within the scope of the presently disclosed inventive concepts as defined herein. Thus the examples described above, which include particular embodiments, will serve to illustrate the practice of the presently disclosed inventive concepts, it being understood that the particulars shown are by way of example and for purposes of illustrative discussion of particular embodiments of the presently disclosed inventive concepts only and are presented in the cause of providing what is believed to be the most useful and readily understood description of procedures as well as of the principles and conceptual aspects of the inventive concepts. Changes may be made in the formulation of the various compositions described herein, the methods described herein or in the steps or the sequence of steps of the methods described herein without departing from the spirit and scope of the presently disclosed inventive concepts.

What is claimed is:

1. A method of treating a wound in a subject in need of such therapy, the method comprising the steps of:

providing a composition comprising:

(1) a peptide compound consisting of:

(AEEA)-(AEEA)-RRRRGTRCQVAGWGSWHSG-GRLSRFPRFVNVR (SEQ ID NO:51), and/or (2) a peptide compound consisting of:

(AEEP)-(AEEP)-RRRRGTRCQVAGWGSWHSG-GRLSRFPRFVNVR (SEQ ID NO:35), wherein AEEA is $NH_2CH_2CH_2OCH_2CH_2OCH_2CO-$, and AEEP is $NH_2CH_2CH_2OCH_2CH_2OCH_2CH_2CO-$; and a pharmaceutically-acceptable vehicle, carrier, or diluent; and administering the composition to the wound in the subject.

2. The method of claim 1, wherein the composition comprises a lotion, paste, gel, cream, ointment, powder, spray, or aerosol.

* * * * *

UNITED STATES PATENT AND TRADEMARK OFFICE
CERTIFICATE OF CORRECTION

PATENT NO. : 11,884,710 B2
APPLICATION NO. : 17/532307
DATED : January 30, 2024
INVENTOR(S) : Heloise Anne Pereira, Anne Kasus-Jacobi and Gina L. Griffith It is certified that error appears in the above-identified patent and that said Letters Patent is hereby corrected as shown below:

In the Specification

Column 2, Line 49: Delete "BCC002-5RMP" and replace with -- BCC02-5RMP --
Column 3, Line 47: Delete "IL-10," and replace with -- IL-1β, --
Column 6, Line 7: After "peptides 95-122" delete "(SEQ TD NO:26)," and replace with -- (SEQ ID NO:26), --
Column 8, Line 9: Delete "BCC002-5R-MP" and replace with -- BCC02-5R-MP --
Column 10, Line 67: Delete "BCC002-5RMP, and BCC002-5RMP," and replace with -- BCC02-5RMP, and BCC02-5RMP, --
Column 31, Line 66: Delete "BCC002-5RMP" and replace with -- BCC02-5RMP --
Column 32, Line 9: Delete "BCC002-5RMP" and replace with -- BCC02-5RMP --
Column 32, Line 19: Delete "BCC002-5RMP" and replace with -- BCC02-5RMP --
Column 32, Line 20: Delete "BCC003-5RMP" and replace with -- BCC03-5RMP --
Column 32, Line 32: Delete "BCC003-5RMP" and replace with -- BCC03-5RMP --
Column 32, Line 63-65: Delete "BCC002-5R (SEQ ID NO: 18), BCC002-5RMP (SEQ ID NO: 21), BCC003-5R (SEQ ID NO: 19), BCC003-5RMP (SEQ ID NO:22), and BCC003-MP" and replace with -- BCC02-5R (SEQ ID NO: 18), BCC02-5RMP (SEQ ID NO: 21), BCC03-5R (SEQ ID NO: 19), BCC03-5RMP (SEQ ID NO:22), and BCC03-MP --
Column 33, Lines 1-2: Delete "BCC003-5R (SEQ ID NO: 19) and BCC003-5RMP" and replace with -- BCC03-5R (SEQ ID NO: 19) and BCC03-5RMP --
Column 33, Line 4: Delete "BCC003-MP" and replace with -- BCC03-MP --
Column 33, Line 11: Delete "BCC002" and replace with -- BCC02 --
Column 33, Lines 14-17: Delete "BCC002 (SEQ ID NO: 21). The data generally indicate the superiority of BCC003-5RMP (SEQ ID NO:22) and BCC002-5RMP" and replace with -- BCC02 (SEQ ID NO: 21). The data generally indicate the superiority of BCC03-5RMP (SEQ ID NO:22) and BCC02-5RMP --
Column 33, Line 19: Delete "BCC003-5RMP" and replace with -- BCC03-5RMP --
Column 34, Line 1: Delete "BCC002-5RMP" and replace with -- BCC02-5RMP --
Column 34, Line 4: Delete "BCC002-5RMP" and replace with -- BCC02-5RMP --
Column 34, Line 5: Delete "BCC002-5RMP" and replace with -- BCC02-5RMP --

Signed and Sealed this
Ninth Day of April, 2024

Katherine Kelly Vidal
*Director of the United States Patent and Trademark Office*

CERTIFICATE OF CORRECTION (continued)　　　　　　　　　　　　　　　　　　　　　　　Page 2 of 2
U.S. Pat. No. 11,884,710 B2

Column 35, Line 52: Delete "BCC002-5RMP (SEQ ID NO:21), and BCC003-5RMP" and replace with -- BCC02-5RMP (SEQ ID NO:21), and BCC03-5RMP --
Column 36, Line 48: Delete "BCC003-5RMP" and replace with -- BCC03-5RMP --
Column 36, Line 51: Delete "BCC003-5R" and replace with -- BCC03-5R --
Column 36, Line 52: Delete "BCC003-5RMP" and replace with -- BCC03-5RMP --
Column 36, Line 56: Delete "BCC003-5RMP," and replace with -- BCC03-5RMP, --
Column 46, Line 65: Delete "β-18 hours." and replace with -- 0-18 hours. --
Column 49, Line 11: Delete "3-actin" and replace with -- β-actin --
Column 54, Line 47: Delete "BCC002-5RMP (SEQ ID NO:21)" and replace with -- BCC02-5RMP (SEQ ID NO:21) --
Column 55, Line 6: Delete "BCC002-5RMP" and replace with -- BCC02-5RMP --
Column 55, Line 24: Delete "BCC002-5RMP" and replace with -- BCC02-5RMP --

SEQUENCE LISTING

<160> NUMBER OF SEQ ID NOS: 51

<210> SEQ ID NO 1
<211> LENGTH: 25
<212> TYPE: PRT
<213> ORGANISM: Homo sapiens

<400> SEQUENCE: 1

Asn Gln Gly Arg His Phe Ser Gly Gly Ala Leu Ile His Ala Arg Phe
1               5                   10                  15

Val Met Thr Ala Ala Ser Cys Phe Gln

```
              20                  25

<210> SEQ ID NO 2
<211> LENGTH: 25
<212> TYPE: PRT
<213> ORGANISM: Artificial Sequence
<220> FEATURE:
<223> OTHER INFORMATION: derivative of a peptide of Homo sapiens CAP37
      protein

<400> SEQUENCE: 2

Asn Gln Gly Arg His Phe Thr Gly Gly Ala Leu Ile His Ala Arg Phe
1               5                   10                  15

Val Met Thr Ala Ala Ser Cys Phe Gln
              20                  25

<210> SEQ ID NO 3
<211> LENGTH: 25
<212> TYPE: PRT
<213> ORGANISM: Artificial sequence
<220> FEATURE:
<223> OTHER INFORMATION: derivative of a peptide of Homo sapiens CAP37
      protein

<400> SEQUENCE: 3

Asn Gln Gly Arg His Phe Met Gly Gly Ala Leu Ile His Ala Arg Phe
1               5                   10                  15

Val Met Thr Ala Ala Ser Cys Phe Gln
              20                  25

<210> SEQ ID NO 4
<211> LENGTH: 25
<212> TYPE: PRT
<213> ORGANISM: Homo sapiens

<400> SEQUENCE: 4

Asn Gln Gly Arg His Phe Cys Gly Gly Ala Leu Ile His Ala Arg Phe
1               5                   10                  15

Val Met Thr Ala Ala Ser Ser Phe Gln
              20                  25

<210> SEQ ID NO 5
<211> LENGTH: 25
<212> TYPE: PRT
<213> ORGANISM: Artificial sequence
<220> FEATURE:
<223> OTHER INFORMATION: derivative of a peptide of Homo sapiens CAP37
      protein

<400> SEQUENCE: 5

Asn Gln Gly Arg His Phe Cys Gly Gly Ala Leu Ile His Ala Arg Phe
1               5                   10                  15

Val Met Thr Ala Ala Ser Thr Phe Gln
              20                  25

<210> SEQ ID NO 6
<211> LENGTH: 25
<212> TYPE: PRT
<213> ORGANISM: artificial sequence
<220> FEATURE:
<223> OTHER INFORMATION: derivative of a peptide of Homo sapiens CAP37
      protein

<400> SEQUENCE: 6

Asn Gln Gly Arg His Phe Cys Gly Gly Ala Leu Ile His Ala Arg Phe
```

```
1               5                   10                  15
Val Met Thr Ala Ala Ser Met Phe Gln
            20                  25

<210> SEQ ID NO 7
<211> LENGTH: 25
<212> TYPE: PRT
<213> ORGANISM: Homo sapiens

<400> SEQUENCE: 7

Asn Gln Gly Arg His Phe Cys Gly Gly Ala Leu Ile His Ala Arg Phe
1               5                   10                  15

Val Met Thr Ala Ala Ser Cys Phe Gln
            20                  25

<210> SEQ ID NO 8
<211> LENGTH: 20
<212> TYPE: PRT
<213> ORGANISM: Artificial sequence
<220> FEATURE:
<223> OTHER INFORMATION: derivative of a peptide of Homo sapiens CAP37
      protein

<400> SEQUENCE: 8

Arg His Phe Ser Gly Gly Ala Leu Ile His Ala Arg Phe Val Met Thr
1               5                   10                  15

Ala Ala Ser Cys
            20

<210> SEQ ID NO 9
<211> LENGTH: 20
<212> TYPE: PRT
<213> ORGANISM: artificial sequence
<220> FEATURE:
<223> OTHER INFORMATION: derivative of a peptide of Homo sapiens CAP37
      protein

<400> SEQUENCE: 9

Arg His Phe Thr Gly Gly Ala Leu Ile His Ala Arg Phe Val Met Thr
1               5                   10                  15

Ala Ala Ser Cys
            20

<210> SEQ ID NO 10
<211> LENGTH: 20
<212> TYPE: PRT
<213> ORGANISM: artificial sequence
<220> FEATURE:
<223> OTHER INFORMATION: derivative of a peptide of Homo sapiens CAP37
      protein

<400> SEQUENCE: 10

Arg His Phe Met Gly Gly Ala Leu Ile His Ala Arg Phe Val Met Thr
1               5                   10                  15

Ala Ala Ser Cys
            20

<210> SEQ ID NO 11
<211> LENGTH: 20
<212> TYPE: PRT
<213> ORGANISM: artificial sequence
<220> FEATURE:
<223> OTHER INFORMATION: derivative of a peptide of Homo sapiens CAP37
      protein
```

```
<400> SEQUENCE: 11

Arg His Phe Cys Gly Gly Ala Leu Ile His Ala Arg Phe Val Met Thr
1               5                   10                  15

Ala Ala Ser Ser
            20

<210> SEQ ID NO 12
<211> LENGTH: 20
<212> TYPE: PRT
<213> ORGANISM: artificial sequence
<220> FEATURE:
<223> OTHER INFORMATION: derivative of peptide from Homo sapiens CAP37
      protein

<400> SEQUENCE: 12

Arg His Phe Cys Gly Gly Ala Leu Ile His Ala Arg Phe Val Met Thr
1               5                   10                  15

Ala Ala Ser Thr
            20

<210> SEQ ID NO 13
<211> LENGTH: 20
<212> TYPE: PRT
<213> ORGANISM: artificial sequence
<220> FEATURE:
<223> OTHER INFORMATION: derivative of peptide of Homo sapiens CAP37
      protein

<400> SEQUENCE: 13

Arg His Phe Cys Gly Gly Ala Leu Ile His Ala Arg Phe Val Met Thr
1               5                   10                  15

Ala Ala Ser Met
            20

<210> SEQ ID NO 14
<211> LENGTH: 20
<212> TYPE: PRT
<213> ORGANISM: Homo sapiens

<400> SEQUENCE: 14

Arg His Phe Cys Gly Gly Ala Leu Ile His Ala Arg Phe Val Met Thr
1               5                   10                  15

Ala Ala Ser Cys
            20

<210> SEQ ID NO 15
<211> LENGTH: 4
<212> TYPE: PRT
<213> ORGANISM: artificial sequence
<220> FEATURE:
<223> OTHER INFORMATION: four arginine residue sequence

<400> SEQUENCE: 15

Arg Arg Arg Arg
1

<210> SEQ ID NO 16
<211> LENGTH: 5
<212> TYPE: PRT
<213> ORGANISM: artificial sequence
<220> FEATURE:
<223> OTHER INFORMATION: five arginine residue sequence

<400> SEQUENCE: 16
```

```
Arg Arg Arg Arg Arg
1               5

<210> SEQ ID NO 17
<211> LENGTH: 6
<212> TYPE: PRT
<213> ORGANISM: artificial sequence
<220> FEATURE:
<223> OTHER INFORMATION: six arginine residue sequence

<400> SEQUENCE: 17

Arg Arg Arg Arg Arg Arg
1               5

<210> SEQ ID NO 18
<211> LENGTH: 30
<212> TYPE: PRT
<213> ORGANISM: artificial sequence
<220> FEATURE:
<223> OTHER INFORMATION: 5-arginine peptide derivative of CAP37 peptide

<400> SEQUENCE: 18

Arg Arg Arg Arg Asn Gln Gly Arg His Phe Ser Gly Gly Ala Leu Ile
1               5                   10                  15

His Ala Arg Phe Val Met Thr Ala Ala Ser Cys Phe Gln Arg
            20                  25                  30

<210> SEQ ID NO 19
<211> LENGTH: 30
<212> TYPE: PRT
<213> ORGANISM: artificial sequence
<220> FEATURE:
<223> OTHER INFORMATION: five-arginine derivative of a CAP37 peptide

<400> SEQUENCE: 19

Arg Arg Arg Arg Asn Gln Gly Arg His Phe Cys Gly Gly Ala Leu Ile
1               5                   10                  15

His Ala Arg Phe Val Met Thr Ala Ala Ser Ser Phe Gln Arg
            20                  25                  30

<210> SEQ ID NO 20
<211> LENGTH: 30
<212> TYPE: PRT
<213> ORGANISM: artificial sequence
<220> FEATURE:
<223> OTHER INFORMATION: five arginine peptide derivative of CAP37
      peptide

<400> SEQUENCE: 20

Arg Arg Arg Arg Asn Gln Gly Arg His Phe Cys Gly Gly Ala Leu Ile
1               5                   10                  15

His Ala Arg Phe Val Met Thr Ala Ala Ser Cys Phe Gln Arg
            20                  25                  30

<210> SEQ ID NO 21
<211> LENGTH: 30
<212> TYPE: PRT
<213> ORGANISM: artificial sequence
<220> FEATURE:
<223> OTHER INFORMATION: BCC02-5RMP
<220> FEATURE:
<221> NAME/KEY: MISC_FEATURE
<222> LOCATION: (1)..(1)
<223> OTHER INFORMATION: (AEEP)-(AEEP) linked to amino terminal end of
      peptide backbone

<400> SEQUENCE: 21
```

Arg Arg Arg Arg Asn Gln Gly Arg His Phe Ser Gly Gly Ala Leu Ile
1               5                   10                  15

His Ala Arg Phe Val Met Thr Ala Ala Ser Cys Phe Gln Arg
            20                  25                  30

<210> SEQ ID NO 22
<211> LENGTH: 30
<212> TYPE: PRT
<213> ORGANISM: artificial sequence
<220> FEATURE:
<223> OTHER INFORMATION: BCC03-5RMP
<220> FEATURE:
<221> NAME/KEY: MISC_FEATURE
<222> LOCATION: (1)..(1)
<223> OTHER INFORMATION: (AEEP)-(AEEP) linked to amino terminal end of
      peptide backbone

<400> SEQUENCE: 22

Arg Arg Arg Arg Asn Gln Gly Arg His Phe Cys Gly Gly Ala Leu Ile
1               5                   10                  15

His Ala Arg Phe Val Met Thr Ala Ala Ser Ser Phe Gln Arg
            20                  25                  30

<210> SEQ ID NO 23
<211> LENGTH: 30
<212> TYPE: PRT
<213> ORGANISM: artificial sequence
<220> FEATURE:
<223> OTHER INFORMATION: BCC01-5RMP
<220> FEATURE:
<221> NAME/KEY: MISC_FEATURE
<222> LOCATION: (1)..(1)
<223> OTHER INFORMATION: (AEEP)-(AEEP) linked to amino terminal end of
      peptide backbone

<400> SEQUENCE: 23

Arg Arg Arg Arg Asn Gln Gly Arg His Phe Cys Gly Gly Ala Leu Ile
1               5                   10                  15

His Ala Arg Phe Val Met Thr Ala Ala Ser Cys Phe Gln Arg
            20                  25                  30

<210> SEQ ID NO 24
<211> LENGTH: 25
<212> TYPE: PRT
<213> ORGANISM: artificial sequence
<220> FEATURE:
<223> OTHER INFORMATION: BCC03-MP
<220> FEATURE:
<221> NAME/KEY: MISC_FEATURE
<222> LOCATION: (1)..(1)
<223> OTHER INFORMATION: (AEEP)-(AEEP) linked to amino terminal end of
      peptide backbone

<400> SEQUENCE: 24

Asn Gln Gly Arg His Phe Cys Gly Gly Ala Leu Ile His Ala Arg Phe
1               5                   10                  15

Val Met Thr Ala Ala Ser Ser Phe Gln
            20                  25

<210> SEQ ID NO 25
<211> LENGTH: 20
<212> TYPE: PRT
<213> ORGANISM: artificial sequence
<220> FEATURE:
<223> OTHER INFORMATION: consensus sequence for Pep of Formula (I)
<220> FEATURE:
<221> NAME/KEY: MISC_FEATURE

```
<222> LOCATION: (3)..(3)
<223> OTHER INFORMATION: Phe, Tyr, Arg, Lys, or His
<220> FEATURE:
<221> NAME/KEY: MISC_FEATURE
<222> LOCATION: (4)..(4)
<223> OTHER INFORMATION: Cys, Ser, Thr, or Met
<220> FEATURE:
<221> NAME/KEY: MISC_FEATURE
<222> LOCATION: (5)..(5)
<223> OTHER INFORMATION: Gly or Ala
<220> FEATURE:
<221> NAME/KEY: MISC_FEATURE
<222> LOCATION: (6)..(6)
<223> OTHER INFORMATION: Gly or Ala
<220> FEATURE:
<221> NAME/KEY: MISC_FEATURE
<222> LOCATION: (7)..(7)
<223> OTHER INFORMATION: Ala, Leu, Ile, or Val
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Ala, Leu, Ile, or Val
<220> FEATURE:
<221> NAME/KEY: MISC_FEATURE
<222> LOCATION: (11)..(11)
<223> OTHER INFORMATION: Ala, Leu, Ile, or Val
<220> FEATURE:
<221> NAME/KEY: MISC_FEATURE
<222> LOCATION: (13)..(13)
<223> OTHER INFORMATION: Phe, Tyr, Arg, Lys, or His
<220> FEATURE:
<221> NAME/KEY: MISC_FEATURE
<222> LOCATION: (14)..(14)
<223> OTHER INFORMATION: Ala, Leu, Ile, or Val
<220> FEATURE:
<221> NAME/KEY: MISC_FEATURE
<222> LOCATION: (16)..(16)
<223> OTHER INFORMATION: Ser, Thr, or Met
<220> FEATURE:
<221> NAME/KEY: MISC_FEATURE
<222> LOCATION: (17)..(17)
<223> OTHER INFORMATION: Ala, Leu, Ile, or Val
<220> FEATURE:
<221> NAME/KEY: MISC_FEATURE
<222> LOCATION: (18)..(18)
<223> OTHER INFORMATION: Ala, Leu, Ile, or Val
<220> FEATURE:
<221> NAME/KEY: MISC_FEATURE
<222> LOCATION: (19)..(19)
<223> OTHER INFORMATION: Ser, Thr, or Met
<220> FEATURE:
<221> NAME/KEY: MISC_FEATURE
<222> LOCATION: (20)..(20)
<223> OTHER INFORMATION: Cys, Ser, Thr, or Met

<400> SEQUENCE: 25

Arg His Xaa Xaa Xaa Xaa Xaa Xaa Xaa His Xaa Arg Xaa Xaa Met Xaa
1               5                   10                  15

Xaa Xaa Xaa Xaa
            20

<210> SEQ ID NO 26
<211> LENGTH: 28
<212> TYPE: PRT
<213> ORGANISM: Homo sapiens

<400> SEQUENCE: 26

Leu Asp Arg Glu Ala Asn Leu Thr Ser Ser Val Thr Ile Leu Pro Leu
1               5                   10                  15

Pro Leu Gln Asn Ala Thr Val Glu Ala Gly Thr Arg
```

```
                        20                  25

<210> SEQ ID NO 27
<211> LENGTH: 21
<212> TYPE: PRT
<213> ORGANISM: Homo sapiens

<400> SEQUENCE: 27

Thr Ser Ser Val Thr Ile Leu Pro Leu Pro Leu Gln Asn Ala Thr Val
1               5                   10                  15

Glu Ala Gly Thr Arg
            20

<210> SEQ ID NO 28
<211> LENGTH: 27
<212> TYPE: PRT
<213> ORGANISM: Homo sapiens

<400> SEQUENCE: 28

Gly Thr Arg Cys Gln Val Ala Gly Trp Gly Ser Gln Arg Ser Gly Gly
1               5                   10                  15

Arg Leu Ser Arg Phe Pro Arg Phe Val Asn Val
            20                  25

<210> SEQ ID NO 29
<211> LENGTH: 27
<212> TYPE: PRT
<213> ORGANISM: artificial sequence
<220> FEATURE:
<223> OTHER INFORMATION: derivative of peptide of Homo sapiens CAP37
      protein

<400> SEQUENCE: 29

Gly Thr Arg Cys Gln Val Ala Gly Trp Gly Ser Gln His Ser Gly Gly
1               5                   10                  15

Arg Leu Ser Arg Phe Pro Arg Phe Val Asn Val
            20                  25

<210> SEQ ID NO 30
<211> LENGTH: 27
<212> TYPE: PRT
<213> ORGANISM: artificial sequence
<220> FEATURE:
<223> OTHER INFORMATION: derivative of peptide of Homo sapiens CAP37
      protein

<400> SEQUENCE: 30

Gly Thr Arg Cys Gln Val Ala Gly Trp Gly Ser Trp Arg Ser Gly Gly
1               5                   10                  15

Arg Leu Ser Arg Phe Pro Arg Phe Val Asn Val
            20                  25

<210> SEQ ID NO 31
<211> LENGTH: 27
<212> TYPE: PRT
<213> ORGANISM: artificial sequence
<220> FEATURE:
<223> OTHER INFORMATION: derivative of peptide of CAP37 protein

<400> SEQUENCE: 31

Gly Thr Arg Cys Gln Val Ala Gly Trp Gly Ser Trp His Ser Gly Gly
1               5                   10                  15

Arg Leu Ser Arg Phe Pro Arg Phe Val Asn Val
            20                  25
```

<210> SEQ ID NO 32
<211> LENGTH: 32
<212> TYPE: PRT
<213> ORGANISM: artificial sequence
<220> FEATURE:
<223> OTHER INFORMATION: 120-146QR-5RMP
<220> FEATURE:
<221> NAME/KEY: MISC_FEATURE
<222> LOCATION: (1)..(1)
<223> OTHER INFORMATION: (AEEP)-(AEEP) linked to amino terminal end of
      peptide backbone

<400> SEQUENCE: 32

Arg Arg Arg Arg Gly Thr Arg Cys Gln Val Ala Gly Trp Gly Ser Gln
1               5                   10                  15

Arg Ser Gly Gly Arg Leu Ser Arg Phe Pro Arg Phe Val Asn Val Arg
            20                  25                  30

<210> SEQ ID NO 33
<211> LENGTH: 32
<212> TYPE: PRT
<213> ORGANISM: artificial sequence
<220> FEATURE:
<223> OTHER INFORMATION: 120-146QH-5RMP
<220> FEATURE:
<221> NAME/KEY: MISC_FEATURE
<222> LOCATION: (1)..(1)
<223> OTHER INFORMATION: (AEEP)-(AEEP) linked to amino terminal end of
      peptide backbone

<400> SEQUENCE: 33

Arg Arg Arg Arg Gly Thr Arg Cys Gln Val Ala Gly Trp Gly Ser Gln
1               5                   10                  15

His Ser Gly Gly Arg Leu Ser Arg Phe Pro Arg Phe Val Asn Val Arg
            20                  25                  30

<210> SEQ ID NO 34
<211> LENGTH: 32
<212> TYPE: PRT
<213> ORGANISM: artificial sequence
<220> FEATURE:
<223> OTHER INFORMATION: 120-146WR-5RMP
<220> FEATURE:
<221> NAME/KEY: MISC_FEATURE
<222> LOCATION: (1)..(1)
<223> OTHER INFORMATION: (AEEP)-(AEEP) linked to amino terminal end of
      peptide backbone

<400> SEQUENCE: 34

Arg Arg Arg Arg Gly Thr Arg Cys Gln Val Ala Gly Trp Gly Ser Trp
1               5                   10                  15

Arg Ser Gly Gly Arg Leu Ser Arg Phe Pro Arg Phe Val Asn Val Arg
            20                  25                  30

<210> SEQ ID NO 35
<211> LENGTH: 32
<212> TYPE: PRT
<213> ORGANISM: artificial sequence
<220> FEATURE:
<223> OTHER INFORMATION: 120-146WH-5RMP
<220> FEATURE:
<221> NAME/KEY: MISC_FEATURE
<222> LOCATION: (1)..(1)
<223> OTHER INFORMATION: (AEEP)-(AEEP) linked to amino terminal end of
      peptide backbone

<400> SEQUENCE: 35

-continued

Arg Arg Arg Arg Gly Thr Arg Cys Gln Val Ala Gly Trp Gly Ser Trp
1               5                   10                  15

His Ser Gly Gly Arg Leu Ser Arg Phe Pro Arg Phe Val Asn Val Arg
            20                  25                  30

<210> SEQ ID NO 36
<211> LENGTH: 30
<212> TYPE: PRT
<213> ORGANISM: artificial sequence
<220> FEATURE:
<223> OTHER INFORMATION: 20-44thr26-5RMP
<220> FEATURE:
<221> NAME/KEY: MISC_FEATURE
<222> LOCATION: (1)..(1)
<223> OTHER INFORMATION: (AEEP)-(AEEP) linked to amino terminal end of
      peptide backbone

<400> SEQUENCE: 36

Arg Arg Arg Arg Asn Gln Gly Arg His Phe Thr Gly Gly Ala Leu Ile
1               5                   10                  15

His Ala Arg Phe Val Met Thr Ala Ala Ser Cys Phe Gln Arg
            20                  25                  30

<210> SEQ ID NO 37
<211> LENGTH: 30
<212> TYPE: PRT
<213> ORGANISM: artificial sequence
<220> FEATURE:
<223> OTHER INFORMATION: 20-44met26-5RMP
<220> FEATURE:
<221> NAME/KEY: MISC_FEATURE
<222> LOCATION: (1)..(1)
<223> OTHER INFORMATION: (AEEP)-(AEEP) linked to amino terminal end of
      peptide backbone

<400> SEQUENCE: 37

Arg Arg Arg Arg Asn Gln Gly Arg His Phe Met Gly Gly Ala Leu Ile
1               5                   10                  15

His Ala Arg Phe Val Met Thr Ala Ala Ser Cys Phe Gln Arg
            20                  25                  30

<210> SEQ ID NO 38
<211> LENGTH: 30
<212> TYPE: PRT
<213> ORGANISM: artificial sequence
<220> FEATURE:
<223> OTHER INFORMATION: 20-44thr42-5RMP
<220> FEATURE:
<221> NAME/KEY: MISC_FEATURE
<222> LOCATION: (1)..(1)
<223> OTHER INFORMATION: (AEEP)-(AEEP) linked to amino terminal end of
      peptide backbone

<400> SEQUENCE: 38

Arg Arg Arg Arg Asn Gln Gly Arg His Phe Cys Gly Gly Ala Leu Ile
1               5                   10                  15

His Ala Arg Phe Val Met Thr Ala Ala Ser Thr Phe Gln Arg
            20                  25                  30

<210> SEQ ID NO 39
<211> LENGTH: 30
<212> TYPE: PRT
<213> ORGANISM: artificial sequence
<220> FEATURE:
<223> OTHER INFORMATION: 20-44met42-5RMP
<220> FEATURE:
<221> NAME/KEY: MISC_FEATURE
<222> LOCATION: (1)..(1)

```
<223> OTHER INFORMATION: (AEEP)-(AEEP) linked to amino terminal end of
      peptide backbone

<400> SEQUENCE: 39

Arg Arg Arg Arg Asn Gln Gly Arg His Phe Cys Gly Gly Ala Leu Ile
1               5                   10                  15

His Ala Arg Phe Val Met Thr Ala Ala Ser Met Phe Gln Arg
            20                  25                  30

<210> SEQ ID NO 40
<211> LENGTH: 25
<212> TYPE: PRT
<213> ORGANISM: artificial sequence
<220> FEATURE:
<223> OTHER INFORMATION: 23-42ser26-5RMP
<220> FEATURE:
<221> NAME/KEY: MISC_FEATURE
<222> LOCATION: (1)..(1)
<223> OTHER INFORMATION: (AEEP)-(AEEP) linked to amino terminal end of
      peptide backbone

<400> SEQUENCE: 40

Arg Arg Arg Arg Arg His Phe Ser Gly Gly Ala Leu Ile His Ala Arg
1               5                   10                  15

Phe Val Met Thr Ala Ala Ser Cys Arg
            20                  25

<210> SEQ ID NO 41
<211> LENGTH: 25
<212> TYPE: PRT
<213> ORGANISM: artificial sequence
<220> FEATURE:
<223> OTHER INFORMATION: 23-42thr26-5RMP
<220> FEATURE:
<221> NAME/KEY: MISC_FEATURE
<222> LOCATION: (1)..(1)
<223> OTHER INFORMATION: (AEEP)-(AEEP) linked to amino terminal end of
      peptide backbone

<400> SEQUENCE: 41

Arg Arg Arg Arg Arg His Phe Thr Gly Gly Ala Leu Ile His Ala Arg
1               5                   10                  15

Phe Val Met Thr Ala Ala Ser Cys Arg
            20                  25

<210> SEQ ID NO 42
<211> LENGTH: 25
<212> TYPE: PRT
<213> ORGANISM: artificial sequence
<220> FEATURE:
<223> OTHER INFORMATION: 23-42met26-5RMP
<220> FEATURE:
<221> NAME/KEY: MISC_FEATURE
<222> LOCATION: (1)..(1)
<223> OTHER INFORMATION: (AEEP)-(AEEP) linked to amino terminal end of
      peptide backbone

<400> SEQUENCE: 42

Arg Arg Arg Arg Arg His Phe Met Gly Gly Ala Leu Ile His Ala Arg
1               5                   10                  15

Phe Val Met Thr Ala Ala Ser Cys Arg
            20                  25

<210> SEQ ID NO 43
<211> LENGTH: 25
<212> TYPE: PRT
<213> ORGANISM: artificial sequence
```

```
<220> FEATURE:
<223> OTHER INFORMATION: 23-42ser42-5RMP
<220> FEATURE:
<221> NAME/KEY: MISC_FEATURE
<222> LOCATION: (1)..(1)
<223> OTHER INFORMATION: (AEEP)-(AEEP) linked to amino terminal end of
      peptide backbone

<400> SEQUENCE: 43

Arg Arg Arg Arg Arg His Phe Cys Gly Gly Ala Leu Ile His Ala Arg
1               5                   10                  15

Phe Val Met Thr Ala Ala Ser Ser Arg
            20                  25

<210> SEQ ID NO 44
<211> LENGTH: 25
<212> TYPE: PRT
<213> ORGANISM: artificial sequence
<220> FEATURE:
<223> OTHER INFORMATION: 23-42thr42-5RMP
<220> FEATURE:
<221> NAME/KEY: MISC_FEATURE
<222> LOCATION: (1)..(1)
<223> OTHER INFORMATION: (AEEP)-(AEEP) linked to amino terminal end of
      peptide backbone

<400> SEQUENCE: 44

Arg Arg Arg Arg Arg His Phe Cys Gly Gly Ala Leu Ile His Ala Arg
1               5                   10                  15

Phe Val Met Thr Ala Ala Ser Thr Arg
            20                  25

<210> SEQ ID NO 45
<211> LENGTH: 25
<212> TYPE: PRT
<213> ORGANISM: artificial sequence
<220> FEATURE:
<223> OTHER INFORMATION: 23-42met42-5RMP
<220> FEATURE:
<221> NAME/KEY: MISC_FEATURE
<222> LOCATION: (1)..(1)
<223> OTHER INFORMATION: (AEEP)-(AEEP) linked to amino terminal end of
      peptide backbone

<400> SEQUENCE: 45

Arg Arg Arg Arg Arg His Phe Cys Gly Gly Ala Leu Ile His Ala Arg
1               5                   10                  15

Phe Val Met Thr Ala Ala Ser Met Arg
            20                  25

<210> SEQ ID NO 46
<211> LENGTH: 33
<212> TYPE: PRT
<213> ORGANISM: artificial sequence
<220> FEATURE:
<223> OTHER INFORMATION: 95-122-5RMP(AEEP)
<220> FEATURE:
<221> NAME/KEY: MISC_FEATURE
<222> LOCATION: (1)..(1)
<223> OTHER INFORMATION: (AEEP)-(AEEP) linked to amino terminal end of
      peptide backbone

<400> SEQUENCE: 46

Arg Arg Arg Arg Leu Asp Arg Glu Ala Asn Leu Thr Ser Ser Val Thr
1               5                   10                  15

Ile Leu Pro Leu Pro Leu Gln Asn Ala Thr Val Glu Ala Gly Thr Arg
            20                  25                  30
```

Arg

```
<210> SEQ ID NO 47
<211> LENGTH: 20
<212> TYPE: PRT
<213> ORGANISM: artificial sequence
<220> FEATURE:
<223> OTHER INFORMATION: consensus sequence for Pep of Formula (I)
<220> FEATURE:
<221> NAME/KEY: MISC_FEATURE
<222> LOCATION: (3)..(3)
<223> OTHER INFORMATION: Phe, Arg, Lys, or His
<220> FEATURE:
<221> NAME/KEY: MISC_FEATURE
<222> LOCATION: (4)..(4)
<223> OTHER INFORMATION: Cys, Ser, Thr, or Met
<220> FEATURE:
<221> NAME/KEY: MISC_FEATURE
<222> LOCATION: (5)..(5)
<223> OTHER INFORMATION: Gly or Ala
<220> FEATURE:
<221> NAME/KEY: MISC_FEATURE
<222> LOCATION: (6)..(6)
<223> OTHER INFORMATION: Gly or Ala
<220> FEATURE:
<221> NAME/KEY: MISC_FEATURE
<222> LOCATION: (7)..(7)
<223> OTHER INFORMATION: Ala, leu, Ile, or Val
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Ala, leu, Ile, or Val
<220> FEATURE:
<221> NAME/KEY: MISC_FEATURE
<222> LOCATION: (11)..(11)
<223> OTHER INFORMATION: Ala, leu, Ile, or Val
<220> FEATURE:
<221> NAME/KEY: MISC_FEATURE
<222> LOCATION: (13)..(13)
<223> OTHER INFORMATION: Phe, Arg, Lys, or His
<220> FEATURE:
<221> NAME/KEY: MISC_FEATURE
<222> LOCATION: (14)..(14)
<223> OTHER INFORMATION: Ala, leu, Ile, or Val
<220> FEATURE:
<221> NAME/KEY: MISC_FEATURE
<222> LOCATION: (16)..(16)
<223> OTHER INFORMATION: Ser, Thr, or Met
<220> FEATURE:
<221> NAME/KEY: MISC_FEATURE
<222> LOCATION: (17)..(17)
<223> OTHER INFORMATION: Ala, leu, Ile, or Val
<220> FEATURE:
<221> NAME/KEY: MISC_FEATURE
<222> LOCATION: (18)..(18)
<223> OTHER INFORMATION: Ala, leu, Ile, or Val
<220> FEATURE:
<221> NAME/KEY: MISC_FEATURE
<222> LOCATION: (19)..(19)
<223> OTHER INFORMATION: Ser, Thr, or Met
<220> FEATURE:
<221> NAME/KEY: MISC_FEATURE
<222> LOCATION: (20)..(20)
<223> OTHER INFORMATION: Cys, Ser, Thr, or Met

<400> SEQUENCE: 47

Arg His Xaa Xaa Xaa Xaa Xaa Xaa Xaa His Xaa Arg Xaa Xaa Met Xaa
1               5                   10                  15

Xaa Xaa Xaa Xaa
            20
```

```
<210> SEQ ID NO 48
<211> LENGTH: 33
<212> TYPE: PRT
<213> ORGANISM: artificial sequence
<220> FEATURE:
<223> OTHER INFORMATION: 95-122-5RMP(AEEA)
<220> FEATURE:
<221> NAME/KEY: MISC_FEATURE
<222> LOCATION: (1)..(1)
<223> OTHER INFORMATION: (AEEA)-(AEEA) linked to amino terminal end of
      peptide backbone

<400> SEQUENCE: 48

Arg Arg Arg Arg Leu Asp Arg Glu Ala Asn Leu Thr Ser Ser Val Thr
1               5                   10                  15

Ile Leu Pro Leu Pro Leu Gln Asn Ala Thr Val Glu Ala Gly Thr Arg
            20                  25                  30

Arg

<210> SEQ ID NO 49
<211> LENGTH: 26
<212> TYPE: PRT
<213> ORGANISM: artificial sequence
<220> FEATURE:
<223> OTHER INFORMATION: 102-122-5RMP(AEEP)
<220> FEATURE:
<221> NAME/KEY: MISC_FEATURE
<222> LOCATION: (1)..(1)
<223> OTHER INFORMATION: (AEEP)-(AEEP) linked to amino terminal end of
      peptide backbone

<400> SEQUENCE: 49

Arg Arg Arg Arg Thr Ser Ser Val Thr Ile Leu Pro Leu Pro Leu Gln
1               5                   10                  15

Asn Ala Thr Val Glu Ala Gly Thr Arg Arg
            20                  25

<210> SEQ ID NO 50
<211> LENGTH: 26
<212> TYPE: PRT
<213> ORGANISM: artificial sequence
<220> FEATURE:
<223> OTHER INFORMATION: 102-122-5RMP(AEEA)
<220> FEATURE:
<221> NAME/KEY: MISC_FEATURE
<222> LOCATION: (1)..(1)
<223> OTHER INFORMATION: (AEEA)-(AEEA) linked to amino terminal end of
      peptide backbone

<400> SEQUENCE: 50

Arg Arg Arg Arg Thr Ser Ser Val Thr Ile Leu Pro Leu Pro Leu Gln
1               5                   10                  15

Asn Ala Thr Val Glu Ala Gly Thr Arg Arg
            20                  25

<210> SEQ ID NO 51
<211> LENGTH: 32
<212> TYPE: PRT
<213> ORGANISM: artificial sequence
<220> FEATURE:
<223> OTHER INFORMATION: 120-146WH-5RMP(AEEA)
<220> FEATURE:
<221> NAME/KEY: MISC_FEATURE
<222> LOCATION: (1)..(1)
<223> OTHER INFORMATION: (AEEA)-(AEEA) linked to amino terminal end of
      peptide backbone

<400> SEQUENCE: 51
```

```
Arg Arg Arg Arg Gly Thr Arg Cys Gln Val Ala Gly Trp Gly Ser Trp
1           5               10                  15

His Ser Gly Gly Arg Leu Ser Arg Phe Pro Arg Phe Val Asn Val Arg
            20              25              30
```